United States Patent
Kaneda et al.

(10) Patent No.: US 11,166,995 B2
(45) Date of Patent: Nov. 9, 2021

(54) ANTICANCER AGENT COMPRISING HVJ-E AND IMMUNE CHECKPOINT PROTEIN INHIBITOR

(71) Applicants: OSAKA UNIVERSITY, Suita (JP); GENOMIDEA INC., Osaka (JP)

(72) Inventors: Yasufumi Kaneda, Suita (JP); Kazuma Sakura, Suita (JP); Tomoyuki Nishikawa, Suita (JP); Masanori Fukushima, Kobe (JP); Toshihiro Nakajima, Ikeda (JP)

(73) Assignees: OSAKA UNIVERSITY, Suita (JP); GENOMIDEA INC., Osaka (JP)

( * ) Notice: Subject to any disclaimer, the term of this patent is extended or adjusted under 35 U.S.C. 154(b) by 0 days.

(21) Appl. No.: 16/346,576

(22) PCT Filed: Nov. 1, 2017

(86) PCT No.: PCT/JP2017/039568
§ 371 (c)(1),
(2) Date: May 1, 2019

(87) PCT Pub. No.: WO2018/084185
PCT Pub. Date: May 11, 2018

(65) Prior Publication Data
US 2019/0275091 A1 Sep. 12, 2019

(30) Foreign Application Priority Data
Nov. 1, 2016 (JP) .............................. JP2016-214198

(51) Int. Cl.
| | | |
|---|---|---|
| A61K 35/76 | (2015.01) | |
| A61P 35/00 | (2006.01) | |
| C12N 7/00 | (2006.01) | |
| A61K 39/395 | (2006.01) | |
| A61K 31/7105 | (2006.01) | |
| A61K 45/00 | (2006.01) | |
| A61P 43/00 | (2006.01) | |
| A61K 31/711 | (2006.01) | |
| A61P 35/02 | (2006.01) | |
| A61P 37/04 | (2006.01) | |

(52) U.S. Cl.
CPC ............ *A61K 35/76* (2013.01); *A61K 31/711* (2013.01); *A61K 31/7105* (2013.01); *A61K 39/395* (2013.01); *A61K 39/39558* (2013.01); *A61K 45/00* (2013.01); *A61P 35/00* (2018.01); *A61P 35/02* (2018.01); *A61P 37/04* (2018.01); *A61P 43/00* (2018.01); *C12N 7/00* (2013.01); *C12N 2760/18633* (2013.01); *C12N 2760/18671* (2013.01)

(58) Field of Classification Search
None
See application file for complete search history.

(56) References Cited

U.S. PATENT DOCUMENTS

| | | | |
|---|---|---|---|
| 5,631,237 | A | 5/1997 | Dzau et al. |
| 2003/0013195 | A1 | 1/2003 | Kaneda |
| 2004/0265283 | A1 | 12/2004 | Morishita |
| 2006/0002894 | A1 | 1/2006 | Kaneda et al. |
| 2006/0165656 | A1 | 7/2006 | Yamamoto et al. |
| 2007/0287677 | A1 | 12/2007 | Kaneda |
| 2008/0226674 | A1 | 9/2008 | Kotani et al. |
| 2009/0082263 | A1 | 3/2009 | Kaneda et al. |
| 2011/0223148 | A1 | 9/2011 | Kaneda et al. |
| 2016/0000909 | A1 | 1/2016 | Eisenbach-Schwartz et al. |
| 2019/0358276 | A1 | 11/2019 | Kaneda et al. |

FOREIGN PATENT DOCUMENTS

| | | |
|---|---|---|
| EP | 1449542 A1 | 8/2004 |
| EP | 1568379 A1 | 8/2005 |
| EP | 1782821 | 5/2007 |
| EP | 3536329 A1 | 9/2019 |
| EP | 3560505 A1 | 10/2019 |
| JP | 2002-065278 A | 3/2002 |
| JP | 4441263 B2 | 3/2010 |
| KR | 10-2016-0133510 A | 11/2016 |
| WO | WO 2001/057204 A1 | 8/2001 |
| WO | WO 2004/035779 A1 | 4/2004 |
| WO | WO 2004/039406 A1 | 5/2004 |
| WO | WO 2005/094878 A1 | 10/2005 |
| WO | WO 2005/095613 A1 | 10/2005 |
| WO | WO 2006/011600 A1 | 2/2006 |
| WO | WO 2010/032764 A1 | 3/2010 |
| WO | WO 2015/136541 A2 | 9/2015 |
| WO | WO 2018/105630 A1 | 6/2018 |

OTHER PUBLICATIONS

Mahoney et al., The Next Immune-Checkpoint Inhibitors: PD-1/PD-L1 Blockade in Melanoma, 2015, Clin Ther, vol. 37, No. 4, pp. 764-782.*

Hui et al., Induction of Apoptosis in Hormone-resistant Human Prostate Cancer PC3 Cells by Inactivated Sendai Virus, Biomed Environ Sci, 2014; 27(7): pp. 506-514.*

Quan et al., Inactivated Sendai Virus Suppresses Murine Melanoma Growth by Inducing Host Immune Responses and Down-regulating β-catenin Expression, Biomed Environ Sci, 2012; 25(5): pp. 509-516.*

Baruch et al., "PD-1 immune checkpoint blockade reduces pathology and improves memory in mouse models of Alzheimer's disease," *Nat. Med.*, 22(2): 135-137 (2016).

(Continued)

*Primary Examiner* — Benjamin P Blumel
(74) *Attorney, Agent, or Firm* — Leydig, Voit & Mayer, Ltd.

(57) ABSTRACT

The present invention provides an anticancer agent containing the following (1) and (2):
(1) HVJ-E (hemagglutinating virus of Japan envelope),
(2) an inhibitor of an immune checkpoint protein.

6 Claims, 6 Drawing Sheets

Specification includes a Sequence Listing.

(56) References Cited

OTHER PUBLICATIONS

Dong et al., "Tumor-associated B7-H1 promotes T-cell apoptosis: A potential mechanism of immune evasion," *Nat. Med.*, 8/(8): 793-800 (2002).
Dzau et al., "Fusigenic viral liposome for gene therapy in cardiovascular diseases," *Proc. Natl. Acad. Sci. U.S.A.*, 93(21): 11421-11425 (1996).
Jinushi, "Basis and Clinical Application of TIM-3 Molecule," *Modern Medicine*, 70(3): 366-371 (2015).
Kaneda et al., "Gene therapy using HVJ-liposomes: the best of both worlds?" *Mol. Med. Today*, 5(7): 298-303 (1999).
Kaneda et al., "Hemagglutinating Virus of Japan (HVJ) Envelope Vector as a Versatile Gene Delivery System," *Mol. Ther.*, 6(2): 219-226 (2002).
Kaneda, "Development of anti-cancer strategies using HVJ envelope," *J. Gene Med.*, 14(11): 652 (2012).
Kawaguchi et al., "Efficient eradication of hormone-resistant human prostate cancers by inactivated Sendai virus particle," *Int. J. Cancer*, 124(10): 2478-2487 (2009).
Kleffel et al., "Melanoma Cell-Intrinsic PD-1 Receptor Functions Promote Tumor Growth," *Cell*, 162(6): 1242-1256 (2015).
Korman et al., "Checkpoint Blockade in Cancer Immunotherapy," *Adv. Immunol.*, 90: 297-339 (2006).
Kurooka et al., "Inactivated Sendai Virus Particles Eradicate Tumors by Inducing Immune Responses through Blocking Regulatory T Cells," *Cancer Res.*, 67(1): 227-236 (2007).
Kurooka et al., "1. Development of Antitumor Immunotherapy using Inactivated Sendai Virus Particles," *Virus*, 57(1): 19-27 (2007).
Littman, "Releasing the Brakes on Cancer Immunotherapy," *Cell*, 162(6): 1186-1190 (2015).
Maeda, "Basis and Clinical Application of OX40," *Modern Medicine*, 70(3): 372-377 (2015).
Matsushima-Miyagi et al., "TRAIL and Noxa Are Selectively Upregulated in Prostate Cancer Cells Downstream of the RIG-I/MAVS Signaling Pathway by Nonreplicating Sendai Virus Particles," *Clin. Cancer Res.*, 18(22): 6271-6283 (2012).
Nomura et al., "Accumulation of Cytosolic Calcium Induces Necroptotic Cell Death in Human Neuroblastoma," *Cancer Res.*, 74(4): 1056-1066 (2014).
Ott et al., "CTLA-4 and PD-1/PD-L1 Blockade: New Immunotherapeutic Modalities with Durable Clinical Benefit in Melanoma Patients," *Clin. Cancer Res.*, 19(19): 5300-5309 (2013).
Sharma et al., "The future of immune checkpoint therapy," *Science*, 348(6230): 56-61 (2015).
Schenk et al., "Immunization with amyloid-β attenuates Alzheimer disease-like pathology in the PDAPP mouse," *Nature*, 400: 173-177 (1999).
Suzuki et al., "Sendai virus F glycoprotein induces IL-6 production in dendritic cells in a fusion-independent manner," *FEBS Lett.*, 582(9): 1325-1329 (2008).
Topalian et al., "Safety, Activity, and Immune Correlates of Anti-PD-1 Antibody in Cancer," *N. Engl. J. Med.*, 366(26): 2443-2454 (2012).
Tumeh et al., "PD-1 blockade induces responses by inhibiting adaptive immune resistance," *Nature*, 515(7528): 568-571 (2014).
Uhara, "Treatment with Molecular Target Drug," *Pharma. Med.*, 33(6): 15-19 (2015).
Wolchok, "PD-1 Blockers," *Cell*, 162(5): 937 (2015).
Yamazaki et al., "Development of Therapy of Malignant Melanoma with Anti-CTLA-4 Antibody and Anti-PD-1 Antibody," *Modern Medicine*, 70(3): 399-407 (2015).
Japanese Patent Office, International Search Report in International Patent Application No. PCT/JP2017/039568 (dated Jan. 23, 2018).
Japanese Patent Office, International Search Report in International Patent Application No. PCT/JP2017/043725 (dated Jan. 23, 2018).
Yoshimura et al., "Gene Transfer of Hepatocyte Growth Factor to Subarachnoid Space in Cerebral Hypoperfusion Model," *Hypertension*, 39(5): 1028-1034 (2002).
European Patent Office, Extended European Search Report in European Patent Application No. 17877435.2 (dated Jun. 12, 2020).
Chang et al., "Virus-stimulated neutrophils in the tumor microenvironment enhance T cell-mediated anti-tumor immunity," *Oncotarget*, 7(27): 42195-42207 (2016).
Fujita et al., "Phase I/II Clinical Trial to Assess Safety and Efficacy of Intratumoral and Subcutaneous Injection of HVJ-E to Castration Resistant Prostate Cancer Patients," *The Journal of Urology*, 195(4S): Abstract No. PD32-04, p. e762 (2016).
Kaneda et al., "Development and application of DDS to activate anti-tumor immunity," *Drug Delivery System*, 32(3): 208-217 (2017) [EM Base Database, Accession No. EMB-20170758371].
Kaneda, "Virosome: A novel vector to enable multi-modal strategies for cancer therapy," *Adv, Drug Deliv. Rev.*, 64(8): 730-738 (2012).
Kiyohara et al., "Intratumoral injection of hemagglutinating virus of Japan-envelope vector yielded an antitumor effect for advanced melanoma: a phase I/IIa clinical study," *Cancer Immunol. Immunother.*, 69(6): 1131-1140 (2020).
Nakajima et al., "A Novel Therapy for Melanoma and Prostate Cancer Using a Non-Replicating Sendai Virus Particle (HVJ-E)," in *Novel Gene Therapy Approaches*, chapter 8, pp. 157-181 (Feb. 13, 2013).
Saga et al., "Systemic Administration of a Novel Immune-Stimulatory Pseudovirion Suppresses Lung Metastatic Melanoma by Regionally Enhancing IFN-γ Production," *Clin. Cancer Res.*, 19(3): 668-679 (2013).
Tanemura et al., "Recent advances and developments in the anti-tumor effect of the HVJ envelope vector on malignant melanoma: from the bench to clinical application," *Cancer Gene Ther.*, 20(11): 599-605 (2013).
European Patent Office, Supplementary European Search Report in European Patent Application No. 17867818 (dated May 13, 2020).
U.S. Appl. No. 16/466,206, filed Jun. 3, 2019.
Korean Patent Office, Notice of Allowance in Korean Patent Application No. 10-2019-7015863 (dated Feb. 22, 2021).
European Patent Office, Communication Pursuant to Article 94(3) EPC in European Patent Application No. 17877435.2 (dated Oct. 23, 2020).

\* cited by examiner

SEQUENCE LISTING

<160> NUMBER OF SEQ ID NOS: 32

<210> SEQ ID NO 1
<211> LENGTH: 867
<212> TYPE: DNA
<213> ORGANISM: Homo sapiens
<220> FEATURE:
<221> NAME/KEY: CDS
<222> LOCATION: (1)..(867)

<400> SEQUENCE: 1

```
atg cag atc cca cag gcg ccc tgg cca gtc gtc tgg gcg gtg cta caa      48
Met Gln Ile Pro Gln Ala Pro Trp Pro Val Val Trp Ala Val Leu Gln
1               5                   10                  15 ctg ggc tgg cgg cca gga tgg ttc tta gac tcc cca gac agg ccc tgg      96
Leu Gly Trp Arg Pro Gly Trp Phe Leu Asp Ser Pro Asp Arg Pro Trp
            20                  25                  30 aac ccc ccc acc ttc tcc cca gcc ctg ctc gtg gtg acc gaa ggg gac     144
Asn Pro Pro Thr Phe Ser Pro Ala Leu Leu Val Val Thr Glu Gly Asp
        35                  40                  45 aac gcc acc ttc acc tgc agc ttc tcc aac aca tcg gag agc ttc gtg     192
Asn Ala Thr Phe Thr Cys Ser Phe Ser Asn Thr Ser Glu Ser Phe Val
    50                  55                  60 cta aac tgg tac cgc atg agc ccc agc aac cag acg gac aag ctg gcc     240
Leu Asn Trp Tyr Arg Met Ser Pro Ser Asn Gln Thr Asp Lys Leu Ala
65                  70                  75                  80 gcc ttc ccc gag gac cgc agc cag ccc ggc cag gac tgc cgc ttc cgt     288
Ala Phe Pro Glu Asp Arg Ser Gln Pro Gly Gln Asp Cys Arg Phe Arg
                85                  90                  95 gtc aca caa ctg ccc aac ggg cgt gac ttc cac atg agc gtg gtc agg     336
Val Thr Gln Leu Pro Asn Gly Arg Asp Phe His Met Ser Val Val Arg
            100                 105                 110 gcc cgg cgc aat gac agc ggc acc tac ctc tgt ggg gcc atc tcc ctg     384
Ala Arg Arg Asn Asp Ser Gly Thr Tyr Leu Cys Gly Ala Ile Ser Leu
        115                 120                 125 gcc ccc aag gcg cag atc aaa gag agc ctg cgg gca gag ctc agg gtg     432
Ala Pro Lys Ala Gln Ile Lys Glu Ser Leu Arg Ala Glu Leu Arg Val
    130                 135                 140 aca gag aga agg gca gaa gtg ccc aca gcc cac ccc agc ccc tca ccc     480
Thr Glu Arg Arg Ala Glu Val Pro Thr Ala His Pro Ser Pro Ser Pro
145                 150                 155                 160 agg cca gcc ggc cag ttc caa acc ctg gtg gtt ggt gtc gtg ggc ggc     528
Arg Pro Ala Gly Gln Phe Gln Thr Leu Val Val Gly Val Val Gly Gly
                165                 170                 175 ctg ctg ggc agc ctg gtg ctg cta gtc tgg gtc ctg gcc gtc atc tgc     576
Leu Leu Gly Ser Leu Val Leu Leu Val Trp Val Leu Ala Val Ile Cys
            180                 185                 190 tcc cgg gcc gca cga ggg aca ata gga gcc agg cgc acc ggc cag ccc     624
Ser Arg Ala Ala Arg Gly Thr Ile Gly Ala Arg Arg Thr Gly Gln Pro
        195                 200                 205 ctg aag gag gac cca tca gcc gtg cct gtg ttc tct gtg gac tat ggg     672
Leu Lys Glu Asp Pro Ser Ala Val Pro Val Phe Ser Val Asp Tyr Gly
    210                 215                 220 gag ctg gat ttc cag tgg cga gag aag acc ccg gag ccc ccc gtg ccc     720
Glu Leu Asp Phe Gln Trp Arg Glu Lys Thr Pro Glu Pro Pro Val Pro
225                 230                 235                 240 tgt gtc cct gag cag acg gag tat gcc acc att gtc ttt cct agc gga     768
```

```
Cys Val Pro Glu Gln Thr Glu Tyr Ala Thr Ile Val Phe Pro Ser Gly
                245                 250                 255 atg ggc acc tca tcc ccc gcc cgc agg ggc tca gct gac ggc cct cgg        816
Met Gly Thr Ser Ser Pro Ala Arg Arg Gly Ser Ala Asp Gly Pro Arg
        260                 265                 270 agt gcc cag cca ctg agg cct gag gat gga cac tgc tct tgg ccc ctc        864
Ser Ala Gln Pro Leu Arg Pro Glu Asp Gly His Cys Ser Trp Pro Leu
    275                 280                 285 tga                                                                    867

<210> SEQ ID NO 2
<211> LENGTH: 288
<212> TYPE: PRT
<213> ORGANISM: Homo sapiens

<400> SEQUENCE: 2

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 3
<211> LENGTH: 531
<212> TYPE: DNA
```

```
<213> ORGANISM: Homo sapiens
<220> FEATURE:
<221> NAME/KEY: CDS
<222> LOCATION: (1)..(531)

<400> SEQUENCE: 3 atg agg ata ttt gct gtc ttt ata ttc atg acc tac tgg cat ttg ctg      48
Met Arg Ile Phe Ala Val Phe Ile Phe Met Thr Tyr Trp His Leu Leu
1               5                   10                  15 aac gcc cca tac aac aaa atc aac caa aga att ttg gtt gtg gat cca      96
Asn Ala Pro Tyr Asn Lys Ile Asn Gln Arg Ile Leu Val Val Asp Pro
            20                  25                  30 gtc acc tct gaa cat gaa ctg aca tgt cag gct gag ggc tac ccc aag     144
Val Thr Ser Glu His Glu Leu Thr Cys Gln Ala Glu Gly Tyr Pro Lys
        35                  40                  45 gcc gaa gtc atc tgg aca agc agt gac cat caa gtc ctg agt ggt aag     192
Ala Glu Val Ile Trp Thr Ser Ser Asp His Gln Val Leu Ser Gly Lys
    50                  55                  60 acc acc acc acc aat tcc aag aga gag gag aag ctt ttc aat gtg acc     240
Thr Thr Thr Thr Asn Ser Lys Arg Glu Glu Lys Leu Phe Asn Val Thr
65                  70                  75                  80 agc aca ctg aga atc aac aca aca act aat gag att ttc tac tgc act     288
Ser Thr Leu Arg Ile Asn Thr Thr Thr Asn Glu Ile Phe Tyr Cys Thr
                85                  90                  95 ttt agg aga tta gat cct gag gaa aac cat aca gct gaa ttg gtc atc     336
Phe Arg Arg Leu Asp Pro Glu Glu Asn His Thr Ala Glu Leu Val Ile
            100                 105                 110 cca gaa cta cct ctg gca cat cct cca aat gaa agg act cac ttg gta     384
Pro Glu Leu Pro Leu Ala His Pro Pro Asn Glu Arg Thr His Leu Val
        115                 120                 125 att ctg gga gcc atc tta tta tgc ctt ggt gta gca ctg aca ttc atc     432
Ile Leu Gly Ala Ile Leu Leu Cys Leu Gly Val Ala Leu Thr Phe Ile
    130                 135                 140 ttc cgt tta aga aaa ggg aga atg atg gat gtg aaa aaa tgt ggc atc     480
Phe Arg Leu Arg Lys Gly Arg Met Met Asp Val Lys Lys Cys Gly Ile
145                 150                 155                 160 caa gat aca aac tca aag aag caa agt gat aca cat ttg gag gag acg     528
Gln Asp Thr Asn Ser Lys Lys Gln Ser Asp Thr His Leu Glu Glu Thr
                165                 170                 175 taa                                                                  531

<210> SEQ ID NO 4
<211> LENGTH: 176
<212> TYPE: PRT
<213> ORGANISM: Homo sapiens

<400> SEQUENCE: 4

Met Arg Ile Phe Ala Val Phe Ile Phe Met Thr Tyr Trp His Leu Leu
1               5                   10                  15

Asn Ala Pro Tyr Asn Lys Ile Asn Gln Arg Ile Leu Val Val Asp Pro
            20                  25                  30

Val Thr Ser Glu His Glu Leu Thr Cys Gln Ala Glu Gly Tyr Pro Lys
        35                  40                  45

Ala Glu Val Ile Trp Thr Ser Ser Asp His Gln Val Leu Ser Gly Lys
    50                  55                  60

Thr Thr Thr Thr Asn Ser Lys Arg Glu Glu Lys Leu Phe Asn Val Thr
65                  70                  75                  80

Ser Thr Leu Arg Ile Asn Thr Thr Thr Asn Glu Ile Phe Tyr Cys Thr
                85                  90                  95
```

```
Phe Arg Arg Leu Asp Pro Glu Glu Asn His Thr Ala Glu Leu Val Ile
                100                 105                 110

Pro Glu Leu Pro Leu Ala His Pro Pro Asn Glu Arg Thr His Leu Val
            115                 120                 125

Ile Leu Gly Ala Ile Leu Leu Cys Leu Gly Val Ala Leu Thr Phe Ile
        130                 135                 140

Phe Arg Leu Arg Lys Gly Arg Met Met Asp Val Lys Lys Cys Gly Ile
145                 150                 155                 160

Gln Asp Thr Asn Ser Lys Lys Gln Ser Asp Thr His Leu Glu Glu Thr
                165                 170                 175

<210> SEQ ID NO 5
<211> LENGTH: 822
<212> TYPE: DNA
<213> ORGANISM: Homo sapiens
<220> FEATURE:
<221> NAME/KEY: CDS
<222> LOCATION: (1)..(822)

<400> SEQUENCE: 5
```

| | | | | | | | | | | | | | | | | |
|---|---|---|---|---|---|---|---|---|---|---|---|---|---|---|---|---|
| atg | atc | ttc | ctc | ctg | cta | atg | ttg | agc | ctg | gaa | ttg | cag | ctt | cac | cag | 48 |
| Met | Ile | Phe | Leu | Leu | Leu | Met | Leu | Ser | Leu | Glu | Leu | Gln | Leu | His | Gln | |
| 1 | | | | 5 | | | | | 10 | | | | | 15 | | |
| ata | gca | gct | tta | ttc | aca | gtg | aca | gtc | cct | aag | gaa | ctg | tac | ata | ata | 96 |
| Ile | Ala | Ala | Leu | Phe | Thr | Val | Thr | Val | Pro | Lys | Glu | Leu | Tyr | Ile | Ile | |
| | | | | 20 | | | | | 25 | | | | | 30 | | |
| gag | cat | ggc | agc | aat | gtg | acc | ctg | gaa | tgc | aac | ttt | gac | act | gga | agt | 144 |
| Glu | His | Gly | Ser | Asn | Val | Thr | Leu | Glu | Cys | Asn | Phe | Asp | Thr | Gly | Ser | |
| | | 35 | | | | | 40 | | | | | 45 | | | | |
| cat | gtg | aac | ctt | gga | gca | ata | aca | gcc | agt | ttg | caa | aag | gtg | gaa | aat | 192 |
| His | Val | Asn | Leu | Gly | Ala | Ile | Thr | Ala | Ser | Leu | Gln | Lys | Val | Glu | Asn | |
| | 50 | | | | | 55 | | | | | 60 | | | | | |
| gat | aca | tcc | cca | cac | cgt | gaa | aga | gcc | act | ttg | ctg | gag | gag | cag | ctg | 240 |
| Asp | Thr | Ser | Pro | His | Arg | Glu | Arg | Ala | Thr | Leu | Leu | Glu | Glu | Gln | Leu | |
| 65 | | | | | 70 | | | | | 75 | | | | | 80 | |
| ccc | cta | ggg | aag | gcc | tcg | ttc | cac | ata | cct | caa | gtc | caa | gtg | agg | gac | 288 |
| Pro | Leu | Gly | Lys | Ala | Ser | Phe | His | Ile | Pro | Gln | Val | Gln | Val | Arg | Asp | |
| | | | | 85 | | | | | 90 | | | | | 95 | | |
| gaa | gga | cag | tac | caa | tgc | ata | atc | atc | tat | ggg | gtc | gcc | tgg | gac | tac | 336 |
| Glu | Gly | Gln | Tyr | Gln | Cys | Ile | Ile | Ile | Tyr | Gly | Val | Ala | Trp | Asp | Tyr | |
| | | | | 100 | | | | | 105 | | | | | 110 | | |
| aag | tac | ctg | act | ctg | aaa | gtc | aaa | gct | tcc | tac | agg | aaa | ata | aac | act | 384 |
| Lys | Tyr | Leu | Thr | Leu | Lys | Val | Lys | Ala | Ser | Tyr | Arg | Lys | Ile | Asn | Thr | |
| | | | 115 | | | | | 120 | | | | | 125 | | | |
| cac | atc | cta | aag | gtt | cca | gaa | aca | gat | gag | gta | gag | ctc | acc | tgc | cag | 432 |
| His | Ile | Leu | Lys | Val | Pro | Glu | Thr | Asp | Glu | Val | Glu | Leu | Thr | Cys | Gln | |
| | 130 | | | | | 135 | | | | | 140 | | | | | |
| gct | aca | ggt | tat | cct | ctg | gca | gaa | gta | tcc | tgg | cca | aac | gtc | agc | gtt | 480 |
| Ala | Thr | Gly | Tyr | Pro | Leu | Ala | Glu | Val | Ser | Trp | Pro | Asn | Val | Ser | Val | |
| 145 | | | | | 150 | | | | | 155 | | | | | 160 | |
| cct | gcc | aac | acc | agc | cac | tcc | agg | acc | cct | gaa | ggc | ctc | tac | cag | gtc | 528 |
| Pro | Ala | Asn | Thr | Ser | His | Ser | Arg | Thr | Pro | Glu | Gly | Leu | Tyr | Gln | Val | |
| | | | | 165 | | | | | 170 | | | | | 175 | | |
| acc | agt | gtt | ctg | cgc | cta | aag | cca | ccc | cct | ggc | aga | aac | ttc | agc | tgt | 576 |
| Thr | Ser | Val | Leu | Arg | Leu | Lys | Pro | Pro | Pro | Gly | Arg | Asn | Phe | Ser | Cys | |
| | | | 180 | | | | | 185 | | | | | 190 | | | |
| gtg | ttc | tgg | aat | act | cac | gtg | agg | gaa | ctt | act | ttg | gcc | agc | att | gac | 624 |
| Val | Phe | Trp | Asn | Thr | His | Val | Arg | Glu | Leu | Thr | Leu | Ala | Ser | Ile | Asp | |
| | | | 195 | | | | | 200 | | | | | 205 | | | |
| ctt | caa | agt | cag | atg | gaa | ccc | agg | acc | cat | cca | act | tgg | ctg | ctt | cac | 672 |

```
Leu Gln Ser Gln Met Glu Pro Arg Thr His Pro Thr Trp Leu Leu His
    210                 215                 220 att ttc atc ccc ttc tgc atc att gct ttc att ttc ata gcc aca gtg         720
Ile Phe Ile Pro Phe Cys Ile Ile Ala Phe Ile Phe Ile Ala Thr Val
225                 230                 235                 240 ata gcc cta aga aaa caa ctc tgt caa aag ctg tat tct tca aaa gac         768
Ile Ala Leu Arg Lys Gln Leu Cys Gln Lys Leu Tyr Ser Ser Lys Asp
                245                 250                 255 aca aca aaa aga cct gtc acc aca aca aag agg gaa gtg aac agt gct         816
Thr Thr Lys Arg Pro Val Thr Thr Lys Arg Glu Val Asn Ser Ala
                260                 265                 270 atc tga                                                                  822
Ile <210> SEQ ID NO 6
<211> LENGTH: 273
<212> TYPE: PRT
<213> ORGANISM: Homo sapiens

<400> SEQUENCE: 6

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
                20                  25                  30

Glu His Gly Ser Asn Val Thr Leu Glu Cys Asn Phe Asp Thr Gly Ser
            35                  40                  45

His Val Asn Leu Gly Ala Ile Thr Ala Ser Leu Gln Lys Val Glu Asn
        50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Phe Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
            260                 265                 270

Ile
```

<210> SEQ ID NO 7
<211> LENGTH: 525
<212> TYPE: DNA
<213> ORGANISM: Homo sapiens
<220> FEATURE:
<221> NAME/KEY: CDS
<222> LOCATION: (1)..(525)

<400> SEQUENCE: 7

| | | | | | | | | | | | | | | | | |
|---|---|---|---|---|---|---|---|---|---|---|---|---|---|---|---|---|
| atg | gct | tgc | ctt | gga | ttt | cag | cgg | cac | aag | gct | cag | ctg | aac | ctg | gct | 48 |
| Met | Ala | Cys | Leu | Gly | Phe | Gln | Arg | His | Lys | Ala | Gln | Leu | Asn | Leu | Ala | |
| 1 | | | | 5 | | | | | 10 | | | | | 15 | | |
| acc | agg | acc | tgg | ccc | tgc | act | ctc | ctg | ttt | ttt | ctt | ctc | ttc | atc | cct | 96 |
| Thr | Arg | Thr | Trp | Pro | Cys | Thr | Leu | Leu | Phe | Phe | Leu | Leu | Phe | Ile | Pro | |
| | | | 20 | | | | | 25 | | | | | 30 | | | |
| gtc | ttc | tgc | aaa | gca | atg | cac | gtg | gcc | cag | cct | gct | gtg | gta | ctg | gcc | 144 |
| Val | Phe | Cys | Lys | Ala | Met | His | Val | Ala | Gln | Pro | Ala | Val | Val | Leu | Ala | |
| | | 35 | | | | | 40 | | | | | 45 | | | | |
| agc | agc | cga | ggc | atc | gcc | agc | ttt | gtg | tgt | gag | tat | gca | tct | cca | ggc | 192 |
| Ser | Ser | Arg | Gly | Ile | Ala | Ser | Phe | Val | Cys | Glu | Tyr | Ala | Ser | Pro | Gly | |
| | 50 | | | | | 55 | | | | | 60 | | | | | |
| aaa | gcc | act | gag | gtc | cgg | gtg | aca | gtg | ctt | cgg | cag | gct | gac | agc | cag | 240 |
| Lys | Ala | Thr | Glu | Val | Arg | Val | Thr | Val | Leu | Arg | Gln | Ala | Asp | Ser | Gln | |
| 65 | | | | | 70 | | | | | 75 | | | | | 80 | |
| gtg | act | gaa | gtc | tgt | gcg | gca | acc | tac | atg | atg | ggg | aat | gag | ttg | acc | 288 |
| Val | Thr | Glu | Val | Cys | Ala | Ala | Thr | Tyr | Met | Met | Gly | Asn | Glu | Leu | Thr | |
| | | | | 85 | | | | | 90 | | | | | 95 | | |
| ttc | cta | gat | gat | tcc | atc | tgc | acg | ggc | acc | tcc | agt | gga | aat | caa | gtg | 336 |
| Phe | Leu | Asp | Asp | Ser | Ile | Cys | Thr | Gly | Thr | Ser | Ser | Gly | Asn | Gln | Val | |
| | | | 100 | | | | | 105 | | | | | 110 | | | |
| aac | ctc | act | atc | caa | gga | ctg | agg | gcc | atg | gac | acg | gga | ctc | tac | atc | 384 |
| Asn | Leu | Thr | Ile | Gln | Gly | Leu | Arg | Ala | Met | Asp | Thr | Gly | Leu | Tyr | Ile | |
| | | 115 | | | | | 120 | | | | | 125 | | | | |
| tgc | aag | gtg | gag | ctc | atg | tac | cca | ccg | cca | tac | tac | ctg | ggc | ata | ggc | 432 |
| Cys | Lys | Val | Glu | Leu | Met | Tyr | Pro | Pro | Pro | Tyr | Tyr | Leu | Gly | Ile | Gly | |
| | 130 | | | | | 135 | | | | | 140 | | | | | |
| aac | gga | acc | cag | att | tat | gta | att | gct | aaa | gaa | aag | aag | ccc | tct | tac | 480 |
| Asn | Gly | Thr | Gln | Ile | Tyr | Val | Ile | Ala | Lys | Glu | Lys | Lys | Pro | Ser | Tyr | |
| 145 | | | | | 150 | | | | | 155 | | | | | 160 | |
| aac | agg | ggt | cta | tgt | gaa | aat | gcc | ccc | aac | aga | gcc | aga | atg | tga | | 525 |
| Asn | Arg | Gly | Leu | Cys | Glu | Asn | Ala | Pro | Asn | Arg | Ala | Arg | Met | | | |
| | | | | 165 | | | | | 170 | | | | | | | |

<210> SEQ ID NO 8
<211> LENGTH: 174
<212> TYPE: PRT
<213> ORGANISM: Homo sapiens

<400> SEQUENCE: 8

| | | | | | | | | | | | | | | |
|---|---|---|---|---|---|---|---|---|---|---|---|---|---|---|
| Met | Ala | Cys | Leu | Gly | Phe | Gln | Arg | His | Lys | Ala | Gln | Leu | Asn | Leu | Ala |
| 1 | | | | 5 | | | | | 10 | | | | | 15 | |

| Thr | Arg | Thr | Trp | Pro | Cys | Thr | Leu | Leu | Phe | Phe | Leu | Leu | Phe | Ile | Pro |
|---|---|---|---|---|---|---|---|---|---|---|---|---|---|---|---|
| | | | 20 | | | | | 25 | | | | | 30 | | |

| Val | Phe | Cys | Lys | Ala | Met | His | Val | Ala | Gln | Pro | Ala | Val | Val | Leu | Ala |
|---|---|---|---|---|---|---|---|---|---|---|---|---|---|---|---|
| | | 35 | | | | | 40 | | | | | 45 | | | |

| Ser | Ser | Arg | Gly | Ile | Ala | Ser | Phe | Val | Cys | Glu | Tyr | Ala | Ser | Pro | Gly |
|---|---|---|---|---|---|---|---|---|---|---|---|---|---|---|---|
| | 50 | | | | | 55 | | | | | 60 | | | | |

| Lys | Ala | Thr | Glu | Val | Arg | Val | Thr | Val | Leu | Arg | Gln | Ala | Asp | Ser | Gln |
|---|---|---|---|---|---|---|---|---|---|---|---|---|---|---|---|
| 65 | | | | | 70 | | | | | 75 | | | | | 80 |

Val Thr Glu Val Cys Ala Ala Thr Tyr Met Met Gly Asn Glu Leu Thr

```
                85                  90                  95
Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
            115                 120                 125

Cys Lys Val Glu Leu Met Tyr Pro Pro Pro Tyr Leu Gly Ile Gly
            130                 135                 140

Asn Gly Thr Gln Ile Tyr Val Ile Ala Lys Glu Lys Lys Pro Ser Tyr
145                 150                 155                 160

Asn Arg Gly Leu Cys Glu Asn Ala Pro Asn Arg Ala Arg Met
                165                 170

<210> SEQ ID NO 9
<211> LENGTH: 867
<212> TYPE: DNA
<213> ORGANISM: Homo sapiens
<220> FEATURE:
<221> NAME/KEY: CDS
<222> LOCATION: (1)..(867)

<400> SEQUENCE: 9 atg ggc cac aca cgg agg cag gga aca tca cca tcc aag tgt cca tac      48
Met Gly His Thr Arg Arg Gln Gly Thr Ser Pro Ser Lys Cys Pro Tyr
1               5                   10                  15 ctc aat ttc ttt cag ctc ttg gtg ctg gct ggt ctt tct cac ttc tgt      96
Leu Asn Phe Phe Gln Leu Leu Val Leu Ala Gly Leu Ser His Phe Cys
            20                  25                  30 tca ggt gtt atc cac gtg acc aag gaa gtg aaa gaa gtg gca acg ctg     144
Ser Gly Val Ile His Val Thr Lys Glu Val Lys Glu Val Ala Thr Leu
        35                  40                  45 tcc tgt ggt cac aat gtt tct gtt gaa gag ctg gca caa act cgc atc     192
Ser Cys Gly His Asn Val Ser Val Glu Glu Leu Ala Gln Thr Arg Ile
    50                  55                  60 tac tgg caa aag gag aag aaa atg gtg ctg act atg atg tct ggg gac     240
Tyr Trp Gln Lys Glu Lys Lys Met Val Leu Thr Met Met Ser Gly Asp
65                  70                  75                  80 atg aat ata tgg ccc gag tac aag aac cgg acc atc ttt gat atc act     288
Met Asn Ile Trp Pro Glu Tyr Lys Asn Arg Thr Ile Phe Asp Ile Thr
                85                  90                  95 aat aac ctc tcc att gtg atc ctg gct ctg cgc cca tct gac gag ggc     336
Asn Asn Leu Ser Ile Val Ile Leu Ala Leu Arg Pro Ser Asp Glu Gly
            100                 105                 110 aca tac gag tgt gtt gtt ctg aag tat gaa aaa gac gct ttc aag cgg     384
Thr Tyr Glu Cys Val Val Leu Lys Tyr Glu Lys Asp Ala Phe Lys Arg
        115                 120                 125 gaa cac ctg gct gaa gtg acg tta tca gtc aaa gct gac ttc cct aca     432
Glu His Leu Ala Glu Val Thr Leu Ser Val Lys Ala Asp Phe Pro Thr
    130                 135                 140 cct agt ata tct gac ttt gaa att cca act tct aat att aga agg ata     480
Pro Ser Ile Ser Asp Phe Glu Ile Pro Thr Ser Asn Ile Arg Arg Ile
145                 150                 155                 160 att tgc tca acc tct gga ggt ttt cca gag cct cac ctc tcc tgg ttg     528
Ile Cys Ser Thr Ser Gly Gly Phe Pro Glu Pro His Leu Ser Trp Leu
                165                 170                 175 gaa aat gga gaa gaa tta aat gcc atc aac aca aca gtt tcc caa gat     576
Glu Asn Gly Glu Glu Leu Asn Ala Ile Asn Thr Thr Val Ser Gln Asp
            180                 185                 190 cct gaa act gag ctc tat gct gtt agc agc aaa ctg gat ttc aat atg     624
Pro Glu Thr Glu Leu Tyr Ala Val Ser Ser Lys Leu Asp Phe Asn Met
        195                 200                 205
```

```
aca acc aac cac agc ttc atg tgt ctc atc aag tat gga cat tta aga    672
Thr Thr Asn His Ser Phe Met Cys Leu Ile Lys Tyr Gly His Leu Arg
    210                 215                 220 gtg aat cag acc ttc aac tgg aat aca acc aag caa gag cat ttt cct    720
Val Asn Gln Thr Phe Asn Trp Asn Thr Thr Lys Gln Glu His Phe Pro
225                 230                 235                 240 gat aac ctg ctc cca tcc tgg gcc att acc tta atc tca gta aat gga    768
Asp Asn Leu Leu Pro Ser Trp Ala Ile Thr Leu Ile Ser Val Asn Gly
                245                 250                 255 att ttt gtg ata tgc tgc ctg acc tac tgc ttt gcc cca aga tgc aga    816
Ile Phe Val Ile Cys Cys Leu Thr Tyr Cys Phe Ala Pro Arg Cys Arg
                260                 265                 270 gag aga agg agg aat gag aga ttg aga agg gaa agt gta cgc cct gta    864
Glu Arg Arg Arg Asn Glu Arg Leu Arg Arg Glu Ser Val Arg Pro Val
                275                 280                 285 taa                                                                867
```

<210> SEQ ID NO 10
<211> LENGTH: 288
<212> TYPE: PRT
<213> ORGANISM: Homo sapiens

<400> SEQUENCE: 10

```
Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
                20                  25                  30

Ser Gly Val Ile His Val Thr Lys Glu Val Lys Glu Val Ala Thr Leu
            35                  40                  45

Ser Cys Gly His Asn Val Ser Val Glu Glu Leu Ala Gln Thr Arg Ile
        50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
                100                 105                 110

Thr Tyr Glu Cys Val Val Leu Lys Tyr Glu Lys Asp Ala Phe Lys Arg
            115                 120                 125

Glu His Leu Ala Glu Val Thr Leu Ser Val Lys Ala Asp Phe Pro Thr
        130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
                180                 185                 190

Pro Glu Thr Glu Leu Tyr Ala Val Ser Ser Lys Leu Asp Phe Asn Met
            195                 200                 205

Thr Thr Asn His Ser Phe Met Cys Leu Ile Lys Tyr Gly His Leu Arg
        210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255
```

```
Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
            275                 280                 285

<210> SEQ ID NO 11
<211> LENGTH: 654
<212> TYPE: DNA
<213> ORGANISM: Homo sapiens
<220> FEATURE:
<221> NAME/KEY: CDS
<222> LOCATION: (1)..(654)

<400> SEQUENCE: 11 atg gat ccc cag tgc act atg gga ctg agt aac att ctc ttt gtg atg      48
Met Asp Pro Gln Cys Thr Met Gly Leu Ser Asn Ile Leu Phe Val Met
1               5                   10                  15 gcc ttc ctg ctc tct gct aac ttc agt caa cct gaa ata gta cca att      96
Ala Phe Leu Leu Ser Ala Asn Phe Ser Gln Pro Glu Ile Val Pro Ile
            20                  25                  30 tct aat ata aca gaa aat gtg tac ata aat ttg acc tgc tca tct ata     144
Ser Asn Ile Thr Glu Asn Val Tyr Ile Asn Leu Thr Cys Ser Ser Ile
        35                  40                  45 cac ggt tac cca gaa cct aag aag atg agt gtt ttg cta aga acc aag     192
His Gly Tyr Pro Glu Pro Lys Lys Met Ser Val Leu Leu Arg Thr Lys
    50                  55                  60 aat tca act atc gag tat gat ggt att atg cag aaa tct caa gat aat     240
Asn Ser Thr Ile Glu Tyr Asp Gly Ile Met Gln Lys Ser Gln Asp Asn
65                  70                  75                  80 gtc aca gaa ctg tac gac gtt tcc atc agc ttg tct gtt tca ttc cct     288
Val Thr Glu Leu Tyr Asp Val Ser Ile Ser Leu Ser Val Ser Phe Pro
                85                  90                  95 gat gtt acg agc aat atg acc atc ttc tgt att ctg gaa act gac aag     336
Asp Val Thr Ser Asn Met Thr Ile Phe Cys Ile Leu Glu Thr Asp Lys
            100                 105                 110 acg cgg ctt tta tct tca cct ttc tct ata gag ctt gag gac cct cag     384
Thr Arg Leu Leu Ser Ser Pro Phe Ser Ile Glu Leu Glu Asp Pro Gln
        115                 120                 125 cct ccc cca gac cac att cct tgg att aca gct gta ctt cca aca gtt     432
Pro Pro Pro Asp His Ile Pro Trp Ile Thr Ala Val Leu Pro Thr Val
    130                 135                 140 att ata tgt gtg atg gtt ttc tgt cta att cta tgg aaa tgg aag aag     480
Ile Ile Cys Val Met Val Phe Cys Leu Ile Leu Trp Lys Trp Lys Lys
145                 150                 155                 160 aag aag cgg cct cgc aac tct tat aaa tgt gga acc aac aca atg gag     528
Lys Lys Arg Pro Arg Asn Ser Tyr Lys Cys Gly Thr Asn Thr Met Glu
                165                 170                 175 agg gaa gag agt gaa cag acc aag aaa aga gaa aaa atc cat ata cct     576
Arg Glu Glu Ser Glu Gln Thr Lys Lys Arg Glu Lys Ile His Ile Pro
            180                 185                 190 gaa aga tct gat gaa gcc cag cgt gtt ttt aaa agt tcg aag aca tct     624
Glu Arg Ser Asp Glu Ala Gln Arg Val Phe Lys Ser Ser Lys Thr Ser
        195                 200                 205 tca tgc gac aaa agt gat aca tgt ttt taa                             654
Ser Cys Asp Lys Ser Asp Thr Cys Phe
    210                 215

<210> SEQ ID NO 12
<211> LENGTH: 217
<212> TYPE: PRT
<213> ORGANISM: Homo sapiens
```

<400> SEQUENCE: 12

```
Met Asp Pro Gln Cys Thr Met Gly Leu Ser Asn Ile Leu Phe Val Met
1               5                   10                  15
Ala Phe Leu Leu Ser Ala Asn Phe Ser Gln Pro Glu Ile Val Pro Ile
            20                  25                  30
Ser Asn Ile Thr Glu Asn Val Tyr Ile Asn Leu Thr Cys Ser Ser Ile
        35                  40                  45
His Gly Tyr Pro Glu Pro Lys Lys Met Ser Val Leu Leu Arg Thr Lys
    50                  55                  60
Asn Ser Thr Ile Glu Tyr Asp Gly Ile Met Gln Lys Ser Gln Asp Asn
65                  70                  75                  80
Val Thr Glu Leu Tyr Asp Val Ser Ile Ser Leu Ser Val Ser Phe Pro
                85                  90                  95
Asp Val Thr Ser Asn Met Thr Ile Phe Cys Ile Leu Glu Thr Asp Lys
            100                 105                 110
Thr Arg Leu Leu Ser Ser Pro Phe Ser Ile Glu Leu Glu Asp Pro Gln
        115                 120                 125
Pro Pro Pro Asp His Ile Pro Trp Ile Thr Ala Val Leu Pro Thr Val
    130                 135                 140
Ile Ile Cys Val Met Val Phe Cys Leu Ile Leu Trp Lys Trp Lys Lys
145                 150                 155                 160
Lys Lys Arg Pro Arg Asn Ser Tyr Lys Cys Gly Thr Asn Thr Met Glu
                165                 170                 175
Arg Glu Glu Ser Glu Gln Thr Lys Lys Arg Glu Lys Ile His Ile Pro
            180                 185                 190
Glu Arg Ser Asp Glu Ala Gln Arg Val Phe Lys Ser Ser Lys Thr Ser
        195                 200                 205
Ser Cys Asp Lys Ser Asp Thr Cys Phe
    210                 215
```

<210> SEQ ID NO 13
<211> LENGTH: 1605
<212> TYPE: DNA
<213> ORGANISM: Homo sapiens
<220> FEATURE:
<221> NAME/KEY: CDS
<222> LOCATION: (1)..(1605)

<400> SEQUENCE: 13

```
atg ctg cgt cgg cgg ggc agc cct ggc atg ggt gtg cat gtg ggt gca      48
Met Leu Arg Arg Arg Gly Ser Pro Gly Met Gly Val His Val Gly Ala
1               5                   10                  15 gcc ctg gga gca ctg tgg ttc tgc ctc aca gga gcc ctg gag gtc cag      96
Ala Leu Gly Ala Leu Trp Phe Cys Leu Thr Gly Ala Leu Glu Val Gln
            20                  25                  30 gtc cct gaa gac cca gtg gtg gca ctg gtg ggc acc gat gcc acc ctg     144
Val Pro Glu Asp Pro Val Val Ala Leu Val Gly Thr Asp Ala Thr Leu
        35                  40                  45 tgc tgc tcc ttc tcc cct gag cct ggc ttc agc ctg gca cag ctc aac     192
Cys Cys Ser Phe Ser Pro Glu Pro Gly Phe Ser Leu Ala Gln Leu Asn
    50                  55                  60 ctc atc tgg cag ctg aca gat acc aaa cag ctg gtg cac agc ttt gct     240
Leu Ile Trp Gln Leu Thr Asp Thr Lys Gln Leu Val His Ser Phe Ala
65                  70                  75                  80 gag ggc cag gac cag ggc agc gcc tat gcc aac cgc acg gcc ctc ttc     288
Glu Gly Gln Asp Gln Gly Ser Ala Tyr Ala Asn Arg Thr Ala Leu Phe
                85                  90                  95
```

```
ccg gac ctg ctg gca cag ggc aac gca tcc ctg agg ctg cag cgc gtg          336
Pro Asp Leu Leu Ala Gln Gly Asn Ala Ser Leu Arg Leu Gln Arg Val
        100                 105                 110 cgt gtg gcg gac gag ggc agc ttc acc tgc ttc gtg agc atc cgg gat          384
Arg Val Ala Asp Glu Gly Ser Phe Thr Cys Phe Val Ser Ile Arg Asp
            115                 120                 125 ttc ggc agc gct gcc gtc agc ctg cag gtg gcc gct ccc tac tcg aag          432
Phe Gly Ser Ala Ala Val Ser Leu Gln Val Ala Ala Pro Tyr Ser Lys
        130                 135                 140 ccc agc atg acc ctg gag ccc aac aag gac ctg cgg cca ggg gac acg          480
Pro Ser Met Thr Leu Glu Pro Asn Lys Asp Leu Arg Pro Gly Asp Thr
145                 150                 155                 160 gtg acc atc acg tgc tcc agc tac cag ggc tac cct gag gct gag gtg          528
Val Thr Ile Thr Cys Ser Ser Tyr Gln Gly Tyr Pro Glu Ala Glu Val
                165                 170                 175 ttc tgg cag gat ggg cag ggt gtg ccc ctg act ggc aac gtg acc acg          576
Phe Trp Gln Asp Gly Gln Gly Val Pro Leu Thr Gly Asn Val Thr Thr
            180                 185                 190 tcg cag atg gcc aac gag cag ggc ttg ttt gat gtg cac agc atc ctg          624
Ser Gln Met Ala Asn Glu Gln Gly Leu Phe Asp Val His Ser Ile Leu
        195                 200                 205 cgg gtg gtg ctg ggt gca aat ggc acc tac agc tgc ctg gtg cgc aac          672
Arg Val Val Leu Gly Ala Asn Gly Thr Tyr Ser Cys Leu Val Arg Asn
210                 215                 220 ccc gtg ctg cag cag gat gcg cac agc tct gtc acc atc aca ccc cag          720
Pro Val Leu Gln Gln Asp Ala His Ser Ser Val Thr Ile Thr Pro Gln
225                 230                 235                 240 aga agc ccc aca gga gcc gtg gag gtc cag gtc cct gag gac ccg gtg          768
Arg Ser Pro Thr Gly Ala Val Glu Val Gln Val Pro Glu Asp Pro Val
                245                 250                 255 gtg gcc cta gtg ggc acc gat gcc acc ctg cgc tgc tcc ttc tcc ccc          816
Val Ala Leu Val Gly Thr Asp Ala Thr Leu Arg Cys Ser Phe Ser Pro
            260                 265                 270 gag cct ggc ttc agc ctg gca cag ctc aac ctc atc tgg cag ctg aca          864
Glu Pro Gly Phe Ser Leu Ala Gln Leu Asn Leu Ile Trp Gln Leu Thr
        275                 280                 285 gac acc aaa cag ctg gtg cac agt ttc acc gaa ggc cgg gac cag ggc          912
Asp Thr Lys Gln Leu Val His Ser Phe Thr Glu Gly Arg Asp Gln Gly
    290                 295                 300 agc gcc tat gcc aac cgc acg gcc ctc ttc ccg gac ctg ctg gca caa          960
Ser Ala Tyr Ala Asn Arg Thr Ala Leu Phe Pro Asp Leu Leu Ala Gln
305                 310                 315                 320 ggc aat gca tcc ctg agg ctg cag cgc gtg cgt gtg gcg gac gag ggc         1008
Gly Asn Ala Ser Leu Arg Leu Gln Arg Val Arg Val Ala Asp Glu Gly
                325                 330                 335 agc ttc acc tgc ttc gtg agc atc cgg gat ttc ggc agc gct gcc gtc         1056
Ser Phe Thr Cys Phe Val Ser Ile Arg Asp Phe Gly Ser Ala Ala Val
            340                 345                 350 agc ctg cag gtg gcc gct ccc tac tcg aag ccc agc atg acc ctg gag         1104
Ser Leu Gln Val Ala Ala Pro Tyr Ser Lys Pro Ser Met Thr Leu Glu
        355                 360                 365 ccc aac aag gac ctg cgg cca ggg gac acg gtg acc atc acg tgc tcc         1152
Pro Asn Lys Asp Leu Arg Pro Gly Asp Thr Val Thr Ile Thr Cys Ser
    370                 375                 380 agc tac cgg ggc tac cct gag gct gag gtg ttc tgg cag gat ggg cag         1200
Ser Tyr Arg Gly Tyr Pro Glu Ala Glu Val Phe Trp Gln Asp Gly Gln
385                 390                 395                 400 ggt gtg ccc ctg act ggc aac gtg acc acg tcg cag atg gcc aac gag         1248
Gly Val Pro Leu Thr Gly Asn Val Thr Thr Ser Gln Met Ala Asn Glu
                405                 410                 415
```

```
cag ggc ttg ttt gat gtg cac agc gtc ctg cgg gtg gtg ctg ggt gcg      1296
Gln Gly Leu Phe Asp Val His Ser Val Leu Arg Val Val Leu Gly Ala
        420                 425                 430 aat ggc acc tac agc tgc ctg gtg cgc aac ccc gtg ctg cag cag gat      1344
Asn Gly Thr Tyr Ser Cys Leu Val Arg Asn Pro Val Leu Gln Gln Asp
            435                 440                 445 gcg cac ggc tct gtc acc atc aca ggg cag cct atg aca ttc ccc cca      1392
Ala His Gly Ser Val Thr Ile Thr Gly Gln Pro Met Thr Phe Pro Pro
    450                 455                 460 gag gcc ctg tgg gtg acc gtg ggg ctg tct gtc tgt ctc att gca ctg      1440
Glu Ala Leu Trp Val Thr Val Gly Leu Ser Val Cys Leu Ile Ala Leu
465                 470                 475                 480 ctg gtg gcc ctg gct ttc gtg tgc tgg aga aag atc aaa cag agc tgt      1488
Leu Val Ala Leu Ala Phe Val Cys Trp Arg Lys Ile Lys Gln Ser Cys
                485                 490                 495 gag gag gag aat gca gga gct gag gac cag gat ggg gag gga gaa ggc      1536
Glu Glu Glu Asn Ala Gly Ala Glu Asp Gln Asp Gly Glu Gly Glu Gly
            500                 505                 510 tcc aag aca gcc ctg cag cct ctg aaa cac tct gac agc aaa gaa gat      1584
Ser Lys Thr Ala Leu Gln Pro Leu Lys His Ser Asp Ser Lys Glu Asp
    515                 520                 525 gat gga caa gaa ata gcc tga                                          1605
Asp Gly Gln Glu Ile Ala
    530
```

<210> SEQ ID NO 14
<211> LENGTH: 534
<212> TYPE: PRT
<213> ORGANISM: Homo sapiens

<400> SEQUENCE: 14

```
Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Ile Leu
        195                 200                 205
```

```
Arg Val Val Leu Gly Ala Asn Gly Thr Tyr Ser Cys Leu Val Arg Asn
    210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
                260                 265                 270

Glu Pro Gly Phe Ser Leu Ala Gln Leu Asn Leu Ile Trp Gln Leu Thr
                275                 280                 285

Asp Thr Lys Gln Leu Val His Ser Phe Thr Glu Gly Arg Asp Gln Gly
    290                 295                 300

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val
                340                 345                 350

Ser Leu Gln Val Ala Ala Pro Tyr Ser Lys Pro Ser Met Thr Leu Glu
    355                 360                 365

Pro Asn Lys Asp Leu Arg Pro Gly Asp Thr Val Thr Ile Thr Cys Ser
370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
                405                 410                 415

Gln Gly Leu Phe Asp Val His Ser Val Leu Arg Val Val Leu Gly Ala
                420                 425                 430

Asn Gly Thr Tyr Ser Cys Leu Val Arg Asn Pro Val Leu Gln Gln Asp
    435                 440                 445

Ala His Gly Ser Val Thr Ile Thr Gly Gln Pro Met Thr Phe Pro Pro
450                 455                 460

Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
                485                 490                 495

Glu Glu Glu Asn Ala Gly Ala Glu Asp Gln Asp Gly Glu Gly Glu Gly
                500                 505                 510

Ser Lys Thr Ala Leu Gln Pro Leu Lys His Ser Asp Ser Lys Glu Asp
    515                 520                 525

Asp Gly Gln Glu Ile Ala
    530

<210> SEQ ID NO 15
<211> LENGTH: 564
<212> TYPE: DNA
<213> ORGANISM: Homo sapiens
<220> FEATURE:
<221> NAME/KEY: CDS
<222> LOCATION: (1)..(564)

<400> SEQUENCE: 15 atg ttc aga ggc cgg aca gca gtg ttt gct gat caa gtg ata gtt ggc    48
Met Phe Arg Gly Arg Thr Ala Val Phe Ala Asp Gln Val Ile Val Gly
1               5                   10                  15
```

| | | |
|---|---|---|
| aat gcc tct ttg cgg ctg aaa aac gtg caa ctc aca gat gct ggc acc<br>Asn Ala Ser Leu Arg Leu Lys Asn Val Gln Leu Thr Asp Ala Gly Thr<br>          20                    25                    30 | | 96 |
| tac aaa tgt tat atc atc act tct aaa ggc aag ggg aat gct aac ctt<br>Tyr Lys Cys Tyr Ile Ile Thr Ser Lys Gly Lys Gly Asn Ala Asn Leu<br>              35                    40                    45 | | 144 |
| gag tat aaa act gga gcc ttc agc atg ccg gaa gtg aat gtg gac tat<br>Glu Tyr Lys Thr Gly Ala Phe Ser Met Pro Glu Val Asn Val Asp Tyr<br>50                          55                        60 | | 192 |
| aat gcc agc tca gag acc ttg cgg tgt gag gct ccc cga tgg ttc ccc<br>Asn Ala Ser Ser Glu Thr Leu Arg Cys Glu Ala Pro Arg Trp Phe Pro<br>65                    70                    75                    80 | | 240 |
| cag ccc aca gtg gtc tgg gca tcc caa gtt gac cag gga gcc aac ttc<br>Gln Pro Thr Val Val Trp Ala Ser Gln Val Asp Gln Gly Ala Asn Phe<br>                    85                    90                    95 | | 288 |
| tcg gaa gtc tcc aat acc agc ttt gag ctg aac tct gag aat gtg acc<br>Ser Glu Val Ser Asn Thr Ser Phe Glu Leu Asn Ser Glu Asn Val Thr<br>                  100                 105                110 | | 336 |
| atg aag gtt gtg tct gtg ctc tac aat gtt acg atc aac aac aca tac<br>Met Lys Val Val Ser Val Leu Tyr Asn Val Thr Ile Asn Asn Thr Tyr<br>            115                  120                 125 | | 384 |
| tcc tgt atg att gaa aat gac att gcc aaa gca aca ggg gat atc aaa<br>Ser Cys Met Ile Glu Asn Asp Ile Ala Lys Ala Thr Gly Asp Ile Lys<br>130                       135                        140 | | 432 |
| gtg aca gaa tcg gag atc aaa agg cgg agt cac cta cag ctg cta aac<br>Val Thr Glu Ser Glu Ile Lys Arg Arg Ser His Leu Gln Leu Leu Asn<br>145                       150                     155                160 | | 480 |
| tca aag gct tct ctg tgt gtc tct tct ttc ttt gcc atc agc tgg gca<br>Ser Lys Ala Ser Leu Cys Val Ser Ser Phe Phe Ala Ile Ser Trp Ala<br>                  165                 170                175 | | 528 |
| ctt ctg cct ctc agc cct tac ctg atg cta aaa taa<br>Leu Leu Pro Leu Ser Pro Tyr Leu Met Leu Lys<br>          180                    185 | | 564 |

<210> SEQ ID NO 16
<211> LENGTH: 187
<212> TYPE: PRT
<213> ORGANISM: Homo sapiens

<400> SEQUENCE: 16

Met Phe Arg Gly Arg Thr Ala Val Phe Ala Asp Gln Val Ile Val Gly
1               5                   10                  15

Asn Ala Ser Leu Arg Leu Lys Asn Val Gln Leu Thr Asp Ala Gly Thr
            20                  25                  30

Tyr Lys Cys Tyr Ile Ile Thr Ser Lys Gly Lys Gly Asn Ala Asn Leu
        35                  40                  45

Glu Tyr Lys Thr Gly Ala Phe Ser Met Pro Glu Val Asn Val Asp Tyr
    50                  55                  60

Asn Ala Ser Ser Glu Thr Leu Arg Cys Glu Ala Pro Arg Trp Phe Pro
65                  70                  75                  80

Gln Pro Thr Val Val Trp Ala Ser Gln Val Asp Gln Gly Ala Asn Phe
                85                  90                  95

Ser Glu Val Ser Asn Thr Ser Phe Glu Leu Asn Ser Glu Asn Val Thr
            100                 105                 110

Met Lys Val Val Ser Val Leu Tyr Asn Val Thr Ile Asn Asn Thr Tyr
        115                 120                 125

Ser Cys Met Ile Glu Asn Asp Ile Ala Lys Ala Thr Gly Asp Ile Lys
    130                 135                 140

Val Thr Glu Ser Glu Ile Lys Arg Arg Ser His Leu Gln Leu Leu Asn
145                 150                 155                 160

Ser Lys Ala Ser Leu Cys Val Ser Ser Phe Phe Ala Ile Ser Trp Ala
            165                 170                 175

Leu Leu Pro Leu Ser Pro Tyr Leu Met Leu Lys
        180                 185

<210> SEQ ID NO 17
<211> LENGTH: 936
<212> TYPE: DNA
<213> ORGANISM: Homo sapiens
<220> FEATURE:
<221> NAME/KEY: CDS
<222> LOCATION: (1)..(936)

<400> SEQUENCE: 17

| | | | | | | | | | | | | | | | | |
|---|---|---|---|---|---|---|---|---|---|---|---|---|---|---|---|---|
| atg | ggc | gtc | ccc | acg | gcc | ctg | gag | gcc | ggc | agc | tgg | cgc | tgg | gga | tcc | 48 |
| Met | Gly | Val | Pro | Thr | Ala | Leu | Glu | Ala | Gly | Ser | Trp | Arg | Trp | Gly | Ser | |
| 1 | | | | 5 | | | | | 10 | | | | | 15 | | |
| ctg | ctc | ttc | gct | ctc | ttc | ctg | gct | gcg | tcc | cta | ggt | ccg | gtg | gca | gcc | 96 |
| Leu | Leu | Phe | Ala | Leu | Phe | Leu | Ala | Ala | Ser | Leu | Gly | Pro | Val | Ala | Ala | |
| | | | 20 | | | | | 25 | | | | | 30 | | | |
| ttc | aag | gtc | gcc | acg | ccg | tat | tcc | ctg | tat | gtc | tgt | ccc | gag | ggg | cag | 144 |
| Phe | Lys | Val | Ala | Thr | Pro | Tyr | Ser | Leu | Tyr | Val | Cys | Pro | Glu | Gly | Gln | |
| | | 35 | | | | | 40 | | | | | 45 | | | | |
| aac | gtc | acc | ctc | acc | tgc | agg | ctc | ttg | ggc | cct | gtg | gac | aaa | ggg | cac | 192 |
| Asn | Val | Thr | Leu | Thr | Cys | Arg | Leu | Leu | Gly | Pro | Val | Asp | Lys | Gly | His | |
| | 50 | | | | | 55 | | | | | 60 | | | | | |
| gat | gtg | acc | ttc | tac | aag | acg | tgg | tac | cgc | agc | tcg | agg | ggc | gag | gtg | 240 |
| Asp | Val | Thr | Phe | Tyr | Lys | Thr | Trp | Tyr | Arg | Ser | Ser | Arg | Gly | Glu | Val | |
| 65 | | | | | 70 | | | | | 75 | | | | | 80 | |
| cag | acc | tgc | tca | gag | cgc | cgg | ccc | atc | cgc | aac | ctc | acg | ttc | cag | gac | 288 |
| Gln | Thr | Cys | Ser | Glu | Arg | Arg | Pro | Ile | Arg | Asn | Leu | Thr | Phe | Gln | Asp | |
| | | | | 85 | | | | | 90 | | | | | 95 | | |
| ctt | cac | ctg | cac | cat | gga | ggc | cac | cag | gct | gcc | aac | acc | agc | cac | gac | 336 |
| Leu | His | Leu | His | His | Gly | Gly | His | Gln | Ala | Ala | Asn | Thr | Ser | His | Asp | |
| | | | 100 | | | | | 105 | | | | | 110 | | | |
| ctg | gct | cag | cgc | cac | ggg | ctg | gag | tcg | gcc | tcc | gac | cac | cat | ggc | aac | 384 |
| Leu | Ala | Gln | Arg | His | Gly | Leu | Glu | Ser | Ala | Ser | Asp | His | His | Gly | Asn | |
| | | 115 | | | | | 120 | | | | | 125 | | | | |
| ttc | tcc | atc | acc | atg | cgc | aac | ctg | acc | ctg | ctg | gat | agc | ggc | ctc | tac | 432 |
| Phe | Ser | Ile | Thr | Met | Arg | Asn | Leu | Thr | Leu | Leu | Asp | Ser | Gly | Leu | Tyr | |
| | 130 | | | | | 135 | | | | | 140 | | | | | |
| tgc | tgc | ctg | gtg | gtg | gag | atc | agg | cac | cac | cac | tcg | gag | cac | agg | gtc | 480 |
| Cys | Cys | Leu | Val | Val | Glu | Ile | Arg | His | His | His | Ser | Glu | His | Arg | Val | |
| 145 | | | | | 150 | | | | | 155 | | | | | 160 | |
| cat | ggt | gcc | atg | gag | ctg | cag | gtg | cag | aca | ggc | aaa | gat | gca | cca | tcc | 528 |
| His | Gly | Ala | Met | Glu | Leu | Gln | Val | Gln | Thr | Gly | Lys | Asp | Ala | Pro | Ser | |
| | | | | 165 | | | | | 170 | | | | | 175 | | |
| aac | tgt | gtg | gtg | tac | cca | tcc | tcc | cag | gat | agt | gaa | aac | atc | acg | | 576 |
| Asn | Cys | Val | Val | Tyr | Pro | Ser | Ser | Gln | Asp | Ser | Glu | Asn | Ile | Thr | | |
| | | | 180 | | | | | 185 | | | | | 190 | | | |
| gct | gca | gcc | ctg | gct | acg | ggt | gcc | tgc | atc | gta | gga | atc | ctc | tgc | ctc | 624 |
| Ala | Ala | Ala | Leu | Ala | Thr | Gly | Ala | Cys | Ile | Val | Gly | Ile | Leu | Cys | Leu | |
| | | 195 | | | | | 200 | | | | | 205 | | | | |
| ccc | ctc | atc | ctg | ctc | ctg | gtc | tac | aag | caa | agg | cag | gca | gcc | tcc | aac | 672 |
| Pro | Leu | Ile | Leu | Leu | Leu | Val | Tyr | Lys | Gln | Arg | Gln | Ala | Ala | Ser | Asn | |
| | 210 | | | | | 215 | | | | | 220 | | | | | |
| cgc | cgt | gcc | cag | gag | ctg | gtg | cgg | atg | gac | agc | aac | att | caa | ggg | att | 720 |
| Arg | Arg | Ala | Gln | Glu | Leu | Val | Arg | Met | Asp | Ser | Asn | Ile | Gln | Gly | Ile | |
| 225 | | | | | 230 | | | | | 235 | | | | | 240 | |

```
gaa aac ccc ggc ttt gaa gcc tca cca cct gcc cag ggg ata ccc gag      768
Glu Asn Pro Gly Phe Glu Ala Ser Pro Pro Ala Gln Gly Ile Pro Glu
            245                 250                 255 gcc aaa gtc agg cac ccc ctg tcc tat gtg gcc cag cgg cag cct tct      816
Ala Lys Val Arg His Pro Leu Ser Tyr Val Ala Gln Arg Gln Pro Ser
        260                 265                 270 gag tct ggg cgg cat ctg ctt tcg gag ccc agc acc ccc ctg tct cct      864
Glu Ser Gly Arg His Leu Leu Ser Glu Pro Ser Thr Pro Leu Ser Pro
    275                 280                 285 cca ggc ccc gga gac gtc ttc ttc cca tcc ctg gac cct gtc cct gac      912
Pro Gly Pro Gly Asp Val Phe Phe Pro Ser Leu Asp Pro Val Pro Asp
290                 295                 300 tct cca aac ttt gag gtc atc tag                                      936
Ser Pro Asn Phe Glu Val Ile
305                 310

<210> SEQ ID NO 18
<211> LENGTH: 311
<212> TYPE: PRT
<213> ORGANISM: Homo sapiens

<400> SEQUENCE: 18

Met Gly Val Pro Thr Ala Leu Glu Ala Gly Ser Trp Arg Trp Gly Ser
1               5                   10                  15

Leu Leu Phe Ala Leu Phe Leu Ala Ala Ser Leu Gly Pro Val Ala Ala
            20                  25                  30

Phe Lys Val Ala Thr Pro Tyr Ser Leu Tyr Val Cys Pro Glu Gly Gln
        35                  40                  45

Asn Val Thr Leu Thr Cys Arg Leu Leu Gly Pro Val Asp Lys Gly His
    50                  55                  60

Asp Val Thr Phe Tyr Lys Thr Trp Tyr Arg Ser Ser Arg Gly Glu Val
65                  70                  75                  80

Gln Thr Cys Ser Glu Arg Arg Pro Ile Arg Asn Leu Thr Phe Gln Asp
                85                  90                  95

Leu His Leu His His Gly Gly His Gln Ala Ala Asn Thr Ser His Asp
            100                 105                 110

Leu Ala Gln Arg His Gly Leu Glu Ser Ala Ser Asp His His Gly Asn
        115                 120                 125

Phe Ser Ile Thr Met Arg Asn Leu Thr Leu Leu Asp Ser Gly Leu Tyr
    130                 135                 140

Cys Cys Leu Val Val Glu Ile Arg His His Ser Glu His Arg Val
145                 150                 155                 160

His Gly Ala Met Glu Leu Gln Val Gln Thr Gly Lys Asp Ala Pro Ser
                165                 170                 175

Asn Cys Val Val Tyr Pro Ser Ser Ser Gln Asp Ser Glu Asn Ile Thr
            180                 185                 190

Ala Ala Ala Leu Ala Thr Gly Ala Cys Ile Val Gly Ile Leu Cys Leu
        195                 200                 205

Pro Leu Ile Leu Leu Leu Val Tyr Lys Gln Arg Gln Ala Ala Ser Asn
    210                 215                 220

Arg Arg Ala Gln Glu Leu Val Arg Met Asp Ser Asn Ile Gln Gly Ile
225                 230                 235                 240

Glu Asn Pro Gly Phe Glu Ala Ser Pro Pro Ala Gln Gly Ile Pro Glu
                245                 250                 255

Ala Lys Val Arg His Pro Leu Ser Tyr Val Ala Gln Arg Gln Pro Ser
            260                 265                 270
```

```
Glu Ser Gly Arg His Leu Leu Ser Glu Pro Ser Thr Pro Leu Ser Pro
        275                 280                 285

Pro Gly Pro Gly Asp Val Phe Phe Pro Ser Leu Asp Pro Val Pro Asp
    290                 295                 300

Ser Pro Asn Phe Glu Val Ile
305                 310

<210> SEQ ID NO 19
<211> LENGTH: 1335
<212> TYPE: DNA
<213> ORGANISM: Homo sapiens
<220> FEATURE:
<221> NAME/KEY: CDS
<222> LOCATION: (1)..(1335)

<400> SEQUENCE: 19 atg ttg ctc atg gtc gtc agc atg gcg tgt gtt ggg ttc ttc ttg gtc        48
Met Leu Leu Met Val Val Ser Met Ala Cys Val Gly Phe Phe Leu Val
1               5                   10                  15 cag agg gcc ggt cca cac gtg ggt ggt cag gac aag ccc ttc ctg tct        96
Gln Arg Ala Gly Pro His Val Gly Gly Gln Asp Lys Pro Phe Leu Ser
            20                  25                  30 gcc tgg ccc agc gct gtg gtg cct cga gga gga cac gtg act ctt cgg       144
Ala Trp Pro Ser Ala Val Val Pro Arg Gly Gly His Val Thr Leu Arg
        35                  40                  45 tgt cac tat cgt cat agg ttt aac aat ttc atg cta tac aaa gaa gac       192
Cys His Tyr Arg His Arg Phe Asn Asn Phe Met Leu Tyr Lys Glu Asp
    50                  55                  60 aga atc cac gtt ccc atc ttc cat ggc aga tta ttc cag gag agc ttc       240
Arg Ile His Val Pro Ile Phe His Gly Arg Leu Phe Gln Glu Ser Phe
65                  70                  75                  80 aac atg agc cct gtg acc aca gca cat gca ggg aac tac aca tgt cgg       288
Asn Met Ser Pro Val Thr Thr Ala His Ala Gly Asn Tyr Thr Cys Arg
                85                  90                  95 ggt tca cac cca cac tcc ccc act ggg tgg tcg gca ccc agc aac ccc       336
Gly Ser His Pro His Ser Pro Thr Gly Trp Ser Ala Pro Ser Asn Pro
            100                 105                 110 gtg gtg atc atg gtc aca gga aac cac aga aaa cct tcc ctc ctg gcc       384
Val Val Ile Met Val Thr Gly Asn His Arg Lys Pro Ser Leu Leu Ala
        115                 120                 125 cac cca ggt ccc ctg gtg aaa tca gga gag aga gtc atc ctg caa tgt       432
His Pro Gly Pro Leu Val Lys Ser Gly Glu Arg Val Ile Leu Gln Cys
    130                 135                 140 tgg tca gat atc atg ttt gag cac ttc ttt ctg cac aaa gag ggg atc       480
Trp Ser Asp Ile Met Phe Glu His Phe Phe Leu His Lys Glu Gly Ile
145                 150                 155                 160 tct aag gac ccc tca cgc ctc gtt gga cag atc cat gat ggg gtc tcc       528
Ser Lys Asp Pro Ser Arg Leu Val Gly Gln Ile His Asp Gly Val Ser
                165                 170                 175 aag gcc aat ttc tcc atc ggt ccc atg atg ctt gcc ctt gca ggg acc       576
Lys Ala Asn Phe Ser Ile Gly Pro Met Met Leu Ala Leu Ala Gly Thr
            180                 185                 190 tac aga tgc tac ggt tct gtt act cac acc ccc tat cag ttg tca gct       624
Tyr Arg Cys Tyr Gly Ser Val Thr His Thr Pro Tyr Gln Leu Ser Ala
        195                 200                 205 ccc agt gat ccc ctg gac atc gtg gtc aca ggt cca tat gag aaa cct       672
Pro Ser Asp Pro Leu Asp Ile Val Val Thr Gly Pro Tyr Glu Lys Pro
    210                 215                 220 tct ctc tca gcc cag ccg ggc ccc aag gtt cag gca gga gag agc gtg       720
Ser Leu Ser Ala Gln Pro Gly Pro Lys Val Gln Ala Gly Glu Ser Val
225                 230                 235                 240
```

-continued

|     | 225 |     |     | 230 |     |     |     | 235 |     |     |     | 240 |     |      |
|-----|-----|-----|-----|-----|-----|-----|-----|-----|-----|-----|-----|-----|-----|------|
| acc | ttg | tcc | tgc | agc | tcc | cgg | agc | tcc | tat | gac | atg | tac | cat | cta  | tcc  | 768 |
| Thr | Leu | Ser | Cys | Ser | Ser | Arg | Ser | Ser | Tyr | Asp | Met | Tyr | His | Leu  | Ser  |     |
|     |     |     |     | 245 |     |     |     |     | 250 |     |     |     |     | 255  |      |     |

```
acc ttg tcc tgc agc tcc cgg agc tcc tat gac atg tac cat cta tcc      768
Thr Leu Ser Cys Ser Ser Arg Ser Ser Tyr Asp Met Tyr His Leu Ser
                245                 250                 255 agg gag ggg gga gcc cat gaa cgt agg ctc cct gca gtg cgc aag gtc      816
Arg Glu Gly Gly Ala His Glu Arg Arg Leu Pro Ala Val Arg Lys Val
            260                 265                 270 aac aga aca ttc cag gca gat ttc cct ctg ggc cct gcc acc cac gga      864
Asn Arg Thr Phe Gln Ala Asp Phe Pro Leu Gly Pro Ala Thr His Gly
        275                 280                 285 ggg acc tac aga tgc ttc ggc tct ttc cgt cac tct ccc tac gag tgg      912
Gly Thr Tyr Arg Cys Phe Gly Ser Phe Arg His Ser Pro Tyr Glu Trp
    290                 295                 300 tca gac ccg agt gac cca ctg ctt gtt tct gtc aca gga aac cct tca      960
Ser Asp Pro Ser Asp Pro Leu Leu Val Ser Val Thr Gly Asn Pro Ser
305                 310                 315                 320 agt agt tgg cct tca ccc aca gaa cca agc tcc aaa tct ggt aac ccc     1008
Ser Ser Trp Pro Ser Pro Thr Glu Pro Ser Ser Lys Ser Gly Asn Pro
                325                 330                 335 aga cac ctg cac att ctg att ggg acc tca gtg gtc atc atc ctc ttc     1056
Arg His Leu His Ile Leu Ile Gly Thr Ser Val Val Ile Ile Leu Phe
            340                 345                 350 atc ctc ctc ctc ttc ttt ctc ctt cat ctc tgg tgc tcc aac aaa aaa     1104
Ile Leu Leu Leu Phe Phe Leu Leu His Leu Trp Cys Ser Asn Lys Lys
        355                 360                 365 aat gct gct gta atg gac caa gag cct gca ggg aac aga aca gcc aac     1152
Asn Ala Ala Val Met Asp Gln Glu Pro Ala Gly Asn Arg Thr Ala Asn
    370                 375                 380 agc gag gac tct gat gaa caa gac cct gag gag gtg aca tac gca cag     1200
Ser Glu Asp Ser Asp Glu Gln Asp Pro Glu Glu Val Thr Tyr Ala Gln
385                 390                 395                 400 ttg gat cac tgc gtt ttc aca cag aga aaa atc act cgc cct tct cag     1248
Leu Asp His Cys Val Phe Thr Gln Arg Lys Ile Thr Arg Pro Ser Gln
                405                 410                 415 agg ccc aag aca ccc cct aca gat acc atc ttg tac acg gaa ctt cca     1296
Arg Pro Lys Thr Pro Pro Thr Asp Thr Ile Leu Tyr Thr Glu Leu Pro
            420                 425                 430 aat gct aag ccc aga tcc aaa gtt gtc tcc tgc cca tga                 1335
Asn Ala Lys Pro Arg Ser Lys Val Val Ser Cys Pro
        435                 440
```

<210> SEQ ID NO 20
<211> LENGTH: 444
<212> TYPE: PRT
<213> ORGANISM: Homo sapiens

<400> SEQUENCE: 20

```
Met Leu Leu Met Val Val Ser Met Ala Cys Val Gly Phe Phe Leu Val
1               5                   10                  15

Gln Arg Ala Gly Pro His Val Gly Gly Gln Asp Lys Pro Phe Leu Ser
            20                  25                  30

Ala Trp Pro Ser Ala Val Val Pro Arg Gly Gly His Val Thr Leu Arg
        35                  40                  45

Cys His Tyr Arg His Arg Phe Asn Asn Phe Met Leu Tyr Lys Glu Asp
    50                  55                  60

Arg Ile His Val Pro Ile Phe His Gly Arg Leu Phe Gln Glu Ser Phe
65                  70                  75                  80

Asn Met Ser Pro Val Thr Thr Ala His Ala Gly Asn Tyr Thr Cys Arg
                85                  90                  95
```

```
Gly Ser His Pro His Ser Pro Thr Gly Trp Ser Ala Pro Ser Asn Pro
            100                 105                 110

Val Val Ile Met Val Thr Gly Asn His Arg Lys Pro Ser Leu Leu Ala
        115                 120                 125

His Pro Gly Pro Leu Val Lys Ser Gly Glu Arg Val Ile Leu Gln Cys
130                 135                 140

Trp Ser Asp Ile Met Phe Glu His Phe Phe Leu His Lys Glu Gly Ile
145                 150                 155                 160

Ser Lys Asp Pro Ser Arg Leu Val Gly Gln Ile His Asp Gly Val Ser
                165                 170                 175

Lys Ala Asn Phe Ser Ile Gly Pro Met Met Leu Ala Leu Ala Gly Thr
            180                 185                 190

Tyr Arg Cys Tyr Gly Ser Val Thr His Thr Pro Tyr Gln Leu Ser Ala
        195                 200                 205

Pro Ser Asp Pro Leu Asp Ile Val Val Thr Gly Pro Tyr Glu Lys Pro
210                 215                 220

Ser Leu Ser Ala Gln Pro Gly Pro Lys Val Gln Ala Gly Glu Ser Val
225                 230                 235                 240

Thr Leu Ser Cys Ser Ser Arg Ser Ser Tyr Asp Met Tyr His Leu Ser
                245                 250                 255

Arg Glu Gly Gly Ala His Glu Arg Arg Leu Pro Ala Val Arg Lys Val
            260                 265                 270

Asn Arg Thr Phe Gln Ala Asp Phe Pro Leu Gly Pro Ala Thr His Gly
        275                 280                 285

Gly Thr Tyr Arg Cys Phe Gly Ser Phe Arg His Ser Pro Tyr Glu Trp
        290                 295                 300

Ser Asp Pro Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Asn Pro
                325                 330                 335

Arg His Leu His Ile Leu Ile Gly Thr Ser Val Val Ile Ile Leu Phe
            340                 345                 350

Ile Leu Leu Leu Phe Phe Leu Leu His Leu Trp Cys Ser Asn Lys Lys
        355                 360                 365

Asn Ala Ala Val Met Asp Gln Glu Pro Ala Gly Asn Arg Thr Ala Asn
370                 375                 380

Ser Glu Asp Ser Asp Glu Gln Asp Pro Glu Glu Val Thr Tyr Ala Gln
385                 390                 395                 400

Leu Asp His Cys Val Phe Thr Gln Arg Lys Ile Thr Arg Pro Ser Gln
                405                 410                 415

Arg Pro Lys Thr Pro Pro Thr Asp Thr Ile Leu Tyr Thr Glu Leu Pro
            420                 425                 430

Asn Ala Lys Pro Arg Ser Lys Val Val Ser Cys Pro
        435                 440
```

<210> SEQ ID NO 21
<211> LENGTH: 768
<212> TYPE: DNA
<213> ORGANISM: Homo sapiens
<220> FEATURE:
<221> NAME/KEY: CDS
<222> LOCATION: (1)..(768)

<400> SEQUENCE: 21 atg gga aac agc tgt tac aac ata gta gcc act ctg ttg ctg gtc ctc        48

```
Met Gly Asn Ser Cys Tyr Asn Ile Val Ala Thr Leu Leu Leu Val Leu
1               5                   10                  15 aac ttt gag agg aca aga tca ttg cag gat cct tgt agt aac tgc cca          96
Asn Phe Glu Arg Thr Arg Ser Leu Gln Asp Pro Cys Ser Asn Cys Pro
            20                  25                  30 gct ggt aca ttc tgt gat aat aac agg aat cag att tgc agt ccc tgt         144
Ala Gly Thr Phe Cys Asp Asn Asn Arg Asn Gln Ile Cys Ser Pro Cys
                35                  40                  45 cct cca aat agt ttc tcc agc gca ggt gga caa agg acc tgt gac ata         192
Pro Pro Asn Ser Phe Ser Ser Ala Gly Gly Gln Arg Thr Cys Asp Ile
    50                  55                  60 tgc agg cag tgt aaa ggt gtt ttc agg acc agg aag gag tgt tcc tcc         240
Cys Arg Gln Cys Lys Gly Val Phe Arg Thr Arg Lys Glu Cys Ser Ser
65                  70                  75                  80 acc agc aat gca gag tgt gac tgc act cca ggg ttt cac tgc ctg ggg         288
Thr Ser Asn Ala Glu Cys Asp Cys Thr Pro Gly Phe His Cys Leu Gly
                85                  90                  95 gca gga tgc agc atg tgt gaa cag gat tgt aaa caa ggt caa gaa ctg         336
Ala Gly Cys Ser Met Cys Glu Gln Asp Cys Lys Gln Gly Gln Glu Leu
            100                 105                 110 aca aaa aaa ggt tgt aaa gac tgt tgc ttt ggg aca ttt aac gat cag         384
Thr Lys Lys Gly Cys Lys Asp Cys Cys Phe Gly Thr Phe Asn Asp Gln
        115                 120                 125 aaa cgt ggc atc tgt cga ccc tgg aca aac tgt tct ttg gat gga aag         432
Lys Arg Gly Ile Cys Arg Pro Trp Thr Asn Cys Ser Leu Asp Gly Lys
    130                 135                 140 tct gtg ctt gtg aat ggg acg aag gag agg gac gtg gtc tgt gga cca         480
Ser Val Leu Val Asn Gly Thr Lys Glu Arg Asp Val Val Cys Gly Pro
145                 150                 155                 160 tct cca gcc gac ctc tct ccg gga gca tcc tct gtg acc ccg cct gcc         528
Ser Pro Ala Asp Leu Ser Pro Gly Ala Ser Ser Val Thr Pro Pro Ala
                165                 170                 175 cct gcg aga gag cca gga cac tct ccg cag atc atc tcc ttc ttt ctt         576
Pro Ala Arg Glu Pro Gly His Ser Pro Gln Ile Ile Ser Phe Phe Leu
            180                 185                 190 gcg ctg acg tcg act gcg ttg ctc ttc ctg ctg ttc ctc acg ctc             624
Ala Leu Thr Ser Thr Ala Leu Leu Phe Leu Leu Phe Phe Leu Thr Leu
        195                 200                 205 cgt ttc tct gtt gtt aaa cgg ggc aga aag aaa ctc ctg tat ata ttc         672
Arg Phe Ser Val Val Lys Arg Gly Arg Lys Lys Leu Leu Tyr Ile Phe
    210                 215                 220 aaa caa cca ttt atg aga cca gta caa act act caa gag gaa gat ggc         720
Lys Gln Pro Phe Met Arg Pro Val Gln Thr Thr Gln Glu Glu Asp Gly
225                 230                 235                 240 tgt agc tgc cga ttt cca gaa gaa gaa gaa gga gga tgt gaa ctg tga         768
Cys Ser Cys Arg Phe Pro Glu Glu Glu Glu Gly Gly Cys Glu Leu
                245                 250                 255

<210> SEQ ID NO 22
<211> LENGTH: 255
<212> TYPE: PRT
<213> ORGANISM: Homo sapiens

<400> SEQUENCE: 22

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45
```

```
Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
                100                 105                 110

Thr Lys Lys Gly Cys Lys Asp Cys Cys Phe Gly Thr Phe Asn Asp Gln
                115                 120                 125

Lys Arg Gly Ile Cys Arg Pro Trp Thr Asn Cys Ser Leu Asp Gly Lys
                130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
                180                 185                 190

Ala Leu Thr Ser Thr Ala Leu Leu Phe Leu Leu Phe Phe Leu Thr Leu
                195                 200                 205

Arg Phe Ser Val Val Lys Arg Gly Arg Lys Lys Leu Leu Tyr Ile Phe
210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 23
<211> LENGTH: 1578
<212> TYPE: DNA
<213> ORGANISM: Homo sapiens
<220> FEATURE:
<221> NAME/KEY: CDS
<222> LOCATION: (1)..(1578)

<400> SEQUENCE: 23 atg tgg gag gct cag ttc ctg ggc ttg ctg ttt ctg cag ccg ctt tgg    48
Met Trp Glu Ala Gln Phe Leu Gly Leu Leu Phe Leu Gln Pro Leu Trp
1               5                   10                  15 gtg gct cca gtg aag cct ctc cag cca ggg gct gag gtc ccg gtg gtg    96
Val Ala Pro Val Lys Pro Leu Gln Pro Gly Ala Glu Val Pro Val Val
            20                  25                  30 tgg gcc cag gag ggg gct cct gcc cag ctc ccc tgc agc ccc aca atc   144
Trp Ala Gln Glu Gly Ala Pro Ala Gln Leu Pro Cys Ser Pro Thr Ile
        35                  40                  45 ccc ctc cag gat ctc agc ctt ctg cga aga gca ggg gtc act tgg cag   192
Pro Leu Gln Asp Leu Ser Leu Leu Arg Arg Ala Gly Val Thr Trp Gln
    50                  55                  60 cat cag cca gac agt ggc ccg ccc gct gcc gcc ccc ggc cat ccc ctg   240
His Gln Pro Asp Ser Gly Pro Pro Ala Ala Ala Pro Gly His Pro Leu
65                  70                  75                  80 gcc ccc ggc cct cac ccg gcg gcg ccc tcc tcc tgg ggg ccc agg ccc   288
Ala Pro Gly Pro His Pro Ala Ala Pro Ser Ser Trp Gly Pro Arg Pro
                85                  90                  95 cgc cgc tac acg gtg ctg agc gtg ggt ccc gga ggc ctg cgc agc ggg   336
Arg Arg Tyr Thr Val Leu Ser Val Gly Pro Gly Gly Leu Arg Ser Gly
            100                 105                 110
```

-continued

| | |
|---|---|
| agg ctg ccc ctg cag ccc cgc gtc cag ctg gat gag cgc ggc cgg cag<br>Arg Leu Pro Leu Gln Pro Arg Val Gln Leu Asp Glu Arg Gly Arg Gln<br>        115                      120                    125 | 384 |
| cgc ggg gac ttc tcg cta tgg ctg cgc cca gcc cgg cgc gcg gac gcc<br>Arg Gly Asp Phe Ser Leu Trp Leu Arg Pro Ala Arg Arg Ala Asp Ala<br>130                      135                      140 | 432 |
| ggc gag tac cgc gcc gcg gtg cac ctc agg gac cgc gcc ctc tcc tgc<br>Gly Glu Tyr Arg Ala Ala Val His Leu Arg Asp Arg Ala Leu Ser Cys<br>145                      150                    155                    160 | 480 |
| cgc ctc cgt ctg cgc ctg ggc cag gcc tcg atg act gcc agc ccc cca<br>Arg Leu Arg Leu Arg Leu Gly Gln Ala Ser Met Thr Ala Ser Pro Pro<br>        165                      170                    175 | 528 |
| gga tct ctc aga gcc tcc gac tgg gtc att ttg aac tgc tcc ttc agc<br>Gly Ser Leu Arg Ala Ser Asp Trp Val Ile Leu Asn Cys Ser Phe Ser<br>            180                      185                    190 | 576 |
| cgc cct gac cgc cca gcc tct gtg cat tgg ttc cgg aac cgg ggc cag<br>Arg Pro Asp Arg Pro Ala Ser Val His Trp Phe Arg Asn Arg Gly Gln<br>                195                      200                    205 | 624 |
| ggc cga gtc cct gtc cgg gag tcc ccc cat cac cac tta gcg gaa agc<br>Gly Arg Val Pro Val Arg Glu Ser Pro His His His Leu Ala Glu Ser<br>210                      215                    220 | 672 |
| ttc ctc ttc ctg ccc caa gtc agc ccc atg gac tct ggg ccc tgg ggc<br>Phe Leu Phe Leu Pro Gln Val Ser Pro Met Asp Ser Gly Pro Trp Gly<br>225                      230                    235                    240 | 720 |
| tgc atc ctc acc tac aga gat ggc ttc aac gtc tcc atc atg tat aac<br>Cys Ile Leu Thr Tyr Arg Asp Gly Phe Asn Val Ser Ile Met Tyr Asn<br>                        245                      250                    255 | 768 |
| ctc act gtt ctg ggt ctg gag ccc cca act ccc ttg aca gtg tac gct<br>Leu Thr Val Leu Gly Leu Glu Pro Pro Thr Pro Leu Thr Val Tyr Ala<br>              260                      265                    270 | 816 |
| gga gca ggt tcc agg gtg ggg ctg ccc tgc cgc ctg cct gct ggt gtg<br>Gly Ala Gly Ser Arg Val Gly Leu Pro Cys Arg Leu Pro Ala Gly Val<br>                  275                      280                    285 | 864 |
| ggg acc cgg tct ttc ctc act gcc aag tgg act cct cct ggg gga ggc<br>Gly Thr Arg Ser Phe Leu Thr Ala Lys Trp Thr Pro Pro Gly Gly Gly<br>290                      295                    300 | 912 |
| cct gac ctc ctg gtg act gga gac aat ggc gac ttt acc ctt cga cta<br>Pro Asp Leu Leu Val Thr Gly Asp Asn Gly Asp Phe Thr Leu Arg Leu<br>305                      310                    315                    320 | 960 |
| gag gat gtg agc cag gcc cag gct ggg acc tac acc tgc cat atc cat<br>Glu Asp Val Ser Gln Ala Gln Ala Gly Thr Tyr Thr Cys His Ile His<br>                    325                      330                    335 | 1008 |
| ctg cag gaa cag cag ctc aat gcc act gtc aca ttg gca atc atc aca<br>Leu Gln Glu Gln Gln Leu Asn Ala Thr Val Thr Leu Ala Ile Ile Thr<br>                  340                      345                    350 | 1056 |
| gtg act ccc aaa tcc ttt ggg tca cct gga tcc ctg ggg aag ctg ctt<br>Val Thr Pro Lys Ser Phe Gly Ser Pro Gly Ser Leu Gly Lys Leu Leu<br>                    355                      360                    365 | 1104 |
| tgt gag gtg act cca gta tct gga caa gaa cgc ttt gtg tgg agc tct<br>Cys Glu Val Thr Pro Val Ser Gly Gln Glu Arg Phe Val Trp Ser Ser<br>370                      375                      380 | 1152 |
| ctg gac acc cca tcc cag agg agt ttc tca gga cct tgg ctg gag gca<br>Leu Asp Thr Pro Ser Gln Arg Ser Phe Ser Gly Pro Trp Leu Glu Ala<br>385                      390                    395                    400 | 1200 |
| cag gag gcc cag ctc ctt tcc cag cct tgg caa tgc cag ctg tac cag<br>Gln Glu Ala Gln Leu Leu Ser Gln Pro Trp Gln Cys Gln Leu Tyr Gln<br>                    405                      410                    415 | 1248 |
| ggg gag agg ctt ctt gga gca gca gtg tac ttc aca gag ctg tct agc<br>Gly Glu Arg Leu Leu Gly Ala Ala Val Tyr Phe Thr Glu Leu Ser Ser<br>                  420                      425                    430 | 1296 |

```
cca ggt gcc caa cgc tct ggg aga gcc cca ggt gcc ctc cca gca ggc      1344
Pro Gly Ala Gln Arg Ser Gly Arg Ala Pro Gly Ala Leu Pro Ala Gly
        435                 440                 445 cac ctc ctg ctg ttt ctc atc ctt ggt gtc ctt tct ctg ctc ctt ttg      1392
His Leu Leu Leu Phe Leu Ile Leu Gly Val Leu Ser Leu Leu Leu Leu
450                 455                 460 gtg act gga gcc ttt ggc ttt cac ctt tgg aga aga cag tgg cga cca      1440
Val Thr Gly Ala Phe Gly Phe His Leu Trp Arg Arg Gln Trp Arg Pro
465                 470                 475                 480 aga cga ttt tct gcc tta gag caa ggg att cac cct ccg cag gct cag      1488
Arg Arg Phe Ser Ala Leu Glu Gln Gly Ile His Pro Pro Gln Ala Gln
                485                 490                 495 agc aag ata gag gag ctg gag caa gaa ccg gag ccg gag ccg gag ccg      1536
Ser Lys Ile Glu Glu Leu Glu Gln Glu Pro Glu Pro Glu Pro Glu Pro
            500                 505                 510 gaa ccg gag ccc gag ccc gag ccc gag ccg gag cag ctc tga              1578
Glu Pro Glu Pro Glu Pro Glu Pro Glu Pro Glu Gln Leu
        515                 520                 525
```

<210> SEQ ID NO 24
<211> LENGTH: 525
<212> TYPE: PRT
<213> ORGANISM: Homo sapiens

<400> SEQUENCE: 24

```
Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
```

```
                    245                 250                 255
Leu Thr Val Leu Gly Leu Glu Pro Pro Thr Pro Leu Thr Val Tyr Ala
                260                 265                 270

Gly Ala Gly Ser Arg Val Gly Leu Pro Cys Arg Leu Pro Ala Gly Val
            275                 280                 285

Gly Thr Arg Ser Phe Leu Thr Ala Lys Trp Thr Pro Gly Gly Gly
        290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Leu Phe Leu Ile Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Pro Glu Gln Leu
        515                 520                 525

<210> SEQ ID NO 25
<211> LENGTH: 906
<212> TYPE: DNA
<213> ORGANISM: Homo sapiens
<220> FEATURE:
<221> NAME/KEY: CDS
<222> LOCATION: (1)..(906)

<400> SEQUENCE: 25 atg ttt tca cat ctt ccc ttt gac tgt gtc ctg ctg ctg ctg ctg cta    48
Met Phe Ser His Leu Pro Phe Asp Cys Val Leu Leu Leu Leu Leu Leu
1               5                   10                  15 cta ctt aca agg tcc tca gaa gtg gaa tac aga gcg gag gtc ggt cag    96
Leu Leu Thr Arg Ser Ser Glu Val Glu Tyr Arg Ala Glu Val Gly Gln
            20                  25                  30 aat gcc tat ctg ccc tgc ttc tac acc cca gcc gcc cca ggg aac ctc   144
Asn Ala Tyr Leu Pro Cys Phe Tyr Thr Pro Ala Ala Pro Gly Asn Leu
        35                  40                  45 gtg ccc gtc tgc tgg ggc aaa gga gcc tgt cct gtg ttt gaa tgt ggc   192
Val Pro Val Cys Trp Gly Lys Gly Ala Cys Pro Val Phe Glu Cys Gly
    50                  55                  60
```

| | | | | | | | | | | | | | | | | |
|---|---|---|---|---|---|---|---|---|---|---|---|---|---|---|---|---|
| aac | gtg | gtg | ctc | agg | act | gat | gaa | agg | gat | gtg | aat | tat | tgg | aca | tcc | 240 |
| Asn<br>65 | Val | Val | Leu | Arg | Thr<br>70 | Asp | Glu | Arg | Asp | Val<br>75 | Asn | Tyr | Trp | Thr | Ser<br>80 | |
| aga | tac | tgg | cta | aat | ggg | gat | ttc | cgc | aaa | gga | gat | gtg | tcc | ctg | acc | 288 |
| Arg | Tyr | Trp | Leu | Asn<br>85 | Gly | Asp | Phe | Arg | Lys<br>90 | Gly | Asp | Val | Ser | Leu<br>95 | Thr | |
| ata | gag | aat | gtg | act | cta | gca | gac | agt | ggg | atc | tac | tgc | tgc | cgg | atc | 336 |
| Ile | Glu | Asn | Val<br>100 | Thr | Leu | Ala | Asp | Ser<br>105 | Gly | Ile | Tyr | Cys | Cys<br>110 | Arg | Ile | |
| caa | atc | cca | ggc | ata | atg | aat | gat | gaa | aaa | ttt | aac | ctg | aag | ttg | gtc | 384 |
| Gln | Ile | Pro | Gly<br>115 | Ile | Met | Asn | Asp | Glu<br>120 | Lys | Phe | Asn | Leu | Lys<br>125 | Leu | Val | |
| atc | aaa | cca | gcc | aag | gtc | acc | cct | gca | ccg | act | cgg | cag | aga | gac | ttc | 432 |
| Ile | Lys | Pro<br>130 | Ala | Lys | Val | Thr | Pro<br>135 | Ala | Pro | Thr | Arg | Gln<br>140 | Arg | Asp | Phe | |
| act | gca | gcc | ttt | cca | agg | atg | ctt | acc | acc | agg | gga | cat | ggc | cca | gca | 480 |
| Thr<br>145 | Ala | Ala | Phe | Pro | Arg<br>150 | Met | Leu | Thr | Thr | Arg<br>155 | Gly | His | Gly | Pro | Ala<br>160 | |
| gag | aca | cag | aca | ctg | ggg | agc | ctc | cct | gat | ata | aat | cta | aca | caa | ata | 528 |
| Glu | Thr | Gln | Thr | Leu<br>165 | Gly | Ser | Leu | Pro | Asp<br>170 | Ile | Asn | Leu | Thr | Gln<br>175 | Ile | |
| tcc | aca | ttg | gcc | aat | gag | tta | cgg | gac | tct | aga | ttg | gcc | aat | gac | tta | 576 |
| Ser | Thr | Leu | Ala | Asn<br>180 | Glu | Leu | Arg | Asp | Ser<br>185 | Arg | Leu | Ala | Asn | Asp<br>190 | Leu | |
| cgg | gac | tct | gga | gca | acc | atc | aga | ata | ggc | atc | tac | atc | gga | gca | ggg | 624 |
| Arg | Asp | Ser<br>195 | Gly | Ala | Thr | Ile | Arg<br>200 | Ile | Gly | Ile | Tyr | Ile<br>205 | Gly | Ala | Gly | |
| atc | tgt | gct | ggg | ctg | gct | ctg | gct | ctt | atc | ttc | ggc | gct | tta | att | ttc | 672 |
| Ile | Cys<br>210 | Ala | Gly | Leu | Ala | Leu<br>215 | Ala | Leu | Ile | Phe | Gly<br>220 | Ala | Leu | Ile | Phe | |
| aaa | tgg | tat | tct | cat | agc | aaa | gag | aag | ata | cag | aat | tta | agc | ctc | atc | 720 |
| Lys<br>225 | Trp | Tyr | Ser | His | Ser<br>230 | Lys | Glu | Lys | Ile | Gln<br>235 | Asn | Leu | Ser | Leu | Ile<br>240 | |
| tct | ttg | gcc | aac | ctc | cct | ccc | tca | gga | ttg | gca | aat | gca | gta | gca | gag | 768 |
| Ser | Leu | Ala | Asn | Leu<br>245 | Pro | Pro | Ser | Gly | Leu<br>250 | Ala | Asn | Ala | Val | Ala<br>255 | Glu | |
| gga | att | cgc | tca | gaa | gaa | aac | atc | tat | acc | att | gaa | gag | aac | gta | tat | 816 |
| Gly | Ile | Arg | Ser | Glu<br>260 | Glu | Asn | Ile | Tyr | Thr<br>265 | Ile | Glu | Glu | Asn | Val<br>270 | Tyr | |
| gaa | gtg | gag | gag | ccc | aat | gag | tat | tat | tgc | tat | gtc | agc | agc | agg | cag | 864 |
| Glu | Val | Glu | Glu<br>275 | Pro | Asn | Glu | Tyr | Tyr<br>280 | Cys | Tyr | Val | Ser | Ser<br>285 | Arg | Gln | |
| caa | ccc | tca | caa | cct | ttg | ggt | tgt | cgc | ttt | gca | atg | cca | tag | | | 906 |
| Gln | Pro | Ser<br>290 | Gln | Pro | Leu | Gly | Cys<br>295 | Arg | Phe | Ala | Met | Pro<br>300 | | | | |

<210> SEQ ID NO 26
<211> LENGTH: 301
<212> TYPE: PRT
<213> ORGANISM: Homo sapiens

<400> SEQUENCE: 26

Met Phe Ser His Leu Pro Phe Asp Cys Val Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly

```
                    50                  55                  60
Asn Val Leu Arg Thr Asp Glu Arg Asp Val Asn Tyr Trp Thr Ser
 65                  70                  75                  80

Arg Tyr Trp Leu Asn Gly Asp Phe Arg Lys Gly Asp Val Ser Leu Thr
                 85                  90                  95

Ile Glu Asn Val Thr Leu Ala Asp Ser Gly Ile Tyr Cys Cys Arg Ile
                100                 105                 110

Gln Ile Pro Gly Ile Met Asn Asp Glu Lys Phe Asn Leu Lys Leu Val
                115                 120                 125

Ile Lys Pro Ala Lys Val Thr Pro Ala Pro Thr Arg Gln Arg Asp Phe
130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
                180                 185                 190

Arg Asp Ser Gly Ala Thr Ile Arg Ile Gly Ile Tyr Ile Gly Ala Gly
                195                 200                 205

Ile Cys Ala Gly Leu Ala Leu Ala Leu Ile Phe Gly Ala Leu Ile Phe
210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
                260                 265                 270

Glu Val Glu Glu Pro Asn Glu Tyr Tyr Cys Tyr Val Ser Ser Arg Gln
                275                 280                 285

Gln Pro Ser Gln Pro Leu Gly Cys Arg Phe Ala Met Pro
                290                 295                 300

<210> SEQ ID NO 27
<211> LENGTH: 735
<212> TYPE: DNA
<213> ORGANISM: Homo sapiens
<220> FEATURE:
<221> NAME/KEY: CDS
<222> LOCATION: (1)..(735)

<400> SEQUENCE: 27 atg cgc tgg tgt ctc ctc ctg atc tgg gcc cag ggg ctg agg cag gct       48
Met Arg Trp Cys Leu Leu Leu Ile Trp Ala Gln Gly Leu Arg Gln Ala
 1               5                  10                  15 ccc ctc gcc tca gga atg atg aca ggc aca ata gaa aca acg ggg aac       96
Pro Leu Ala Ser Gly Met Met Thr Gly Thr Ile Glu Thr Thr Gly Asn
             20                  25                  30 att tct gca gag aaa ggt ggc tct atc atc tta caa tgt cac ctc tcc      144
Ile Ser Ala Glu Lys Gly Gly Ser Ile Ile Leu Gln Cys His Leu Ser
         35                  40                  45 tcc acc acg gca caa gtg acc cag gtc aac tgg gag cag cag gac cag      192
Ser Thr Thr Ala Gln Val Thr Gln Val Asn Trp Glu Gln Gln Asp Gln
     50                  55                  60 ctt ctg gcc att tgt aat gct gac ttg ggg tgg cac atc tcc cca tcc      240
Leu Leu Ala Ile Cys Asn Ala Asp Leu Gly Trp His Ile Ser Pro Ser
 65                  70                  75                  80 ttc aag gat cga gtg gcc cca ggt ccc ggc ctg ggc ctc acc ctc cag      288
Phe Lys Asp Arg Val Ala Pro Gly Pro Gly Leu Gly Leu Thr Leu Gln
```

```
              Phe Lys Asp Arg Val Ala Pro Gly Pro Gly Leu Gly Leu Thr Leu Gln
                              85                  90                  95 tcg ctg acc gtg aac gat aca ggg gag tac ttc tgc atc tat cac acc            336
Ser Leu Thr Val Asn Asp Thr Gly Glu Tyr Phe Cys Ile Tyr His Thr
            100                 105                 110 tac cct gat ggg acg tac act ggg aga atc ttc ctg gag gtc cta gaa            384
Tyr Pro Asp Gly Thr Tyr Thr Gly Arg Ile Phe Leu Glu Val Leu Glu
        115                 120                 125 agc tca gtg gct gag cac ggt gcc agg ttc cag att cca ttg ctt gga            432
Ser Ser Val Ala Glu His Gly Ala Arg Phe Gln Ile Pro Leu Leu Gly
    130                 135                 140 gcc atg gcc gcg acg ctg gtg gtc atc tgc aca gca gtc atc gtg gtg            480
Ala Met Ala Ala Thr Leu Val Val Ile Cys Thr Ala Val Ile Val Val
145                 150                 155                 160 gtc gcg ttg act aga aag aag aaa gcc ctc aga atc cat tct gtg gaa            528
Val Ala Leu Thr Arg Lys Lys Lys Ala Leu Arg Ile His Ser Val Glu
                165                 170                 175 ggt gac ctc agg aga aaa tca gct gga cag gag gaa tgg agc ccc agt            576
Gly Asp Leu Arg Arg Lys Ser Ala Gly Gln Glu Glu Trp Ser Pro Ser
            180                 185                 190 gct ccc tca ccc cca gga agc tgt gtc cag gca gaa gct gca cct gct            624
Ala Pro Ser Pro Pro Gly Ser Cys Val Gln Ala Glu Ala Ala Pro Ala
        195                 200                 205 ggg ctc tgt gga gag cag cgg gga gag gac tgt gcc gag ctg cat gac            672
Gly Leu Cys Gly Glu Gln Arg Gly Glu Asp Cys Ala Glu Leu His Asp
    210                 215                 220 tac ttc aat gtc ctg agt tac aga agc ctg ggt aac tgc agc ttc ttc            720
Tyr Phe Asn Val Leu Ser Tyr Arg Ser Leu Gly Asn Cys Ser Phe Phe
225                 230                 235                 240 aca gag act ggt tag                                                        735
Thr Glu Thr Gly <210> SEQ ID NO 28
<211> LENGTH: 244
<212> TYPE: PRT
<213> ORGANISM: Homo sapiens

<400> SEQUENCE: 28

Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Leu Leu Gly
    130                 135                 140

Ala Met Ala Ala Thr Leu Val Val Ile Cys Thr Ala Val Ile Val Val
145                 150                 155                 160
```

```
Val Ala Leu Thr Arg Lys Lys Ala Leu Arg Ile His Ser Val Glu
            165                 170                 175

Gly Asp Leu Arg Arg Lys Ser Ala Gly Gln Glu Glu Trp Ser Pro Ser
            180                 185                 190

Ala Pro Ser Pro Pro Gly Ser Cys Val Gln Ala Glu Ala Ala Pro Ala
            195                 200                 205

Gly Leu Cys Gly Glu Gln Arg Gly Glu Asp Cys Ala Glu Leu His Asp
            210                 215                 220

Tyr Phe Asn Val Leu Ser Tyr Arg Ser Leu Gly Asn Cys Ser Phe Phe
225                 230                 235                 240

Thr Glu Thr Gly

<210> SEQ ID NO 29
<211> LENGTH: 834
<212> TYPE: DNA
<213> ORGANISM: Homo sapiens
<220> FEATURE:
<221> NAME/KEY: CDS
<222> LOCATION: (1)..(834)

<400> SEQUENCE: 29
```

| | | |
|---|---|---|
| atg tgc gtg ggg gct cgg cgg ctg ggc cgc ggg ccg tgt gcg gct ctg<br>Met Cys Val Gly Ala Arg Arg Leu Gly Arg Gly Pro Cys Ala Ala Leu<br>1               5                   10                  15 | 48 |
| ctc ctc ctg ggc ctg ggg ctg agc acc gtg acg ggg ctc cac tgt gtc<br>Leu Leu Leu Gly Leu Gly Leu Ser Thr Val Thr Gly Leu His Cys Val<br>            20                  25                  30 | 96 |
| ggg gac acc tac ccc agc aac gac cgg tgc tgc cac gag tgc agg cca<br>Gly Asp Thr Tyr Pro Ser Asn Asp Arg Cys Cys His Glu Cys Arg Pro<br>        35                  40                  45 | 144 |
| ggc aac ggg atg gtg agc cgc tgc agc cgc tcc cag aac acg gtg tgc<br>Gly Asn Gly Met Val Ser Arg Cys Ser Arg Ser Gln Asn Thr Val Cys<br>    50                  55                  60 | 192 |
| cgt ccg tgc ggg ccg ggc ttc tac aac gac gtg gtc agc tcc aag ccg<br>Arg Pro Cys Gly Pro Gly Phe Tyr Asn Asp Val Val Ser Ser Lys Pro<br>65                  70                  75                  80 | 240 |
| tgc aag ccc tgc acg tgg tgt aac ctc aga agt ggg agt gag cgg aag<br>Cys Lys Pro Cys Thr Trp Cys Asn Leu Arg Ser Gly Ser Glu Arg Lys<br>                85                  90                  95 | 288 |
| cag ctg tgc acg gcc aca cag gac aca gtc tgc cgc tgc cgg gcg ggc<br>Gln Leu Cys Thr Ala Thr Gln Asp Thr Val Cys Arg Cys Arg Ala Gly<br>            100                 105                 110 | 336 |
| acc cag ccc ctg gac agc tac aag cct gga gtt gac tgt gcc ccc tgc<br>Thr Gln Pro Leu Asp Ser Tyr Lys Pro Gly Val Asp Cys Ala Pro Cys<br>        115                 120                 125 | 384 |
| cct cca ggg cac ttc tcc cca ggc gac aac cag gcc tgc aag ccc tgg<br>Pro Pro Gly His Phe Ser Pro Gly Asp Asn Gln Ala Cys Lys Pro Trp<br>    130                 135                 140 | 432 |
| acc aac tgc acc ttg gct ggg aag cac acc ctg cag ccg gcc agc aat<br>Thr Asn Cys Thr Leu Ala Gly Lys His Thr Leu Gln Pro Ala Ser Asn<br>145                 150                 155                 160 | 480 |
| agc tcg gac gca atc tgt gag gac agg gac ccc cca gcc acg cag ccc<br>Ser Ser Asp Ala Ile Cys Glu Asp Arg Asp Pro Pro Ala Thr Gln Pro<br>                165                 170                 175 | 528 |
| cag gag acc cag ggc ccc ccg gcc agg ccc atc act gtc cag ccc act<br>Gln Glu Thr Gln Gly Pro Pro Ala Arg Pro Ile Thr Val Gln Pro Thr<br>            180                 185                 190 | 576 |
| gaa gcc tgg ccc aga acc tca cag gga ccc tcc acc cgg ccc gtg gag<br>Glu Ala Trp Pro Arg Thr Ser Gln Gly Pro Ser Thr Arg Pro Val Glu | 624 |

|  |  |  |  |  |  |  |  |  |  |  |  |  |  |  |  |
|---|---|---|---|---|---|---|---|---|---|---|---|---|---|---|---|
|  |  |  | 195 |  |  |  | 200 |  |  |  | 205 |  |  |  |  |
| gtc | ccc | ggg | ggc | cgt | gcg | gtt | gcc | gcc | atc | ctg | ggc | ctg | ggc | ctg | gtg | 672 |
| Val | Pro | Gly | Gly | Arg | Ala | Val | Ala | Ala | Ile | Leu | Gly | Leu | Gly | Leu | Val |
|  | 210 |  |  |  | 215 |  |  |  | 220 |  |  |  |  |  |  |
| ctg | ggg | ctg | ctg | ggc | ccc | ctg | gcc | atc | ctg | ctg | gcc | ctg | tac | ctg | ctc | 720 |
| Leu | Gly | Leu | Leu | Gly | Pro | Leu | Ala | Ile | Leu | Leu | Ala | Leu | Tyr | Leu | Leu |
| 225 |  |  |  |  | 230 |  |  |  |  | 235 |  |  |  |  | 240 |
| cgg | agg | gac | cag | agg | ctg | ccc | ccc | gat | gcc | cac | aag | ccc | cct | ggg | gga | 768 |
| Arg | Arg | Asp | Gln | Arg | Leu | Pro | Pro | Asp | Ala | His | Lys | Pro | Pro | Gly | Gly |
|  |  |  |  | 245 |  |  |  |  | 250 |  |  |  |  | 255 |  |
| ggc | agt | ttc | cgg | acc | ccc | atc | caa | gag | gag | cag | gcc | gac | gcc | cac | tcc | 816 |
| Gly | Ser | Phe | Arg | Thr | Pro | Ile | Gln | Glu | Glu | Gln | Ala | Asp | Ala | His | Ser |
|  |  |  | 260 |  |  |  |  | 265 |  |  |  |  | 270 |  |  |
| acc | ctg | gcc | aag | atc | tga |  |  |  |  |  |  |  |  |  |  | 834 |
| Thr | Leu | Ala | Lys | Ile |  |  |  |  |  |  |  |  |  |  |  |
|  |  |  | 275 |  |  |  |  |  |  |  |  |  |  |  |  |

<210> SEQ ID NO 30
<211> LENGTH: 277
<212> TYPE: PRT
<213> ORGANISM: Homo sapiens

<400> SEQUENCE: 30

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser

|  |  | 260 |  |  | 265 |  |  | 270 |  |

Thr Leu Ala Lys Ile
275

<210> SEQ ID NO 31
<211> LENGTH: 726
<212> TYPE: DNA
<213> ORGANISM: Homo sapiens
<220> FEATURE:
<221> NAME/KEY: CDS
<222> LOCATION: (1)..(726)

<400> SEQUENCE: 31

| atg | aag | aca | ttg | cct | gcc | atg | ctt | gga | act | ggg | aaa | tta | ttt | tgg | gtc | 48 |
| Met | Lys | Thr | Leu | Pro | Ala | Met | Leu | Gly | Thr | Gly | Lys | Leu | Phe | Trp | Val |  |
| 1 |  |  |  | 5 |  |  |  |  | 10 |  |  |  |  | 15 |  |  |

| ttc | ttc | tta | atc | cca | tat | ctg | gac | atc | tgg | aac | atc | cat | ggg | aaa | gaa | 96 |
| Phe | Phe | Leu | Ile | Pro | Tyr | Leu | Asp | Ile | Trp | Asn | Ile | His | Gly | Lys | Glu |  |
|  |  |  | 20 |  |  |  |  | 25 |  |  |  |  | 30 |  |  |  |

| tca | tgt | gat | gta | cag | ctt | tat | ata | aag | aga | caa | tct | gaa | cac | tcc | atc | 144 |
| Ser | Cys | Asp | Val | Gln | Leu | Tyr | Ile | Lys | Arg | Gln | Ser | Glu | His | Ser | Ile |  |
|  | 35 |  |  |  |  | 40 |  |  |  |  | 45 |  |  |  |  |  |

| tta | gca | gga | gat | ccc | ttt | gaa | cta | gaa | tgc | cct | gtg | aaa | tac | tgt | gct | 192 |
| Leu | Ala | Gly | Asp | Pro | Phe | Glu | Leu | Glu | Cys | Pro | Val | Lys | Tyr | Cys | Ala |  |
| 50 |  |  |  |  | 55 |  |  |  |  | 60 |  |  |  |  |  |  |

| aac | agg | cct | cat | gtg | act | tgg | tgc | aag | ctc | aat | gga | aca | aca | tgt | gta | 240 |
| Asn | Arg | Pro | His | Val | Thr | Trp | Cys | Lys | Leu | Asn | Gly | Thr | Thr | Cys | Val |  |
| 65 |  |  |  |  | 70 |  |  |  |  | 75 |  |  |  |  | 80 |  |

| aaa | ctt | gaa | gat | aga | caa | aca | agt | tgg | aag | gaa | gag | aag | aac | att | tca | 288 |
| Lys | Leu | Glu | Asp | Arg | Gln | Thr | Ser | Trp | Lys | Glu | Glu | Lys | Asn | Ile | Ser |  |
|  |  |  |  | 85 |  |  |  |  | 90 |  |  |  |  | 95 |  |  |

| ttt | ttc | att | cta | cat | ttt | gaa | cca | gtg | ctt | cct | aat | gac | aat | ggg | tca | 336 |
| Phe | Phe | Ile | Leu | His | Phe | Glu | Pro | Val | Leu | Pro | Asn | Asp | Asn | Gly | Ser |  |
|  |  |  | 100 |  |  |  |  | 105 |  |  |  |  | 110 |  |  |  |

| tac | cgc | tgt | tct | gca | aat | ttt | cag | tct | aat | ctc | att | gaa | agc | cac | tca | 384 |
| Tyr | Arg | Cys | Ser | Ala | Asn | Phe | Gln | Ser | Asn | Leu | Ile | Glu | Ser | His | Ser |  |
|  | 115 |  |  |  |  | 120 |  |  |  |  | 125 |  |  |  |  |  |

| aca | act | ctt | tat | gtg | aca | gga | aag | caa | aat | gaa | ctc | tct | gac | aca | gca | 432 |
| Thr | Thr | Leu | Tyr | Val | Thr | Gly | Lys | Gln | Asn | Glu | Leu | Ser | Asp | Thr | Ala |  |
| 130 |  |  |  |  | 135 |  |  |  |  | 140 |  |  |  |  |  |  |

| gga | agg | gaa | att | aac | ctg | gtt | gat | gct | cac | ctt | aag | agt | gag | caa | aca | 480 |
| Gly | Arg | Glu | Ile | Asn | Leu | Val | Asp | Ala | His | Leu | Lys | Ser | Glu | Gln | Thr |  |
| 145 |  |  |  |  | 150 |  |  |  |  | 155 |  |  |  |  | 160 |  |

| gaa | gca | agc | acc | agg | caa | aat | tcc | caa | gta | ctg | cta | tca | gaa | act | gga | 528 |
| Glu | Ala | Ser | Thr | Arg | Gln | Asn | Ser | Gln | Val | Leu | Leu | Ser | Glu | Thr | Gly |  |
|  |  |  |  | 165 |  |  |  |  | 170 |  |  |  |  | 175 |  |  |

| att | tat | gat | aat | gac | cct | gac | ctt | tgt | ttc | agg | atg | cag | gaa | ggg | tct | 576 |
| Ile | Tyr | Asp | Asn | Asp | Pro | Asp | Leu | Cys | Phe | Arg | Met | Gln | Glu | Gly | Ser |  |
|  |  |  | 180 |  |  |  |  | 185 |  |  |  |  | 190 |  |  |  |

| gaa | gtt | tat | tct | aat | cca | tgc | ctg | gaa | gaa | aac | aaa | cca | ggc | att | gtt | 624 |
| Glu | Val | Tyr | Ser | Asn | Pro | Cys | Leu | Glu | Glu | Asn | Lys | Pro | Gly | Ile | Val |  |
|  |  | 195 |  |  |  |  | 200 |  |  |  |  | 205 |  |  |  |  |

| tat | gct | tcc | ctg | aac | cat | tct | gtc | att | gga | ccg | aac | tca | aga | ctg | gca | 672 |
| Tyr | Ala | Ser | Leu | Asn | His | Ser | Val | Ile | Gly | Pro | Asn | Ser | Arg | Leu | Ala |  |
| 210 |  |  |  |  | 215 |  |  |  |  | 220 |  |  |  |  |  |  |

| aga | aat | gta | aaa | gaa | gca | cca | aca | gaa | tat | gca | tcc | ata | tgt | gtg | agg | 720 |
| Arg | Asn | Val | Lys | Glu | Ala | Pro | Thr | Glu | Tyr | Ala | Ser | Ile | Cys | Val | Arg |  |
| 225 |  |  |  |  | 230 |  |  |  |  | 235 |  |  |  |  | 240 |  |

| agt | taa |  |  |  |  |  |  |  |  |  |  |  |  |  |  | 726 |
| Ser |  |  |  |  |  |  |  |  |  |  |  |  |  |  |  |  |

```
<210> SEQ ID NO 32
<211> LENGTH: 241
<212> TYPE: PRT
<213> ORGANISM: Homo sapiens

<400> SEQUENCE: 32

Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
                20                  25                  30

Ser Cys Asp Val Gln Leu Tyr Ile Lys Arg Gln Ser Glu His Ser Ile
            35                  40                  45

Leu Ala Gly Asp Pro Phe Glu Leu Glu Cys Pro Val Lys Tyr Cys Ala
        50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Glu Lys Asn Ile Ser
                85                  90                  95

Phe Phe Ile Leu His Phe Glu Pro Val Leu Pro Asn Asp Asn Gly Ser
                100                 105                 110

Tyr Arg Cys Ser Ala Asn Phe Gln Ser Asn Leu Ile Glu Ser His Ser
            115                 120                 125

Thr Thr Leu Tyr Val Thr Gly Lys Gln Asn Glu Leu Ser Asp Thr Ala
        130                 135                 140

Gly Arg Glu Ile Asn Leu Val Asp Ala His Leu Lys Ser Glu Gln Thr
145                 150                 155                 160

Glu Ala Ser Thr Arg Gln Asn Ser Gln Val Leu Leu Ser Glu Thr Gly
                165                 170                 175

Ile Tyr Asp Asn Asp Pro Asp Leu Cys Phe Arg Met Gln Glu Gly Ser
            180                 185                 190

Glu Val Tyr Ser Asn Pro Cys Leu Glu Glu Asn Lys Pro Gly Ile Val
            195                 200                 205

Tyr Ala Ser Leu Asn His Ser Val Ile Gly Pro Asn Ser Arg Leu Ala
        210                 215                 220

Arg Asn Val Lys Glu Ala Pro Thr Glu Tyr Ala Ser Ile Cys Val Arg
225                 230                 235                 240

Ser
```

ANTICANCER AGENT COMPRISING HVJ-E AND IMMUNE CHECKPOINT PROTEIN INHIBITOR

CROSS-REFERENCE TO RELATED APPLICATIONS

This patent application is the U.S. national phase of International Patent Application No. PCT/JP2017/039568, filed Nov. 1, 2017, which claims the benefit of Japanese Patent Application No. 2016-214198, filed on Nov. 1, 2016, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 113,256 bytes ASCII (Text) file named "743436Sequence-Listing.txt," created Apr. 30, 2019.

TECHNICAL FIELD

The present invention relates to an anticancer agent containing HVJ-E (hemagglutinating virus of Japan envelope) and an inhibitor of an immune checkpoint protein.

BACKGROUND ART

Immune checkpoint protein is a factor that prevents onset and the like of autoimmune diseases due to abnormal activation of the immune system. It is known that PD-1 (Programmed cell death protein 1, also known as CD279), PD-L1 (Programmed cell death ligand 1, also known as B7-H1/CD274), PD-L2 (Programmed cell death ligand 2, also known as B7-DC/CD273) and CTLA-4 (cytotoxic T-lymphocyte-associated antigen 4, also known as CD152) and the like are major molecules (non-patent document 1).

These immune checkpoint proteins are generally expressed in the cells of the immune system, and PD-1 is expressed in the cells of activated T lymphocyte, B lymphocyte, myeloid cell and the like. PD-L1, a ligand for PD-1, is constitutively expressed in various cells in the body, including T lymphocytes stimulated with γ-interferon. Similarly, PD-L2, which is a ligand for PD-1, is induced to express in antigen-presenting cells (macrophage, dendritic cell and the like) upon induction of immune responses such as inflammation. On the other hand, CTLA-4 is induced to express in activated T lymphocytes and NK cells, and both CTLA-4 ligands B7.1 and B7.2 are expressed in cells specialized for antigen-presenting cells such as macrophages, dendritic cells and the like.

Since cancer cells are derived from autologous cells in the body, they were conventionally considered to be less susceptible to elimination by the immune system. In recent years, it has been suggested that suppression of the immune system by immune checkpoint proteins is a mechanism by which cancer cells avoid attack from the immune system in the body (non-patent document 2). In particular, it has been clarified that PD-L1 expressed by cancer cells suppresses the function of cytotoxic T lymphocytes important for tumor immunity through binding to PD-1, and that cancer cells are aggressively avoiding attack of the immune system (non-patent document 3). In addition, it has also been clarified that an antitumor effect is observed by releasing immunosuppression by CTLA-4 and PD-1 (non-patent document 4). As a result, antibody drugs such as anti-CTLA-4 antibody and anti-PD-1 antibody have been clinically developed as inhibitors of immune checkpoint proteins and approved as a therapeutic drug for malignant melanoma, non-small cell lung cancer, renal cancer or Hodgkin lymphoma (non-patent document 5). In addition, clinical development for anti-PD-L1 antibody is also in progress for patients with bladder cancer, pancreatic cancer, breast cancer, colorectal cancer, lymphoma, and the like (non-patent document 6).

As described above, treatments with inhibitors of the immune checkpoint proteins showed therapeutic effects in some cancers, which in turn indicated the direction of a new cancer treatment in which the function of the immune checkpoint protein that suppresses the immune system is released. On the other hand, cases and cancer types for which inhibitors of the immune checkpoint proteins fail to show a therapeutic effect have been reported. The problem is how to improve the therapeutic effect of the inhibitors of the immune checkpoint proteins (non-patent document 7).

HVJ-E is a particulate substance of completely inactivated HVJ (hemagglutinating virus of Japan), a paramyxovirus with rodent specificity (non-patent document 8). The inventors have heretofore reported that HVJ-E has plural antitumor activities including antitumor immunity and induction of cancer cell-specific apoptosis (non-patent documents 9-13); however, it is still unclear how the combined antitumor effect of HVJ-E changes when an inhibitor of an immune checkpoint protein is simultaneously activated.

DOCUMENT LIST

Non-Patent Documents non-patent document 1: Korman A J, et al. Checkpoint blockade in cancer immunotherapy. Adv Immunol. 2006; 90:297-339.

non-patent document 2: Dong H, et al. Tumor-associated B7-H1 promotes T-cell apoptosis: a potential mechanism of immune evasion. Nat Med. 2002 August; 8(8):793-800.

non-patent document 3: Kleffel S, et al. Melanoma Cell—Intrinsic PD-1 Receptor Functions Promote Tumor Growth. Cell. 2015 Sep. 10; 162(6):1242-56.

non-patent document 4: Littman D R. Releasing the Brakes on Cancer Immunotherapy. Cell. 2015 Sep. 10; 162(6): 1186-90.

non-patent document 5: Sharma P, Allison J P. The future of immune checkpoint therapy. Science. 2015 Apr. 3; 348 (6230):56-61.

non-patent document 6: Wolchok J D. PD-1 Blockers. Cell. 2015 Aug. 27; 162(5):937 non-patent document 7: Tumeh P C, et al. PD-1 blockade induces responses by inhibiting adaptive immune resistance. Nature. 2014 Nov. 27; 515(7528):568-71.

non-patent document 8: Kaneda Y, et al. Hemagglutinating virus of Japan (HVJ) envelope vector as a versatile gene delivery system. Mol. Ther. 2002 August; 6(2):219-26.

non-patent document 9: Kurooka M, Kaneda Y. Inactivated Sendai virus particles eradicate tumors by inducing immune responses through blocking regulatory T cells. Cancer Research, 67, 227-236, 2007.

non-patent document 10: Kawaguchi Y, et al. Efficient eradication of hormone-resistant human prostate cancers by inactivated Sendai virus particle. Int. J. Cancer 2009. 124: 2478-87.

non-patent document 11: Matsushima-Miyagi T., et al. TRAIL and Noxa are selectively up-regulated in prostate cancer cells downstream of the RIG-I/MAVS signaling pathway by non-replicating Sendai virus particles. Clinical Cancer Research, 18, 6271-83, 2012.

non-patent document 12: Suzuki H, et al. Sendai virus F glycoprotein induces IL-6 production in dendritic cells in a fusion-independent manner. FEBS Letter, 2008. 582: 1325-29.

non-patent document 13: Nomura M, et al. Accumulation of cytosolic calcium induces necroptotic cell death in human neuroblastoma. Cancer Res. 74, 1056-1066, 2014.

SUMMARY OF THE INVENTION

Problems to be Solved by the Invention

It is an object of the present invention to provide a novel anticancer agent having a high proliferation suppressive effect on cancer cells and obtained by combining an inhibitor of an immune checkpoint protein, anti-PD-1 antibody, with HVJ-E, confirming whether the combination remarkably enhances a proliferation inhibitory effect on cancer cells and, based on the results thereof, combining HVJ-E with an inhibitor of an immune checkpoint protein, and a new cancer therapy.

Means of Solving the Problems

In an attempt to solve the aforementioned problems, the present inventors have administered HVJ-E and an anti-PD-1 antibody as an inhibitor of an immune checkpoint protein PD-1 in combination to a malignant melanoma transplanted mouse and evaluated the antitumor effect with changes in the tumor size as an index. As a result, it was confirmed that simultaneous administration of HVJ-E and an anti-PD-1 antibody causes a cooperative action of the two kinds of molecules and can suppress proliferation of cancer cells. While single administration of HVJ-E and single administration of an anti-PD-1 antibody were associated with a phenomenon of gradual attenuation of the antitumor effect, the administration of a combination of HVJ-E and an anti-PD-1 antibody showed a phenomenon of enhancement of the antitumor effect.

In addition, a combination of HVJ-E and an anti-PD-1 antibody was administered to a malignant pleuralmesothelioma-transplanted mouse, and the antitumor effect was evaluated with changes in the tumor size as an index. As a result, it was confirmed that simultaneous administration of HVJ-E and an anti-PD-1 antibody causes a cooperative action of the two kinds of molecules and can suppress proliferation of cancer cells. Furthermore, when an anti-PD-1 antibody alone was administered to a malignant pleuralmesothelioma-transplanted mouse, the survival rate was not improved, and when HVJ-E and an isotype control antibody were simultaneously administered, the survival rate decreased on a daily basis and the survival rate on the final day of evaluation was 0%, whereas when HVJ-E and an anti-PD-1 antibody were simultaneously administered, 40% of mice survived even on the final day of evaluation.

Furthermore, a combination of HVJ-E and an anti-PD-1 antibody was administered to a mouse transplanted with TRAMP-C1 cell, which is a prostate cancer cell spontaneously developed in transgenic mice expressing the SV40 Large T gene and the antitumor effect was evaluated with changes in the tumor size as an index. As a result, similar to the malignant melanoma-transplanted mouse, when HVJ-E and an anti-PD-1 antibody were simultaneously administered, it was confirmed that the two kinds of molecules cooperatively act and can suppress proliferation of cancer cells. Similar to the malignant melanoma-transplanted mouse, single administration of anti-PD-1 antibody resulted in a phenomenon in which the antitumor effect attenuated gradually to reach a tumor size similar to that in the negative control, whereas administration of a combination of HVJ-E and an anti-PD-1 antibody showed a phenomenon of enhancement of the antitumor effect than the administration of each single agent.

The above results have clarified that administration of a combination of HVJ-E and an anti-PD-1 antibody increases the cancer proliferation suppressive effect and survival rate improving effect beyond prediction of those of ordinary skill in the art, as compared to single administration of each. The present invention has been completed based on the above findings. That is, the present invention provides

[1] An anticancer agent comprising the following (1) and (2):
(1) HVJ-E (hemagglutinating virus of Japan envelope),
(2) an inhibitor of an immune checkpoint protein;

[2] the anticancer agent of [1], wherein the anticancer agent is a combination agent;

[3] the anticancer agent of [1], wherein the anticancer agent is a kit comprising a pharmaceutical composition comprising HVJ-E and a pharmaceutical composition comprising an inhibitor of an immune checkpoint protein;

[4] the anticancer agent of any of [1] to [3], wherein the inhibitor of an immune checkpoint protein is selected from the following:
(a) a nucleic acid containing a base sequence complementary or substantially complementary to a base sequence encoding an immune checkpoint protein, or a part thereof,
(b) a neutralizing antibody against the immune checkpoint protein;

[5] the anticancer agent of any of [1] to [4], wherein the cancer is selected from the group consisting of melanoma, Merkel cell carcinoma, lung cancer, mesothelioma, head and neck cancer, esophagus cancer, gastric cancer, liver cancer, pancreatic cancer, large intestine cancer, prostate cancer, kidney cancer, bladder cancer, urinary tract epithelial cancer, breast cancer, uterine cancer, ovarian cancer, brain tumor, thyroid cancer, angiosarcoma, rhabdomyosarcoma, leiomyosarcoma, fibrosarcoma, synovial sarcoma, liposarcoma, neuroendocrine tumor, lymphoma and leukemia;

[6] the anticancer agent of any of [1] to [4], wherein the cancer is melanoma, mesothelioma or prostate cancer;

[7] the anticancer agent of any of [1] to [6], wherein the immune checkpoint protein is selected from the group consisting of PD-1, PD-L1, PD-L2, CTLA-4, B7.1, B7.2, B7-H3, B7-H4, B7-H5 (VISTA), KIR, CD137, LAG-3, TIM-3, TIGIT, OX40 and BTLA;

[8] the anticancer agent of any of [1] to [6], wherein the immune checkpoint protein is PD-1;

[9] a method for the prophylaxis or treatment of cancer, comprising administering an effective amount of the following (1) and (2) to a subject:
(1) HVJ-E,
(2) an inhibitor of an immune checkpoint protein.

Effect of the Invention

The present invention can provide a new anticancer agent expected to achieve an antitumor effect remarkably superior to that by a single administration, by combining HVJ-E and an inhibitor of an immune checkpoint protein as the active ingredients.

DESCRIPTION OF EMBODIMENTS

Figure 1:
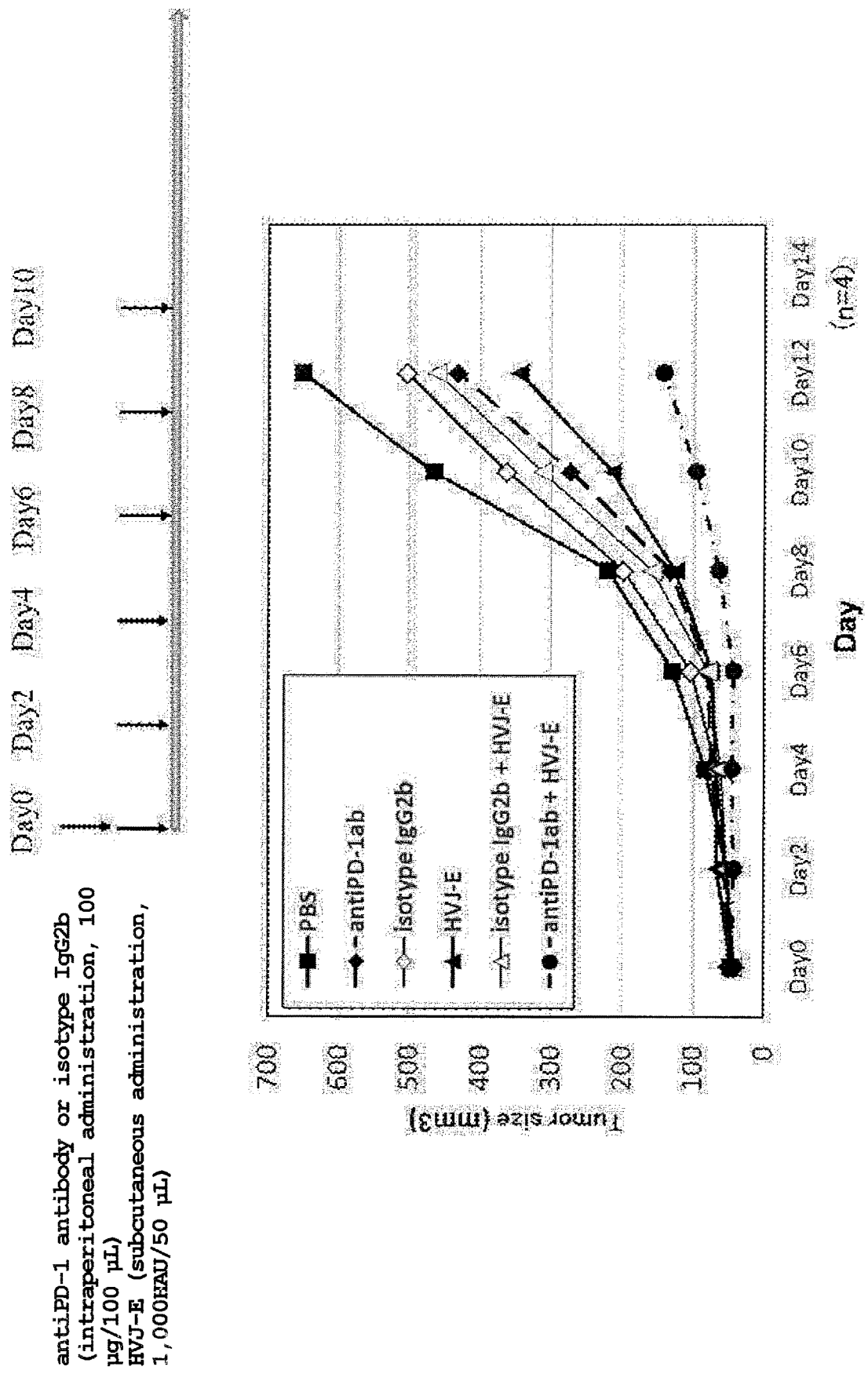
FIG. 1 shows a tumor volume when PBS, an isotype control antibody (intraperitoneal administration), an anti-PD-1 antibody (intraperitoneal administration), HVJ-E (subcutaneous administration), HVJ-E (subcutaneous administration)+isotype control antibody (intraperitoneal administration) or HVJ-E (subcutaneous administration)+anti-PD-1 antibody (intraperitoneal administration) was administered to a malignant melanoma-transplanted mouse and the mouse was observed for 12 days after the start of the administration.

The present invention is explained in detail in the following.

The present invention provides an anticancer agent containing the following (1) and (2):
(1) HVJ-E (hemagglutinating virus of Japan envelope),
(2) an inhibitor of an immune checkpoint protein.

In the present invention, Sendai virus envelope (hemagglutinating virus of Japan envelope, hereinafter HVJ-E of the present invention) refers to a virus envelope derived from Sendai virus (hemagglutinating virus of Japan, hereinafter HVJ) and maintaining the particle structure of HVJ. HVJ refers to a virus belonging to Paramyxoviridae Genus paramyxovirus and having a cell fusion activity. HVJ particles have, on the surface thereof, an envelope having hemagglutinin and neuraminidase and show polymorphism in diameter 150-300 nm. HVJ has, as a genome, negative-strand RNA of about 15,500 bases in length, has RNA polymerase, is unstable to heat, coagulates almost all kinds of erythrocytes and shows hemolysis. Examples of HVJ used for the preparation of HVJ-E of the present invention include VR-105, VR-907 and the like, and can be purchased from American Type Culture Collection (ATCC). HVJ may be a wild-type virus or a recombinant virus.

HVJ-E of the present invention can be prepared by inactivating HVJ. Examples of the method for inactivating HVJ for the preparation of HVJ-E of the present invention include UV treatment and alkylation treatment. By the inactivation treatment, the genomic RNA is modified or fragmented within the viral envelope and loses its activity, whereby the replication competence as a virus is lost. A method for preparing HVJ-E of the present invention is specifically described in JP-A-2001-286282 (WO 01/57204), JP-A-2002-065278, WO 03/014338 and the like, and particularly, HVJ-E can be prepared according to the method described in Example 8 and the like of JP-A-2001-286282. The thus-obtained HVJ-E of the present invention having no replication competence but maintaining cell fusion ability can also be utilized as a gene transfer vector by encapsulating gene, polynucleotide, oligonucleotide, plasmid and the like. HVJ-E of the present invention may also be a fused particle obtained by fusing a liposome encapsulating gene and protein, and HVJ after previous inactivation of RNA by UV radiation (Sendai virus-liposome).

In the present invention, the "immune checkpoint protein" is a factor known as a protein that modulates the immune system in the body and inhibition of the activity thereof is suggested to be useful in the cancer treatment. Examples of the immune checkpoint protein include PD-1, PD-L1, PD-L2, CTLA-4, B7.1, B7.2, B7-H3, B7-H4, B7-H5 (VISTA), KIR, CD137, LAG-3, TIM-3, TIGIT, OX40 and BTLA, among which PD-1 is preferable. Here, PD-1 is a protein consisting of the amino acid sequence shown in SEQ ID NO: 2, PD-L1 is a protein consisting of the amino acid sequence shown in SEQ ID NO: 4, PD-L2 is a protein consisting of the amino acid sequence shown in SEQ ID NO: 6, CTLA-4 is a protein consisting of the amino acid sequence shown in SEQ ID NO: 8, B7.1 is a protein consisting of the amino acid sequence shown in SEQ ID NO: 10, B7.2 is a protein consisting of the amino acid sequence shown in SEQ ID NO: 12, B7-H3 is a protein consisting of the amino acid sequence shown in SEQ ID NO: 14, B7-H4 is a protein consisting of the amino acid sequence shown in SEQ ID NO: 16, B7-H5 (VISTA) is a protein consisting of the amino acid sequence shown in SEQ ID NO: 18, KIR is a protein consisting of the amino acid sequence shown in SEQ ID NO: 20, CD137 is a protein consisting of the amino acid sequence shown in SEQ ID NO: 22, LAG-3 is a protein consisting of the amino acid sequence shown in SEQ ID NO: 24, TIM-3 is a protein consisting of the amino acid sequence shown in SEQ ID NO: 26, TIGIT is a protein consisting of the amino acid sequence shown in SEQ ID NO: 28, OX40 is a protein consisting of the amino acid sequence shown in SEQ ID NO: 30 and BTLA is a protein consisting of the amino acid sequence shown in SEQ ID NO: 32.

In the present invention, the "inhibitor of an immune checkpoint protein" is not particularly limited as long as it is a substance that suppresses the expression or activity of an immune checkpoint protein.

In the present invention, the "substance that suppresses the expression of immune checkpoint protein" may be one that acts in any stage at the immune checkpoint protein gene transcription level, post-transcriptional regulation level, translation-into-protein level, post-translational modification level and the like. Therefore, examples of a substance that inhibits the expression of immune checkpoint protein include a substance that inhibits the transcription of the gene, a substance that inhibits the processing of the initial transcription product into mRNA, a substance that inhibits the transportation of mRNA to cytoplasm, a substance that promotes the degradation of mRNA, a substance that inhibits the translation of mRNA into protein, a substance that inhibits the post-translational modification of immune checkpoint protein and the like. Although any one that acts in any stage can be preferably used, a substance that inhibits the translation of mRNA into protein is preferred in that the production of immune checkpoint protein is directly inhibited.

As a substance that specifically inhibits the translation of the mRNA of immune checkpoint protein into protein, preferably, a nucleic acid comprising a base sequence complementary or substantially complementary to the base sequence of mRNA of immune checkpoint protein or a portion thereof can be mentioned.

As a base sequence complementary or substantially complementary to the base sequence of the mRNA of immune checkpoint protein, (a) a base sequence complementary or substantially complementary to a base sequence encoding immune checkpoint protein, or (b) a base sequence that hybridizes under high stringent conditions with a complementary chain sequence of a base sequence encoding immune checkpoint protein and is complementary or substantially complementary to a base sequence encoding a protein having substantially the same activity as the immune checkpoint protein can be mentioned.

Examples of the "base sequence encoding an immune checkpoint protein" include a base sequence shown in SEQ ID NO: 1 as a base sequence encoding PD-1, a base sequence shown in SEQ ID NO: 3 as a base sequence encoding PD-L1, a base sequence shown in SEQ ID NO: 5 as a base sequence encoding PD-L2, a base sequence shown in SEQ ID NO: 7 as a base sequence encoding CTLA-4, a base sequence shown in SEQ ID NO: 9 as a base sequence encoding B7.1, a base sequence shown in SEQ ID NO: 11 as a base sequence encoding B7.2, a base sequence shown in SEQ ID NO: 13 as a base sequence encoding B7-H3, a base sequence shown in SEQ ID NO: 15 as a base sequence encoding B7-H4, a base sequence shown in SEQ ID NO: 17 as a base sequence encoding B7-H5 (VISTA), a base sequence shown in SEQ ID NO: 19 as a base sequence encoding KIR, a base sequence shown in SEQ ID NO: 21 as a base sequence encoding CD137, a base sequence shown in SEQ ID NO: 23 as a base sequence encoding LAG-3, a base sequence shown in SEQ ID NO: 25 as a base sequence encoding TIM-3, a base sequence shown in SEQ ID NO: 27 as a base sequence encoding TIGIT, a base sequence shown in SEQ ID NO: 29 as a base sequence encoding OX40 and a base sequence shown in SEQ ID NO: 31 as a base sequence encoding BTLA.

Being "substantially complementary" means having a complementarity of about 70% or more, preferably about 80% or more, more preferably about 90% or more, most preferably about 95% or more, between the base sequences. The "activity" refers to an action to suppress the antitumor activity of T cell against cancer cells and the like. Being "substantially of the same quality" means that the activity thereof is qualitatively (e.g., physiologically or pharmacologically) the same. Therefore, the quantitative factors such as the extent of the activity (e.g., about 0.1 to about 10 times, preferably about 0.5 to about 2 times) and the molecular weight of the protein may be different. The activity of the immune checkpoint protein can be measured by a method known per se.

As examples of the highly stringent conditions, conditions of a hybridization reaction in 6×SSC (sodium chloride/sodium citrate) at 45° C. followed by washing in 0.2×SSC/0.1% SDS at 65° C. once or more and the like can be mentioned.

More preferably, as a base sequence complementary or substantially complementary to the base sequence of the mRNA of immune checkpoint protein, (a) a base sequence complementary or substantially complementary to a base sequence encoding immune checkpoint protein can be mentioned.

"A portion of a base sequence complementary or substantially complementary to the base sequence of the mRNA of immune checkpoint protein" is not particularly limited with respect to the length and position thereof, as far as the portion is capable of binding specifically to the mRNA of immune checkpoint protein, and capable of inhibiting the protein translation from the mRNA; in terms of sequence specificity, the portion comprises at least 10 bases or more, preferably about 15 bases or more, and more preferably about 20 bases or more, of a portion complementary or substantially complementary to the target sequence.

Specifically, as a nucleic acid comprising a base sequence complementary or substantially complementary to the base sequence of the mRNA of immune checkpoint protein or a portion thereof, any one of the following (i) to (iii) can be preferably mentioned.
(i) An antisense nucleic acid against the mRNA of immune checkpoint protein
(ii) An siRNA against the mRNA of immune checkpoint protein
(iii) A nucleic acid capable of producing an siRNA against the mRNA of immune checkpoint protein
(i) Antisense Nucleic Acid Against mRNA of Immune Checkpoint Protein The antisense nucleic acid against the mRNA of immune checkpoint protein in the present invention (antisense nucleic acid of the present invention) is a nucleic acid comprising a base sequence complementary or substantially complementary to the base sequence of the mRNA or a portion thereof, and having the function of suppressing protein synthesis by binding to the target mRNA while forming a specific and stable double strand therewith.

Examples of the antisense nucleic acid include polydeoxy ribonucleotides comprising 2-deoxy-D-ribose, polyribonucleotides comprising D-ribose, other types of polynucleotides being N-glycosides of the purine or pyrimidine base, other polymers having a non-nucleotide backbone (for example, commercially available protein nucleic acids and nucleic acid polymers specific for synthetic sequences) or other polymers comprising a special linkage (provided that the polymers comprise nucleotides having such an alignment that allows base pairing or base attachment, as found in DNA or RNA) and the like. These may be double-stranded DNAs, single-stranded DNAs, double-stranded RNAs, single-stranded RNAs, or DNA:RNA hybrids.

As mentioned above, the antisense nucleic acid may be DNA or RNA, or a DNA/RNA chimera. When the antisense nucleic acid is a DNA, an RNA:DNA hybrid formed by a target RNA and antisense DNA is capable of being recognized by endogenous RNase H to cause selective degradation of the target RNA. Therefore, in the case of an antisense DNA intended to cause degradation by RNase H, the target sequence may be not only a sequence in the mRNA, but also the sequence of an intron region in the initial translation product of the immune checkpoint protein.

The length of the target region of the antisense nucleic acid of the present invention is not particularly limited as long as it is a region that inhibits the translation of an immune checkpoint protein into a protein when the antisense nucleic acid is hybridized by the antisense nucleic acid. It may be the total sequence, or a partial sequence, of the mRNA encoding these proteins, and the length is about 10 bases for the shortest, and the entire sequence of the mRNA or initial transcription product for the longest. Taking into account the issues of the ease of synthesis, antigenicity, and intracellular migration and the like, an oligonucleotide consisting of about 10 to about 40 bases, particularly about 15 to about 30 bases, is preferable, but this is not to be construed as limiting. Specifically, the 5'-end hairpin loop, 5'-end 6-base-pair repeats, 5'-end untranslated region, translation initiation codon, protein coding region, ORF translation stop codon, 3'-end untranslated region, 3'-end palindrome region, 3'-end hairpin loop and the like of the immune checkpoint protein gene may be chosen as preferable target regions of the antisense, but the target region is not limited to these.

Furthermore, the antisense nucleic acid of the present invention may be one that not only hybridizes with the mRNA or initial transcription product of immune checkpoint protein to inhibit the translation into protein, but also is capable of binding to these genes being double-stranded DNA to form a triple strand (triplex) and hence to inhibit the transcription to RNA (antigene).

While the nucleotide molecules that constitute the antisense nucleic acid may be natural-type RNAs or DNAs, the molecules can contain various chemical modifications to increase the stability (chemical and/or to-enzyme) or specific activity (affinity for RNA). For example, to prevent degradation by hydrolylases such as nuclease, the phosphoric acid residue (phosphate) of each nucleotide that constitutes the antisense nucleic acid can be substituted with, for example, a chemically modified phosphoric acid residue such as phosphorothioate (PS), methylphosphonate, or phosphorodithionate. The hydroxyl group at the 2'-position of the sugar (ribose) of each nucleotide may be replaced with —OR (R represents, for example, $CH_3$(2'-O-Me), $CH_2CH_2OCH_3$(2'-O-MOE), $CH_2CH_2NHC(NH)NH_2$, $CH_2CONHCH_3$, $CH_2CH_2CN$ or the like). Furthermore, a base moiety (pyrimidine, purine) may be chemically modified; for example, introduction of a methyl group or a cationic functional group into the 5-position of the pyrimidine base, substitution of the 2-position carbonyl group with thiocarbonyl and the like can be mentioned.

Regarding the conformation of the sugar moiety of RNA, two types are dominant: C2'-endo (type S) and C3'-endo (type N); in single-stranded RNA, the sugar moiety occurs in equilibrium of the two types, but when a double strand is formed, the conformation is fixed for the type N. Therefore, BNA (LNA) (Imanishi, T. et al., Chem. Commun., 1653-9, 2002; Jepsen, J. S. et al., Oligonucleotides, 14, 130-46, 2004), or ENA (Morita, K. et al., Nucleosides Nucleotides Nucleic Acids, 22, 1619-21, 2003), an RNA derivative wherein the conformation of the sugar moiety is fixed for the type N by bridging the 2' oxygen and 4' carbon so as to confer strong bindability to the target RNA, can also be preferably used.

The antisense oligonucleotide of the present invention can be prepared by determining the target sequence for the mRNA or initial transcription product on the basis of the cDNA sequence or genomic DNA sequence of immune checkpoint protein, and synthesizing a sequence complementary thereto using a commercially available automated DNA/RNA synthesizer (Applied Biosystems, Beckman and the like). All antisense nucleic acids comprising the aforementioned various modifications can be chemically synthesized by techniques known per se.

(ii) siRNA Against mRNA of Immune Checkpoint Protein

In the present specification, a double-stranded RNA consisting of an oligo-RNA complementary to the mRNA of immune checkpoint protein and a complementary chain thereof, what is called an siRNA, is also defined as being included in nucleic acids comprising a base sequence complementary or substantially complementary to the base sequence of the mRNA of immune checkpoint protein or a portion thereof. It had been known that so-called RNA interference (RNAi), which is a phenomenon wherein if short double-stranded RNA is introduced into a cell, mRNAs complementary to the RNA are degraded, occurs in nematodes, insects, plants and the like; since this phenomenon was confirmed to also occur widely in animal cells [Nature, 411(6836): 494-498 (2001)], RNAi has been widely utilized as an alternative technique to ribozymes. An siRNA can be designed as appropriate on the basis of base sequence information on the target mRNA using commercially available software (e.g., RNAi Designer; Invitrogen).

Ribonucleoside molecules constituting an siRNA may also undergo the same modifications as with the above-described antisense nucleic acids in order to increase the stability, specific activity and the like. However, in the case of an siRNA, if all ribonucleoside molecules in the natural type RNA are substituted by the modified form, the RNAi activity is sometimes lost, so that it is necessary that the minimum number of modified nucleosides be introduced to allow the RISC complex to function.

An siRNA can be prepared by synthesizing a sense chain and antisense chain of a target sequence on the mRNA using an automated DNA/RNA synthesizer, respectively, and denaturing the chains in an appropriate annealing buffer solution at about 90 to about 95° C. for about 1 minute, and thereafter annealing the chains at about 30 to about 70° C. for about 1 to about 8 hours. An siRNA can also be prepared by synthesizing a short hairpin RNA (shRNA) serving as an siRNA precursor, and cleaving this using a dicer.

(iii) Nucleic Acid Capable of Producing siRNA Against mRNA of Immune Checkpoint Protein In the present specification, a nucleic acid designed to be capable of producing the above-described siRNA against the mRNA of immune checkpoint protein in a living organism is also defined as being included in nucleic acids comprising a base sequence complementary or substantially complementary to the base sequence of the mRNA of immune checkpoint protein or a portion thereof. As such nucleic acids, the aforementioned shRNA, expression vectors constructed to express the shRNA and the like can be mentioned. An shRNA can be prepared by designing an oligo-RNA comprising a base sequence prepared by joining a sense chain and antisense chain of a target sequence on mRNA via a spacer sequence having a length allowing it to form an appropriate loop structure (for example, about 15 to 25 bases) inserted therebetween, and synthesizing this using an automated DNA/RNA synthesizer. An expression vector comprising an shRNA expression cassette can be prepared by preparing a double-stranded DNA that encodes the above-described shRNA by a conventional method, and thereafter inserting the DNA into an appropriate expression vector. As the shRNA expression vector, one having a Pol III system promoter such as U6 or H1 can be used. In this case, an shRNA transcribed in an animal cell incorporating the expression vector forms a loop by itself, and is thereafter processed by an endogenous enzyme dicer and the like, whereby a mature siRNA is formed.

Another preferred embodiment of a nucleic acid comprising a base sequence complementary or substantially complementary to the base sequence of the mRNA of immune checkpoint protein or a portion thereof is a ribozyme capable of specifically cleaving the mRNA in the coding region. The "ribozyme" in a narrow sense refers to an RNA possessing an enzyme activity to cleave nucleic acids. In the present specification, it is used as a concept encompassing DNA, as long as it possesses sequence-specific nucleic acid cleavage activity, since it has recently been found that an oligo DNA having the base sequence of the enzyme activity site also possesses nucleic acid cleavage activity. One of the most versatile ribozymes is self-splicing RNA found in infectious RNAs such as viroid and virusoid, and the hammerhead type, the hairpin type and the like are known. The hammerhead type exhibits enzyme activity with about 40 bases; it is possible to cleave the target mRNA specifically by making several bases at both ends adjoining to the portion assuming a hammerhead structure (about 10 bases in total) to be a sequence complementary to the desired cleavage site of the mRNA. Because this type of ribozyme has RNA as the only substrate, it offers the additional advantage of not attacking genomic DNA. When the mRNA itself of an immune checkpoint protein assumes a double-stranded structure, the target sequence can be made single-stranded by using a hybrid ribozyme joined with an RNA motif derived from a viral nucleic acid, capable of binding specifically to RNA helicase [Proc. Natl. Acad. Sci. USA, 98(10): 5572-5577 (2001)]. Furthermore, when a ribozyme is used in the form of an expression vector comprising the DNA that encodes the same, the ribozyme can also be made to be a hybrid ribozyme further joined with a sequence of modified tRNA, in order to promote the transfer of a transcription product to cytoplasm [Nucleic Acids Res., 29(13): 2780-2788 (2001)].

The nucleic acid comprising a base sequence complementary or substantially complementary to the base sequence of the mRNA of immune checkpoint protein or a portion thereof may be combined with a substance for introduction into the cells. For example, the aforementioned nucleic acid may be provided in a form encapsulated in HVJ-E, liposome or microsphere. The aforementioned nucleic acid may also be provided in a form attached to a hydrophobic substance such as polycations that act to neutralize the charge of phosphate backbone, such as polylysines, and hydrophobic ones such as lipids (e.g., phospholipids, cholesterols and the like) that enhance the interaction with cell membrane or increase nucleic acid uptake. Lipids preferred for addition are cholesterols and derivatives thereof (e.g., cholesteryl chloroformate, cholic acid and the like). These moieties may be attached to the 3' end or 5' end of a nucleic acid, and can also be attached via a base, sugar, or intramolecular nucleoside linkage. Other groups may be capping groups placed specifically at the 3' end or 5' end of the nucleic acid to prevent degradation by nucleases such as exonuclease and RNase. Such capping groups include, but are not limited to, hydroxyl protecting groups known in the art, including glycols such as polyethylene glycol and tetraethylene glycol.

The inhibitory activities of these nucleic acids on the expression of immune checkpoint protein can be examined using a transformant incorporating the immune checkpoint protein gene, in vivo and in vitro expression systems for the immune checkpoint protein gene, or an in vivo or in vitro protein translation system for the immune checkpoint protein.

A substance that suppresses the expression of immune checkpoint protein in the present invention is not limited to the above-described nucleic acids comprising a base sequence complementary or substantially complementary to the base sequence of the mRNA of immune checkpoint protein or a portion thereof; as far as the substance directly or indirectly inhibits the production of immune checkpoint protein, it may be another substance such as a low-molecular compound.

The substance that suppresses the expression of immune checkpoint protein in the present invention may be any as long as it suppresses an action to control an antitumor activity of T cells against cancer cells. For example, a substance that inhibits the bindability between PD-1 and PD-L1, and the like can be mentioned.

Specifically, as an example of a substance that inhibits the activity of immune checkpoint protein, a neutralizing antibody against immune checkpoint protein can be mentioned. The antibody may be a polyclonal antibody or a monoclonal antibody. These antibodies can be produced according to a method of antibody or antiserum production known per se. The isotype of the antibody is not particularly limited, and is preferably IgG, IgM or IgA, particularly preferably IgG. The antibody is not particularly limited, as far as it has at least a complementarity determining region (CDR) for specifically recognizing and binding to a target antigen, and the antibody may be, in addition to a complete antibody molecule, for example, a fragment such as Fab, Fab', or F(ab')$_2$, a conjugate molecule prepared by a gene engineering technique, such as scFv, scFv-Fc, minibody, or diabody, or a derivative thereof modified with a molecule having protein-stabilizing action, such as polyethylene glycol (PEG).

Examples of known neutralizing antibody against immune checkpoint protein include Ipilimumab (Bristol-Myers Squibb) and Tremelimumab (Astrazeneca) as anti-CTLA-4 antibody, Nivolumab (Bristol-Myers Squibb) and Pembrolizumab (Merck/MSD) as anti-PD-1 antibody, Durvalumab (Astrazeneca) and Atezolizumab (Roche), Avelumab (Pfizer/EMD Serono/Merck KGaA) and Pidilizumab (CureTech) as anti-PD-L1 antibody, lirilumab (Bristol-Myers Squibb) as anti-KIR antibody, urelumab (Bristol-Myers Squibb) as anti-CD137 antibody, and BMS-986016 (Bristol-Myers Squibb) as anti-LAG-3 antibody.

The method of preparing an antigen used for preparing the antibody of the present invention and a method of producing the antibody are described below.

(1) Preparation of Antigen

The antigen used to prepare the antibody of the present invention may be any such as the above-mentioned immune checkpoint protein or a partial peptide thereof, or a (synthetic) peptide having 1 kind or 2 or more kinds of the same antigen determinant (hereinafter, these are also sometimes simply referred to as the antigen of the present invention).

An immune checkpoint protein or a partial peptide thereof is produced by, for example, (a) preparation from mammalian tissue or cell by a known method or a method analogous thereto, (b) chemical synthesis by a known peptide synthesis method using a peptide synthesizer or the like, (c) culturing a transformant containing a DNA encoding an antigen protein against immune checkpoint protein, or (d) biochemical synthesis using, as a template, a nucleic acid encoding immune checkpoint protein or a partial peptide thereof and a cell-free transcription/translation system.

(a) When the immune checkpoint protein or a partial peptide thereof is prepared from tissue or cells of a mammal, the tissue or cells may be homogenized, after which a crude fraction (e.g., membrane fraction, soluble fraction) can also be used as the antigen as is. Alternatively, the antigen can be purified and isolated by performing extraction with an acid, surfactant or alcohol and the like, and applying the extract to a combination of salting-out, dialysis, chromatographies such as gel filtration reversed-phase chromatography, ion exchange chromatography, and affinity chromatography. The obtained immune checkpoint protein or a partial peptide thereof may be used as the immunogen as is, and may be subjected to limited degradation using a peptidase and the like to yield a partial peptide that can be used as the immunogen.

(b) When the antigen of the present invention is chemically prepared, as the synthetic peptide, for example, one having the same structure as immune checkpoint protein or a partial peptide thereof purified from a natural material by the method of the aforementioned (a), specifically, a peptide containing one or more kinds of the same amino acid sequence as the amino acid sequence consisting of at least 3, preferably not less than 6, amino acids in the amino acid sequence of an immune checkpoint protein or a partial peptide thereof, and the like are used.

(c) When the antigen of the present invention is produced using a transformant containing a DNA, the DNA can be produced according to a known cloning method [for example, the method described in Molecular Cloning 2nd ed. (J. Sambrook et al., Cold Spring Harbor Lab. Press, 1989) and the like]. The cloning method includes a method including (1) isolating a DNA encoding the antigen from the human cDNA library by a hybridization method using a DNA probe designed based on a gene sequence encoding immune checkpoint protein or a partial peptide thereof, or (2) preparing a DNA encoding the antigen by PCR method using a DNA probe designed based on a gene sequence encoding immune checkpoint protein or a partial peptide thereof and mammal-derived cDNA as a template, and inserting the DNA into an expression vector compatible with the host and the like. The desired antigen can be obtained by culturing, in a suitable medium, a transformant obtained by transforming a host with the expression vector.

(d) When a cell-free transcription/translation system is utilized, a method including synthesizing mRNA by using an expression vector inserted with a DNA encoding the antigen, which is prepared by a method similar to the above-mentioned (c) (e.g., expression vector in which the DNA is under control of T7, SP6 promoter and the like, and the like) as a template and using a transcription reaction mixture containing an RNA polymerase compatible with the promoter and a substrate (NTPs), and performing a translation reaction by using the mRNA as a template and by a known cell-free translation system (e.g., *Escherichia coli*, rabbit reticulocyte, extract of wheat germ and the like), and the like can be mentioned. The transcription reaction and the translation reaction can also be performed at once in the same reaction mixture by appropriately adjusting the salt concentration and the like.

As the antigen, a peptide having a complete immune checkpoint protein or a partial amino acid sequence thereof can be used. As the partial amino acid sequence, one consisting of not less than 3 continuous amino acid residues, preferably not less than 4, more preferably not less than 5, further preferably not less than 6, continuous amino acid residues can be mentioned. Alternatively, as the amino acid sequence, one consisting of not more than 20 continuous amino acid residues, preferably not more than 18, more preferably not more than 15, further preferably not more than 12, continuous amino acid residues can be mentioned. A part (e.g., 1 to several) of these amino acid residues is optionally substituted by a substitutable group (e.g., Cys, hydroxyl group etc.). A peptide used as the antigen has an amino acid sequence containing one to several of such partial amino acid sequences.

Alternatively, mammalian cells themselves expressing the immune checkpoint protein or a partial peptide thereof can be used directly as the antigen I of the present invention. Preferably useful mammalian cells include natural cells as described in section (a) above, cells transformed by a method as described in section (c) above and the like. The host used for the transformation may be any cells collected from humans, monkeys, rats, mice, hamsters, chickens and the like and HEK293, COS7, CHO-K1, NIH3T3, Balb3T3, FM3A, L929, SP2/0, P3U1, NS0, B16, P388 and the like are preferably used. Natural mammalian cells or transformed warm-blooded animal cells that express the immune checkpoint protein or a partial peptide thereof can be injected to an immunized animal in suspension in a medium used for tissue culture (e.g., RPMI1640) or a buffer solution (e.g., Hanks' Balanced Salt Solution). The method of immunization may be any method allowing promotion of antibody production; intravenous injection, intraperitoneal injection, intramuscular injection or subcutaneous injection and the like are preferably used.

As the antigen of the present invention, an insolubilized antigen can also be directly immunized as long as it has immunogenicity. When an antigen (i.e., partial peptide of immune checkpoint protein) having a low molecular weight (e.g., molecular weight of not more than about 3,000) and having only one to several antigen determinants in a molecule is used, since such antigen is generally a hapten molecule with low immunogenicity, it can be bound or adsorbed to a suitable carrier and immunized as a complex. As the carrier, a natural or synthetic polymer can be used. As examples of the natural polymer, the serum albumin of a mammal such as cattle, rabbit or human, the thyroglobulin of a mammal such as cattle or rabbit, chicken ovalbumin, the hemoglobin of a mammal such as cattle, rabbit, human or sheep, keyhole limpet hemocyanin and the like are used. As examples of the synthetic polymer, various latexes of polymers or copolymers of polyamino acids, polystyrenes, polyacryls, polyvinyls, polypropylenes and the like, and the like can be mentioned.

Regarding the mixing ratio of the carrier and hapten, any carrier can be bound or adsorbed in any ratio, as long as an antibody against the antigen bound or adsorbed to the carrier is efficiently produced; usually, the above-mentioned natural or synthetic polymeric carrier in common use for preparation of an antibody against a hapten antigen, bound or adsorbed in a ratio of 0.1 to 100 parts by weight to 1 part by weight of the hapten, can be used.

Various condensing agents can be used for the coupling of hapten and carrier. For example, diazonium compounds such as bisdiazotized benzidine, which crosslink tyrosine, histidine, and tryptophan; dialdehyde compounds such as glutaraldehyde, which crosslink amino groups together; diisocyanate compounds such as toluene-2,4-diisocyanate; dimaleimide compounds such as N,N'-o-phenylenedimaleimide, which crosslink thiol groups together; maleimide activated ester compounds, which crosslink amino groups and thiol groups; carbodiimide compounds, which crosslink amino groups and carboxyl groups; and the like are conveniently used. When amino groups are crosslinked together, it is also possible to react one amino group with an activated ester reagent having a dithiopyridyl group (for example, 3-(2-pyridyldithio)propionic acid N-succinimidyl (SPDP) and the like), followed by reduction, to introduce the thiol group, and to introduce a maleimide group into the other amino group using a maleimide activated ester reagent, followed by a reaction of both.

(2) Preparation of Monoclonal Antibody (a) Preparation of Monoclonal Antibody-Producing Cells The antigen of the present invention is singly administered as is, or along with a carrier or a diluent, to warm-blooded animals at a site enabling antibody production by an administration method such as intraperitoneal injection, intravenous injection, subcutaneous injection, intradermal injection and the like. To increase antibody productivity upon the administration, Freund's complete adjuvant or Freund's incomplete adjuvant may be administered. Dosing is normally performed about two to 10 times in total every 1 to 6 weeks. As examples of the warm-blooded animal to be used, monkeys, rabbits, dogs, guinea pigs, mice, rats, hamsters, sheep, goats, donkeys and chicken can be mentioned. To avoid the problem of anti-Ig antibody production, a mammal of the same kind as the subject of administration is preferable. For the production of a monoclonal antibody, generally, mouse and rat are preferably used.

Artificial immunization to human is ethically difficult. When the subject of administration of the antibody of the present invention is human, it is preferable to (i) obtain a human antibody by immunizing a human antibody-producing animal (e.g., mouse) prepared according to the below-mentioned method, (ii) produce a chimera antibody, a humanized antibody or complete human antibody according to the below-mentioned method, or (iii) obtain a human antibody by combining ex-vivo immunization method and cell immortalization with a virus, human-human (or mouse) hybridoma preparation technology, phage display method, and the like. The ex-vivo immunization method can also be preferably used when preparing an antibody derived from non-human animal, as a method for obtaining an antibody against an antigen which is unstable and difficult to prepare in a large amount, since an antibody against an antigen whose antibody production is suppressed by general immunization may be provided, an antibody can be obtained with an amount of antigen on the order of ng to μg, and immunity is completed in several days, and the like.

Examples of the animal cell used for the ex-vivo immunization method include lymphocyte, preferably B lymphocyte, and the like isolated from the peripheral blood, spleen, lymph node and the like of human and the above-mentioned warm-blooded animal (preferably mouse, rat). For example, in the case of mouse or rat cells, the spleen is isolated from about 4- to 12-week-old animal, splenocyte is separated, washed with a suitable medium (e.g., Dulbecco's modified Eagle medium (DMEM), RPMI1640 medium, hamF12 medium etc.)), suspended in a medium supplemented with fetal calf serum (FCS; about 5 to 20%) containing an antigen, and cultured using a $CO_2$ incubator or the like for about 4 to 10 days. Examples of the antigen concentration include, but are not limited to, 0.05-5 μg. It is preferable to prepare thymocyte culture supernatant of an animal of the same lineage (preferably about 1- to 2-week-old) according to a conventional method and add same to the culture medium.

It is difficult to obtain thymocyte culture supernatant by ex-vivo immunization of human cells. Thus, it is preferable to perform immunization by adding several kinds of cytokines such as IL-2, IL-4, IL-5, IL-6 and the like and, where necessary, an adjuvant substance (e.g., muramyl dipeptide etc.) to the medium together with the antigen.

In preparing a monoclonal antibody, an individual or cell population showing an increase in the antibody titer is selected from among warm-blooded animals (e.g., mouse, rat) or animal cells (e.g., human, mouse, rat) immunized with an antigen, the spleen or lymph node is collected 2 to 5 days after final immunization or cells cultured for 4-10 days after ex-vivo immunization are recovered, antibody-producing cells are isolated and fused with myeloma cells, whereby an antibody-producing hybridoma can be prepared. A measurement of antibody titer in serum can be performed by, for example, reacting a labeled antigen with the antiserum, then determining the activity of labeling agent bound to the antibody.

While the myeloma cell is not particularly limited as long as it can produce hybridoma that secretes a large amount of antibody, one that does not itself produce or secrete antibody is preferable, and one with high cell fusion efficiency is more preferable. To facilitate selection of hybridoma, a HAT (hypoxanthine, aminopterine, thymidine) sensitive strain is preferably used. For example, mouse myeloma cell is exemplified by NS-1, P3U1, SP2/0, AP-1 and the like, rat myeloma cell is exemplified by R210.RCY3, Y3-Ag 1.2.3 and the like, human myeloma cell is exemplified by SKO-007, GM 1500-6TG-2, LICR-LON-HMy2, UC729-6 and the like.

The fusion operation can be performed according to a known method, for example, the method of Koehler and Milstein [Nature, Vol. 256, p. 495 (1975)]. As examples of the fusogen, polyethylene glycol (PEG), Sendai virus and the like can be mentioned, with preference given to PEG etc. While the molecular weight of PEG is not particularly limited, PEG1000-PEG6000 is preferable since it has lower toxicity and comparatively low viscosity. The PEG concentration is, for example, about 10-80%, preferably about 30-50%. As the solution for dilution of PEG, serum-free medium (e.g., RPMI1640), complete medium containing about 5-20% of serum, phosphate buffered saline (PBS), various buffers such as tris buffer and the like can be used. When desired, DMSO (e.g., about 10-20%) can also be added. The pH of the fusion solution is, for example, about 4-10, preferably about 6-8.

A preferable ratio of the number of antibody-producing cells (splenocyte) and the number of bone marrow cells is generally about 1:1-20:1, and cell fusion can be efficiently performed by incubating generally at 20-40° C., preferably 30-37° C. for generally 1-10 min.

The antibody producing cell line can also be obtained by infecting antibody-producing cells with a virus capable of transforming lymphocytes and immortalizing the cells. Examples of the virus include Epstein-Barr (EB) virus and the like. Most people are immune to this virus because they have been infected with this virus as a subclinical infection with infectious mononucleosis. However, appropriate purification should be performed since virus particles are also produced when general EB virus is used. As an EB system with no possibility of virus contamination, use of a recombinant EB virus that retains the ability to immortalize B lymphocytes but lacks the ability to replicate viral particles (e.g., deficiency in switch gene for transition from latent infection state to lytic infection state and the like) is also preferable.

Since marmoset-derived B95-8 cells secrete EB virus, B lymphocyte can be easily transformed using the culture supernatant thereof. For example, the cell is cultured in a medium (e.g., RPMI1640) supplemented with a serum and penicillin/streptomycin (P/S), or a serum-free medium supplemented with a cell growth factor, the culture supernatant is separated by filtration or centrifugation and the like, antibody-producing B lymphocytes are suspended therein at an appropriate concentration (e.g., about $10^7$ cells/mL), and incubated at generally 20-40° C., preferably 30-37° C., generally for about 0.5-2 hr, whereby antibody-producing B cell line can be obtained. When human antibody-producing cells are provided as mixed lymphocytes, since most people have T lymphocytes that are toxic to EB virus-infected cells, it is preferable to remove T lymphocytes in advance by, for example, forming E rosette with sheep erythrocyte etc. to increase transformation frequency. In addition, lymphocyte specific to the target antigen can be selected by mixing soluble antigen-conjugated sheep erythrocyte with antibody-producing B lymphocytes, and the rosette is separated using a density gradient such as Percoll and the like. By adding a large excess of antigen, antigen-specific B lymphocytes are capped and do not present IgG on the surface, and therefore, when mixed with sheep erythrocyte conjugated with an anti-IgG antibody, only the antigen non-specific B lymphocytes form a rosette. Therefore, antigen-specific B lymphocyte can be sorted from this mixture by collecting rosette non-forming layers using a density gradient such as Percoll and the like.

Human antibody-secreting cell that has acquired infinite proliferation ability by transformation antibody secretory capacity can be back-fused with mouse or human myeloma cells to stably sustain the antibody secreting capacity. The myeloma cells same as those described above can be used.

Screening and breeding of hybridoma are generally performed by adding HAT (hypoxanthine, aminopterine, thymidine) and in an animal cell medium (e.g., RPMI1640) containing 5-20% FCS or a serum-free medium added with a cell growth factor. The concentration of hypoxanthine, aminopterine and thymidine is respectively about 0.1 mM, about 0.4 μM and about 0.016 mM and the like. Ouwabine resistance can be used to select human-mouse hybridoma. Since human cell lines are more sensitive to ouabain than mouse cell lines, unfused human cells can be eliminated by adding at about $10^{-7}$-$10^{-3}$ M to the medium.

It is preferable to use feeder cells or certain cell culture supernatants for selection of hybridomas. As the feeder cell, a heterogeneous cell type, which has a limited survival time to help emergence of hybridomas and to die, a cell that can produce a large amount of a growth factor useful for the emergence of hybridoma and has proliferation ability reduced by irradiation and the like are used. Examples of the mouse feeder cell include splenocyte, macrophage, blood, thymus cell and the like, and examples of the human feeder cell include peripheral blood mononuclear cell and the like. Examples of the cell culture supernatant include primary culture supernatants of the above-mentioned various cells and culture supernatants of various established lines of cells.

In addition, hybridoma can also be selected by fluorescently labeling the antigen and reacting same with the fused cells, and separating the cells that bind to the antigen by using a fluorescence activated cell sorter (FACS). In this case, a hybridoma producing the antibody against the target antigen can be directly selected, and therefore, the labor of cloning can be reduced greatly.

Various methods can be used for cloning a hybridoma producing a monoclonal antibody against the target antigen.

Since aminopterine inhibits many cellular functions, it is preferably removed from the medium as soon as possible. In the case of mouse and rat, since most myeloma cells die within 10-14 days, aminopterin can be removed after 2 weeks of fusion. Human hybridoma is generally maintained in aminopterin-supplemented medium for about 4 to 6 weeks after fusion. Hypoxanthine and thymidine are desirably removed more than one week or more after aminopterin removal. In the case of mouse cell, for example, complete medium supplemented with hypoxanthine and thymidine (HT) (e.g., RPMI 1640 supplemented with 10% FCS) 7 to 10 days after fusion. A visually observable clone emerges in about 8 to 14 days after fusion. When the diameter of the clone becomes about 1 mm, the amount of antibody in the culture supernatant can be measured.

The amount of the antibody can be measured by a method including adding a hybridoma culture supernatant to a solid phase (e.g., microplate) having, for example, a target antigen or a derivative thereof or a partial peptide thereof (including partial amino acid sequence used as antigen determinant) adsorbed thereto directly or along with a carrier, then adding an anti-immunoglobulin (IgG) antibody (used is an antibody against IgG derived from the same kind of animal as the animal from which the original antibody-producing cell is derived) labeled with a radioactive substance (e.g., $^{125}$I, $^{131}$I, $^{3}$H, $^{14}$C), an enzyme (e.g., β-galactosidase, β-glucosidase, alkaline phosphatase, peroxidase, malic acid dehydrogenase), a fluorescent substance (e.g., fluorescamine, fluorescein isothiocyanate), a luminescence substance (e.g., luminol, luminol derivative, luciferin, lucigenin) or the like, or protein A, and detecting an antibody against the target antigen (antigen determinant) bound to the solid phase, a method including adding a hybridoma culture supernatant to a solid phase to which anti-IgG antibody or protein A is adsorbed, adding the target antigen labeled with a label similar to the above or a derivative thereof or a partial peptide thereof, and detecting an antibody against the target antigen (antigen determinant) bound to the solid phase and the like.

As the cloning method, a limit dilution method is generally used. Cloning using soft agar or cloning using FACS is also possible. Cloning by the limiting dilution method can be performed, for example, by the following procedure, but is not limited thereto.

The amount of antibody is measured as described above to select a positive well. Appropriate feeder cells are selected and added to a 96 well plate. The cells are aspirated from the antibody-positive well and suspended to a density of 30 cells/mL in a complete medium (e.g., 10% FCS and P/S-added RMPI1640). The suspension is added at 0.1 mL (3 cells/well) to a well plate added with feeder cells, the remaining cell suspension is diluted to 10 cells/mL and similarly poured to another well (1 cell/well), and the remaining cell suspension is further diluted to 3 cells/mL and poured to another well (0.3 cell/well). The cells are incubated for about 2 to 3 weeks until a visible clone appears, the amount of antibody is measured, and positive wells are selected and cloned again. Since cloning is relatively difficult in the case of human cells, a plate of 10 cells/well is also prepared. A monoclonal antibody-producing hybridoma can be generally obtained by two times of subcloning, but it is desirable to carry out periodical recloning for several months more to confirm its stability.

Hybridoma can be cultured in vitro or in vivo.

As the culture method in vitro, a method including gradually scaling up a monoclonal antibody producing hybridoma obtained as mentioned above from the well plate while keeping the cell density at, for example, about $10^5$-$10^6$ cells/mL and gradually reducing the FCS concentration can be mentioned.

As the culture method in vivo, a method including intraperitoneally injecting about $10^6$-$10^7$ cells of hybridoma 5 to 10 days later to a mouse with plasmacytoma (MOPC) induced by injecting mineral oil into the abdominal cavity (mouse histocompatible with parent strain of hybridoma), and collecting ascites fluid under anesthesia 2 to 5 weeks later can be mentioned.

(b) Purification of Monoclonal Antibody

Separation and purification of the monoclonal antibody can be performed according to a method known per se, for example, a method of immunoglobulin separation and purification [e.g., salting-out, alcohol precipitation, isoelectric point precipitation, electrophoresis, adsorption and desorption with ion exchangers (e.g., DEAE, QEAE), ultracentrifugation, gel filtration, specific purification comprising collecting only the antibody using an activated adsorbent such as an antigen-bound solid phase, Protein A, or Protein G, and dissociating the linkage to separate the desired antibody].

As described above, a monoclonal antibody can be produced by culturing hybridoma in vivo or ex vivo in a warm-blooded animal and collecting the antibody from the body fluid or culture thereof.

To inhibit the activity of an immune checkpoint protein, the antibody to the immune checkpoint protein must neutralize the function of the immune checkpoint protein. Thus, the obtained monoclonal antibody needs to be examined for the neutralization activity. The neutralization activity can be measured, for example, by comparing the level of binding, and the like of PD-1 and PD-L1 in the presence and absence of the antibody.

In one preferred embodiment, since the antibody of the present invention is used as a pharmaceutical for a human recipient, the antibody of the present invention (preferably monoclonal antibody) is an antibody having a reduced risk of exhibiting antigenicity when administered to humans, specifically a complete human antibody, a humanized antibody, a mouse-human chimera antibody or the like, and particularly preferably a complete human antibody.

(3) Preparation of Polyclonal Antibody

The polyclonal antibody of the present invention can be produced according to a method known per se or a method based thereon. For example, the polyclonal antibody of the present invention can be produced by forming an immunoantigen (protein or peptide antigen) itself or a complex thereof with a carrier protein, immunizing a warm-blooded animal with the complex in the same manner as the above-described method of monoclonal antibody production, collecting a product containing an antibody against the immune checkpoint protein from the immunized animal, and separating and purifying the antibody.

Regarding the complex of immunoantigen and carrier protein used to immunize a warm-blooded animal, as the kind of carrier protein and the mixing ratio of carrier protein and hapten, anything may be cross-linked at any ratio as long as an antibody against the immunizing hapten cross-linked to the carrier protein is efficiently produced; for example, a method that comprises coupling bovine serum albumin, bovine thyroglobulin, hemocyanin or the like to the hapten in a ratio by weight of about 0.1 to about 20, preferably about 1 to about 5, to 1 of hapten, can be used.

Various condensing agents can be used for the coupling of hapten and carrier protein; glutaraldehyde, carbodiimide, maleimide activated ester, activated ester reagents comprising the thiol group or the dithiopyridyl group, and the like can be used.

The condensation product is administered as is, or along with a carrier or a diluent, to a warm-blooded animal at a site enabling antibody production by its administration. In order to increase antibody productivity upon the administration, Freund's complete adjuvant or Freund's incomplete adjuvant may be administered. Dosing is normally performed about 2 to about 10 times in total every 1 to 6 weeks.

The polyclonal antibody can be collected from blood, ascites fluid and the like, preferably blood, of a warm-blooded animal immunized by the above-described method.

Polyclonal antibody titer in antiserum can be determined in the same manner as the above-described determination of antibody titer in anti-serum. Separation and purification of the polyclonal antibody can be performed according to a method of immunoglobulin separation and purification, as in the above-described separation and purification of monoclonal antibody.

HVJ-E and an inhibitor of an immune checkpoint protein obtained as in the above can be provided as anticancer agents.

In the below-mentioned Examples in the present specification, a combined administration of HVJ-E and an anti-PD-1 antibody showed the effect of suppressing tumor growth and the effect of improving the survival rate of tumor-bearing mice than the single administration of HVJ-E or single administration of the anti-PD-1 antibody. From the above, it is suggested that the combined administration of HVJ-E and an inhibitor of an immune checkpoint protein can treat the development and progression of cancer. Therefore, the present invention can provide an anticancer agent containing HVJ-E and an inhibitor of an immune checkpoint protein (anticancer agent of the present invention).

Examples of the subject of administration of the anticancer agent of the present invention include humans and other warm-blooded animals (e.g., mouse, rat, rabbit, sheep, swine, bovine, cat, dog, monkey, avian and the like), preferably human.

The cancer to be the application target of the anticancer agent of the present invention includes, but not particularly limited to, melanoma (malignant melanoma), Merkel cell carcinoma, lung cancer, mesothelioma, head and neck cancer, esophagus cancer, gastric cancer, liver cancer, pancreatic cancer, large intestine cancer, prostate cancer, kidney cancer, bladder cancer, urinary tract epithelial cancer, breast cancer, uterine cancer, ovarian cancer, brain tumor, thyroid cancer, angiosarcoma, rhabdomyosarcoma, leiomyosarcoma, fibrosarcoma, synovial sarcoma, liposarcoma, neuroendocrine tumor, lymphoma, leukemia and the like. Among these, melanoma, mesothelioma or prostate cancer is more suitable. As mesothelioma, malignant pleuralmesothelioma is more suitable.

The anticancer agent of the present invention may be a combination agent containing HVJ-E and an inhibitor of an immune checkpoint protein (combination agent of the present invention) or a kit containing a pharmaceutical composition containing HVJ-E and a pharmaceutical composition containing an inhibitor of an immune checkpoint protein (kit of the present invention).

When the anticancer agent of the present invention is a combination agent, since the HVJ-E and an inhibitor of an immune checkpoint protein of the present invention are of low toxicity, and the combination agent can be administered as a liquid as it is, or as an appropriate dosage form of a pharmaceutical composition, to humans or other warm-blooded mammals orally or parenterally (e.g., intratumor administration, intravascular administration, subcutaneous administration, intradermal administration and the like). Parenteral administration is preferable, and intratumor administration is more preferable.

As examples of the pharmaceutical composition for parenteral administration, injections, suppositories and the like are used; the injections may include dosage forms such as intratumor injection, intravenous injection, subcutaneous injection, intracutaneous injection, intramuscular injection and drip infusion injection. Such an injection can be prepared according to a publicly known method. An injection can be prepared by, for example, dissolving, suspending or emulsifying the above-mentioned HVJ-E and an inhibitor of an immune checkpoint protein of the present invention in a sterile aqueous or oily solution in common use for injections. As examples of aqueous solutions for injection, physiological saline, an isotonic solution comprising glucose or another auxiliary drug, and the like can be used, which may be used in combination with an appropriate solubilizer, for example, alcohol (e.g., ethanol), polyalcohol (e.g., propylene glycol, polyethylene glycol), non-ionic surfactant [e.g., polysorbate 80, HCO-50 (polyoxyethylene (50 mol) adduct of hydrogenated castor oil)] and the like. As examples of oily solutions, sesame oil, soybean oil and the like can be used, which may be used in combination with benzyl benzoate, benzyl alcohol and the like as solubilizers. The prepared injection solution is preferably filled in an appropriate ampoule. Suppositories used for rectal administration may be prepared by mixing the above-mentioned HVJ-E and an inhibitor of an immune checkpoint protein with an ordinary suppository base.

As the pharmaceutical composition for oral administration, solid or liquid dosage forms, specifically tablets (including sugar-coated tables and film-coated tablets), pills, granules, powders, capsules (including soft capsules), syrups, emulsions, suspensions and the like can be mentioned. Such a composition is produced by a publicly known method, and may comprise a carrier, diluent or excipient in common use in the field of pharmaceutical making. As examples of the carrier or excipient for tablets, lactose, starch, sucrose, magnesium stearate and the like can be used.

For administration to adult cancer patients, the combination agent of the present invention can be administered by direct injection to a tumor site or the vicinity thereof, intradermally or subcutaneously. The dose thereof can be appropriately determined by a doctor or medical professional in consideration of the tumor size, age, body weight and condition of the patients and the like. When the tumor volume is not more than 1,000 mm$^3$ (e.g., about 200 mm$^3$ and the like), the dose of HVJ-E per administration to one tumor site can be set to 3 HAU-750,000 HAU, preferably 30 HAU-3,000,000 HAU, further preferably 300 HAU-200,000 HAU, (e.g., 9,000 HAU-100,000 HAU). It is preferably not more than 100,000 HAU/kg body weight. When the immune checkpoint protein is PD-1 and the tumor volume is not more than 1000 mm$^3$ (e.g., about 200 mm$^3$ and the like), as the dose of the inhibitor of PD-1, the dose of the anti-PD-1 antibody can be set to 0.1 mg-10 mg, preferably 0.3 mg-5 mg, further preferably 1 mg-3 mg (e.g., 2 mg-3 mg), per kg body weight for one administration. When the tumor volume is not more than 1,000 mm$^3$ (e.g., about 200 mm$^3$ and the like), the dose of a nucleic acid containing a base sequence complementary or substantially complementary to the base sequence encoding PD-1 or a part thereof per administration to one tumor site can be set to 10 mg-2000 mg, preferably 20 mg-1000 mg, further preferably 50 mg-300 mg. In addition, the dose of a nucleic acid containing a base sequence complementary or substantially complementary to the base sequence encoding PD-1 or a part thereof is preferably 1 mg-20 mg per 1 kg body weight. It is further preferably 10 mg-500 mg per 1 m$^2$ body surface area.

When the anticancer agent of the present invention is a kit, similar to the combination agent of the present invention, HVJ-E and an inhibitor of an immune checkpoint protein respectively in an appropriate dosage form of a pharmaceutical composition can be administered orally or parenterally to human or other warm-blooded animals. A pharmaceutical composition for parenteral administration and a pharmaceutical composition for oral administration can be prepared in the same manner as in the combination agent of the present invention.

A pharmaceutical composition containing HVJ-E and a pharmaceutical composition containing an inhibitor of an immune checkpoint protein, which are contained in the kit of the present invention, may be administered by the same administration route or different administration routes.

When they are administered by the same route, the dose and administration route of the pharmaceutical composition containing HVJ-E and the pharmaceutical composition containing an inhibitor of an immune checkpoint protein may be similar to those of the combination agent of the present invention.

When they are administered by different routes, the pharmaceutical composition containing HVJ-E is preferably administered to a tumor site or its periphery, intradermally or subcutaneously, an anti-PD-1 antibody is preferably administered intravenously, subcutaneously, intradermally, intraperitoneally or the like, and the nucleic acid containing a base sequence complementary or substantially complementary to the base sequence encoding PD-1 or a part thereof is preferably administered to a tumor site or its periphery, intradermally, intravenously, intradermally, subcutaneously or intramuscularly or the like. The dose thereof may be the same as that in the administration by the same route.

A pharmaceutical composition containing HVJ-E and a pharmaceutical composition containing an inhibitor of an immune checkpoint protein may be administered simultaneously or at different time points. When they are administered at different time points, either may be administered first.

The anticancer effect of HVJ-E itself and the anticancer effect of an inhibitor of an immune checkpoint protein can be combined to achieve an anticancer activity not realizable by separate use thereof. Thus, the doses of HVJ-E and an inhibitor of an immune checkpoint protein can be each reduced as compared to single administration of each of HVJ-E and an inhibitor of an immune checkpoint protein, which is advantageous from the aspect of safety. In addition, the administration frequency can also be determined as appropriate by a doctor or medical professional in consideration of the tumor size, age, body weight and condition of the patient, and the like.

Each of the aforementioned pharmaceutical compositions may comprise any other active ingredients that do not produce an unwanted interaction when formulated with HVJ-E and an inhibitor of an immune checkpoint protein of the present invention.

EXAMPLES

Cell Line and Mouse

B16-F10 mouse melanoma cell line was subjected to maintenance culture in a DMEM medium (Nacalai Tesque Inc.) containing a 10% FBS (BioWest, Nuaille, France) and 0.1 mg/ml penicillin-streptomycin mixed solution (Nacalai Tesque Inc.). 6-week-old female C57BL/6N mouse purchased from Clea Japan was maintained in an aseptic chamber at controlled room temperature and handled according to the Approval protocol and guidelines for animal experiment provisions of Osaka University (Suita, Japan). AB22 mouse mesothelioma cell line DMEM was maintenance cultured in a medium (Nacalai Tesque Inc.) containing 5% FBS (HyClone, South Logan Utah, USA). Eight-week-old female BALB/c mouse purchased from Clea Japan was maintained in an aseptic chamber at controlled room temperature and handled according to the Approval protocol and guidelines for animal experiment provisions of Osaka University (Suita, Japan). TRAMP-C1 mouse prostate cancer cell line was subjected to maintenance culture in a DMEM medium (Nacalai Tesque Inc.) containing a 10% FBS (BioWest, Nuaille, France) and 0.1 mg/ml penicillin-streptomycin mixed solution (Nacalai Tesque Inc.). Myd88−/− TRIF−/− double knockout mouse obtained by crossing 6—was subjected to maintenance culture in a DMEM medium (Nacalai Tesque Inc.) containing a 10% FBS (BioWest, Nuaille, France) and 0.1 mg/ml penicillin-streptomycin mixed solution (Nacalai Tesque Inc.). 7-week-old female C57BL/6N mouse purchased from Clea Japan was maintained in an aseptic chamber at controlled room temperature and handled according to the Approval protocol and guidelines for animal experiment provisions of Osaka University (Suita, Japan).

Virus

HVJ (VR-105 parainfluenza Sendai/52 Z strain) was purchased from ATCC (Manassas, Va.) and prepared according to the method described in Cancer Res. 67, 227-236, 2007. Briefly, a seed solution of HVJ was injected into 10 day-old embryonated hen eggs and the eggs were cultured for 3 days at 37° C. in an incubator. After 3 days, allantoic fluid was collected from the hen eggs injected with HVJ. The recovered virus (living HVJ) was inactivated by UV irradiation (198 mJ/cm$^2$) to prepare HVJ-E.

Anti-PD-1 Antibody

An anti-PD-1 antibody (LEAF™ Purified anti-mouse CD279 (PD-1) antibody, Catalog #: 114108, Clone: RMP1-14) and control antibody having the same isotype of IgG2a (LEAF™ Purified Rat IgG2a, KIsotype Ctrl antibody, Catalog #: 400516, Clone: RTK2758) were purchased from BioLegend (San Diego, Calif., USA).

Example 1 Tumor Inoculation Test (1)

B16-F10 mouse melanoma cells ($10^6$ cells) suspended in 50 μl PBS were intradermally injected into the dorsal of C57BL/6N mice, and the mice were divided into 6 groups (n=4/group). After 6 days when the tumor diameter became 3-5 mm (Day 0), in 3 groups out of the aforementioned 6 groups, HVJ-E (particles number 1.0×10$^{10}$ (1000 HAU)) dissolved in the total amount 50 μl of PBS was subcutaneously injected to the mice every two days and 6 times in total. In the remaining 3 groups, 50 μl of PBS alone was subcutaneously injected to the mice every two days and 6 times in total. Furthermore, to the above-mentioned mouse administered with HVJ-E was given a single intraperitoneal injection of 100 μl of PBS alone (HVJ-E administration group), anti-PD-1 antibody (100 μg) dissolved in 100 μl of PBS (antiPD-1 ab+HVJ-E administration group) or an isotype control antibody (100 μg) dissolved in 100 μl of PBS (isotype IgG2b+HVJ-E administration group) on Day 0. Similarly, to the above-mentioned mouse administered with PBS was given a single intraperitoneal injection of 100 μl of PBS alone (PBS administration group), an anti-PD-1 antibody (100 μg) dissolved in 100 μl of PBS (antiPD-1 ab administration group) or an isotype control antibody (100 μg) dissolved in 100 μl of PBS (isotype IgG2b administration group) on Day 0. The tumor size was observed up to day 12. The tumor volume was measured using a vernier caliper under blind trial and calculated using the following formula:

tumor volume (mm$^3$)=length×(width)$^2$/2

The results are shown in FIG. 1. The HVJ-E administration group and antiPD-1 ab administration group each showed an antitumor effect with the tumor size as an index relative to the negative control group, PBS administration group. The antiPD-1 ab+HVJ-E administration group showed enhancement of the antitumor effect with the tumor size as an index relative to the HVJ-E administration group and antiPD-1 ab administration group. On the other hand, the isotype IgG2b+HVJ-E administration group did not show enhancement of the antitumor effect relative to the HVJ-E administration group and isotype IgG2b administration group.

Example 2 Tumor Inoculation Test (2)

B16-F10 mouse melanoma cells ($10^6$ cells) suspended in 50 μl PBS were intradermally injected into the dorsal of C57BL/6N mice, and the mice were divided into 4 groups. After 6 days when the tumor diameter became 3-5 mm (Day 0), in 2 groups out of the aforementioned 4 groups, HVJ-E (particles number 1.0×10$^{10}$ (1000 HAU)) dissolved in the total amount 50 μl of PBS was intratumorally injected to the mice every two days and 3 times in total. From Day 18, the dosage form and dosage were changed, and HVJ-E (particles number 5.0×10$^{10}$ (5000 HAU)) was intratumorally injected every two days and 6 times in total. In the remaining 2 groups, 50 μl of PBS alone was intratumorally injected to the mice every two days and 3 times in total. From Day 18, 50 μl of PBS alone was intratumorally injected to the mice every two days and 6 times in total. Furthermore, to the above-mentioned mouse administered with HVJ-E was given intraperitoneal injection of 100 μl of PBS alone (HVJ-E administration group), or an anti-PD-1 antibody (100 μg) dissolved in 100 μl of PBS (antiPD-1 ab+HVJ-E administration group) 3 times in total on Day 0, Day 14 and Day 18. Similarly, to the above-mentioned mouse administered with PBS was given an intraperitoneal injection of 100 μl of PBS alone (PBS administration group), or an anti-PD-1 antibody (100 μg) dissolved in 100 μl of PBS (antiPD-1 ab administration group) 3 times in total on Day 0, Day 14 and Day 18. The tumor size was observed up to day 30 according to the same calculation formula as in Example 1.

Figure 2:
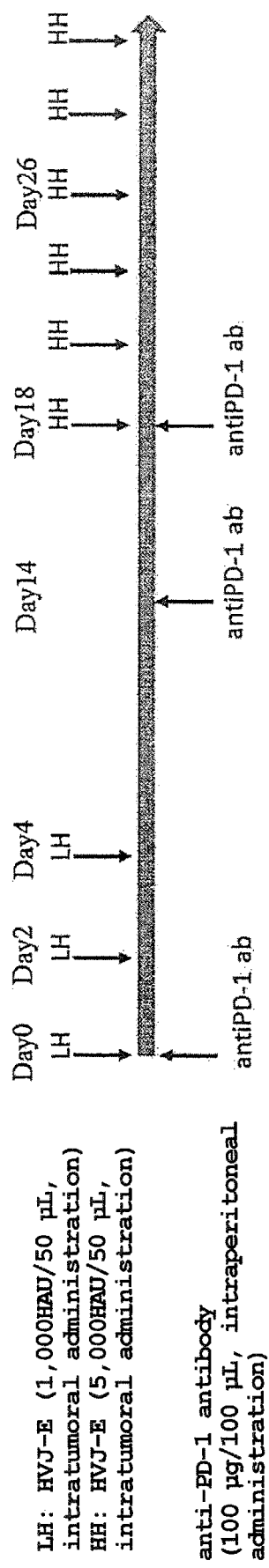
FIG. 2 shows a tumor volume when PBS, an anti-PD-1 antibody (intraperitoneal administration), HVJ-E (intratumoral administration) or HVJ-E (intratumoral administration)+anti-PD-1 antibody (intraperitoneal administration) was administered to a malignant melanoma-transplanted mouse and the mouse was observed for 30 days after the start of the administration.
Figure 2:
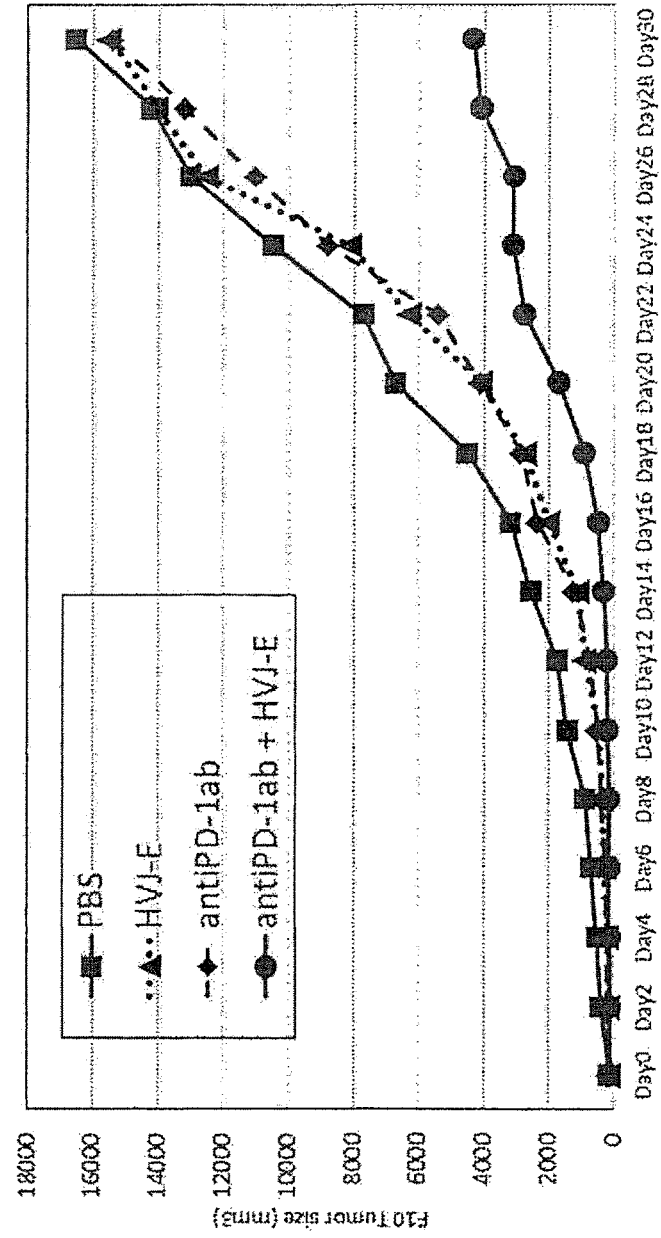

The results are shown in FIG. 2. The HVJ-E administration group showed an antitumor effect with the tumor size as an index relative to the negative control group, PBS administration group on day 14 after the start of the administration. On day 30 after the start of the administration, it did not show an antitumor effect even though the dose of HVJ-E was 5-fold in the administrations after day 18. Similarly, the antiPD-1 ab administration group showed an antitumor effect with the tumor size as an index relative to the negative control group, PBS administration group, on day 14 after the start of the administration, but did not show an antitumor effect on day 30 after the start of the administration. In contrast, the antiPD-1 ab+HVJ-E administration group showed enhancement of the antitumor effect with the tumor size as an index relative to the HVJ-E administration group and antiPD-1 ab administration group on both evaluation time points of day 14 and day 30 after the start of the administration.

Example 3 Tumor Inoculation Test (3)

AB22 mouse mesothelioma cells ($10^6$ cells) suspended in 50 μl of PBS were intradermally injected into BALB/c mouse, and the mice were divided into 3 groups. After 4, 7, 8, 10, 12, 14, 17, 18, 20, 22 and 24 days, to one group out of the aforementioned 3 groups was intratumorally administered total 11 times HVJ-E (particles number $1.0\times10^{10}$ (1000 HAU)) dissolved in the total amount of 50 µl of PBS. In the remaining 2 groups, 50 µl of PBS alone was intratumorally injected. Furthermore, to the above-mentioned mouse administered with HVJ-E was given intraperitoneal injection of an anti-PD-1 antibody (100 µg) dissolved in 100 µl of PBS (antiPD-1 ab+HVJ-E administration group) 2 times in total on Day 4 and Day 18. Similarly, to the above-mentioned mouse administered with PBS was given an intraperitoneal injection of 100 µl of PBS alone (PBS administration group), or an anti-PD-1 antibody (100 µg) dissolved in 100 µl of PBS (antiPD-1 ab administration group) 2 times in total on Day 4 and Day 18. The tumor size was observed up to day 27 according to the same calculation formula as in Example 1.

Figure 3:
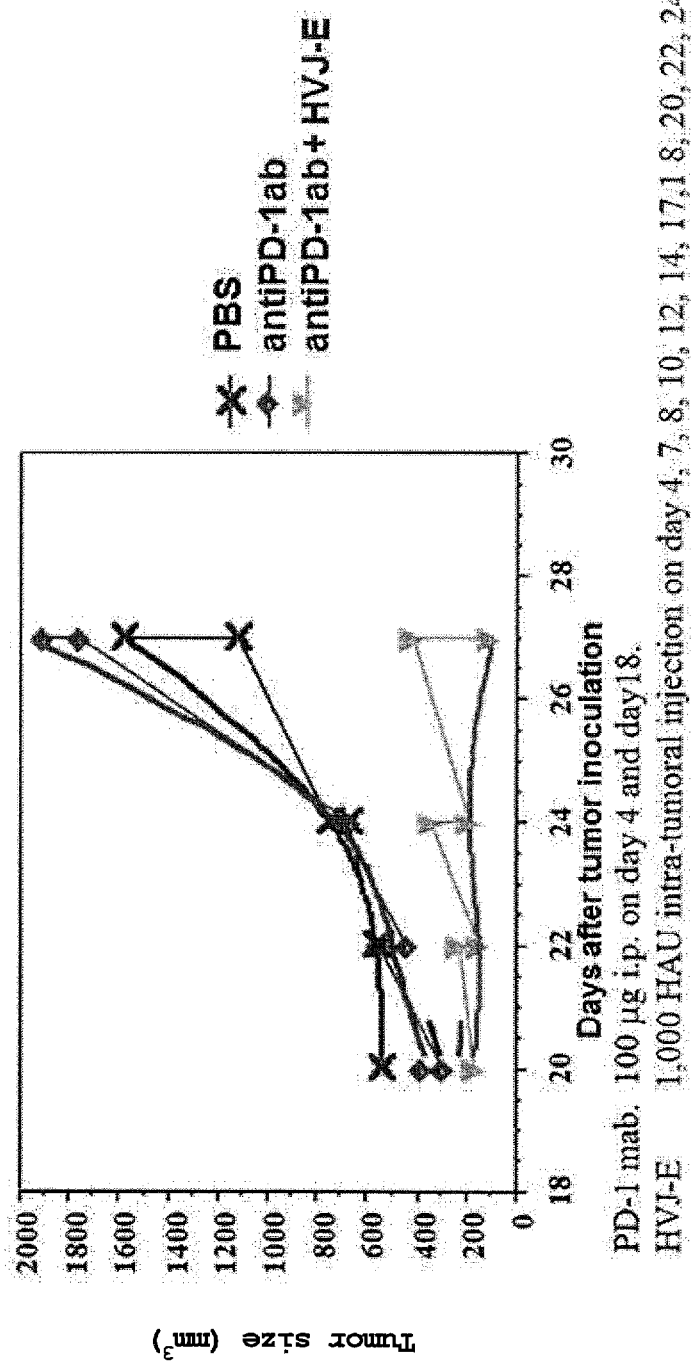
FIG. 3 shows a tumor volume when PBS, an anti-PD-1 antibody (intraperitoneal administration) or HVJ-E (intratumoral administration)+anti-PD-1 antibody (intraperitoneal administration) was administered to a malignant pleuralmesothelioma-transplanted mouse.
Figure 4:
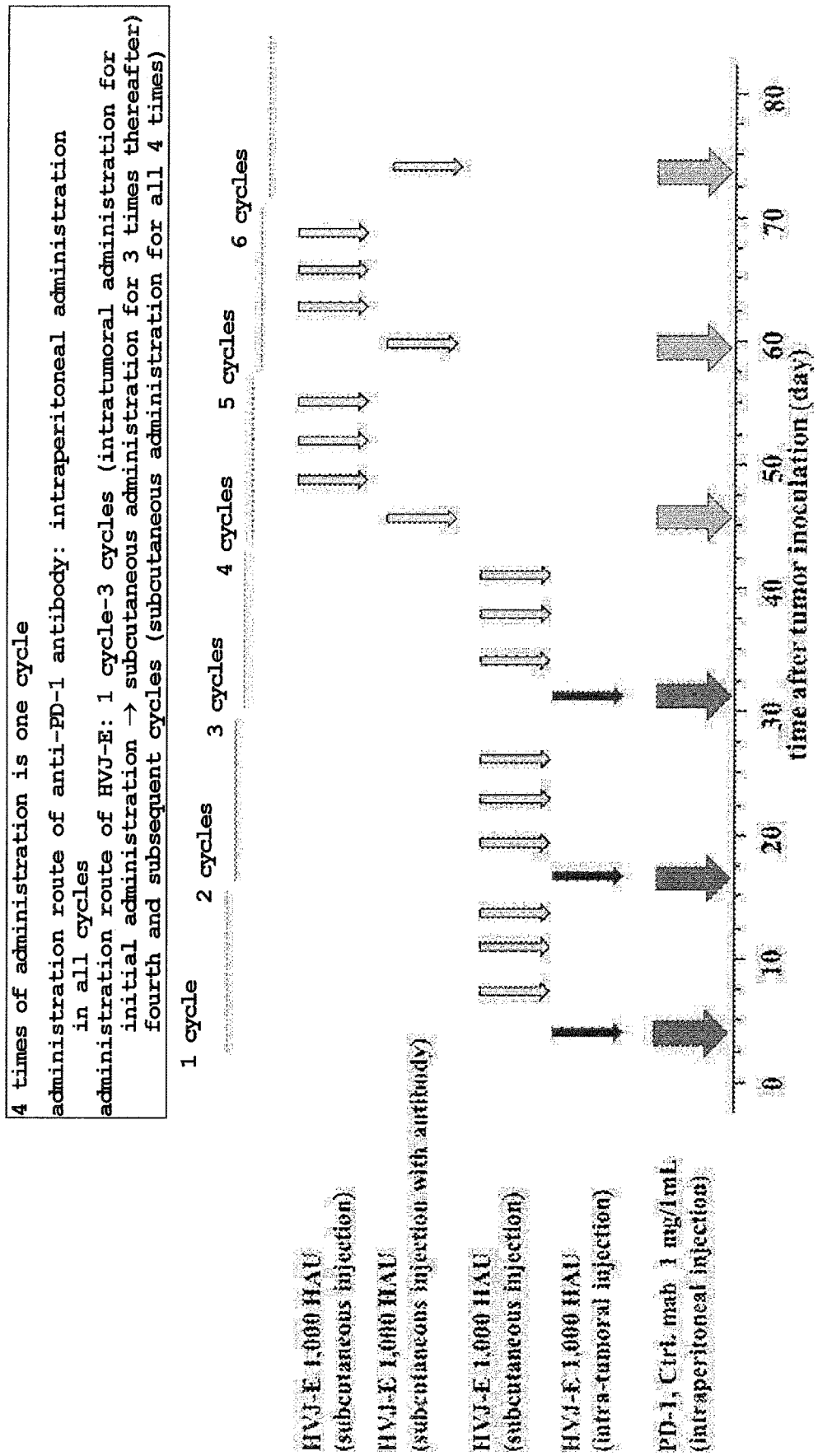
FIG. 4 shows an administration schedule of PBS, an anti-PD-1 antibody, HVJ-E+isotype control antibody (IgG2b) or HVJ-E+anti-PD-1 antibody administered to a malignant pleuralmesothelioma-transplanted mouse.

The results are shown in FIG. 3. The antiPD-1 ab administration group did not show an antitumor effect with the tumor size as an index relative to the negative control group, PBS administration group, on day 27 after the start of the administration. In contrast, the antiPD-1 ab+HVJ-E administration group showed enhancement of the antitumor effect with the tumor size as an index relative to the antiPD-1 ab administration group on evaluation time point of day 27 after the start of the test.

Example 4 Tumor Inoculation Test (4)

AB22 mouse mesothelioma cells ($10^6$ cells) suspended in 50 µl of PBS were intrapleurally injected into BALB/c mouse, and the mice were divided into 4 groups. From 4 days later, to 2 groups out of the aforementioned 4 groups was administered HVJ-E (particle number $1.0\times10^{10}$ (1000 HAU)) dissolved in the total amount of 50 µl of PBS 4 times in total in 2 weeks (intrapleural administration for initial time, and 3 times of subcutaneous administration). With this administration as one cycle, 3 cycles were repeated and total 12 times of administration was performed in 6 weeks. After week 7, 4 times of administration in each cycle were changed to subcutaneous administration and 4 times of administration was performed in 2 weeks. With this administration as one cycle, 3 cycles were repeated and total 9 times of administration was performed in 6 weeks (initial subcutaneous administration alone was performed for 3rd cycle). In the remaining 2 groups, 50 µl of PBS alone was administered. Finally, the number of administration of HVJ-E or PBS up to day 73 was total 3 times of intrapleural administration and total 18 times of subcutaneous administration. Furthermore, to the above-mentioned mouse administered with HVJ-E was given intraperitoneal injection of an anti-PD-1 antibody (100 µg) dissolved in the total amount of 100 µl of PBS (antiPD-1 ab+HVJ-E administration group) or an isotype control antibody (100 µg) (isotype IgG2b+HVJ-E administration group) at the time of initial administration of each of the above-mentioned HVJ-E administration cycles from day 4. Similarly, to the above-mentioned mouse administered with PBS was given an intraperitoneal injection of 100 µl of PBS alone (PBS administration group) or an anti-PD-1 antibody (100 µg) dissolved in 100 µl of PBS (antiPD-1 ab administration group) at the time of initial administration of each of the above-mentioned HVJ-E administration cycles from day 4. Finally, the number of administration of PBS, anti-PD-1 antibody or isotype control antibody was 6 times in total. The survival rate was observed up to day 73.

Figure 5:
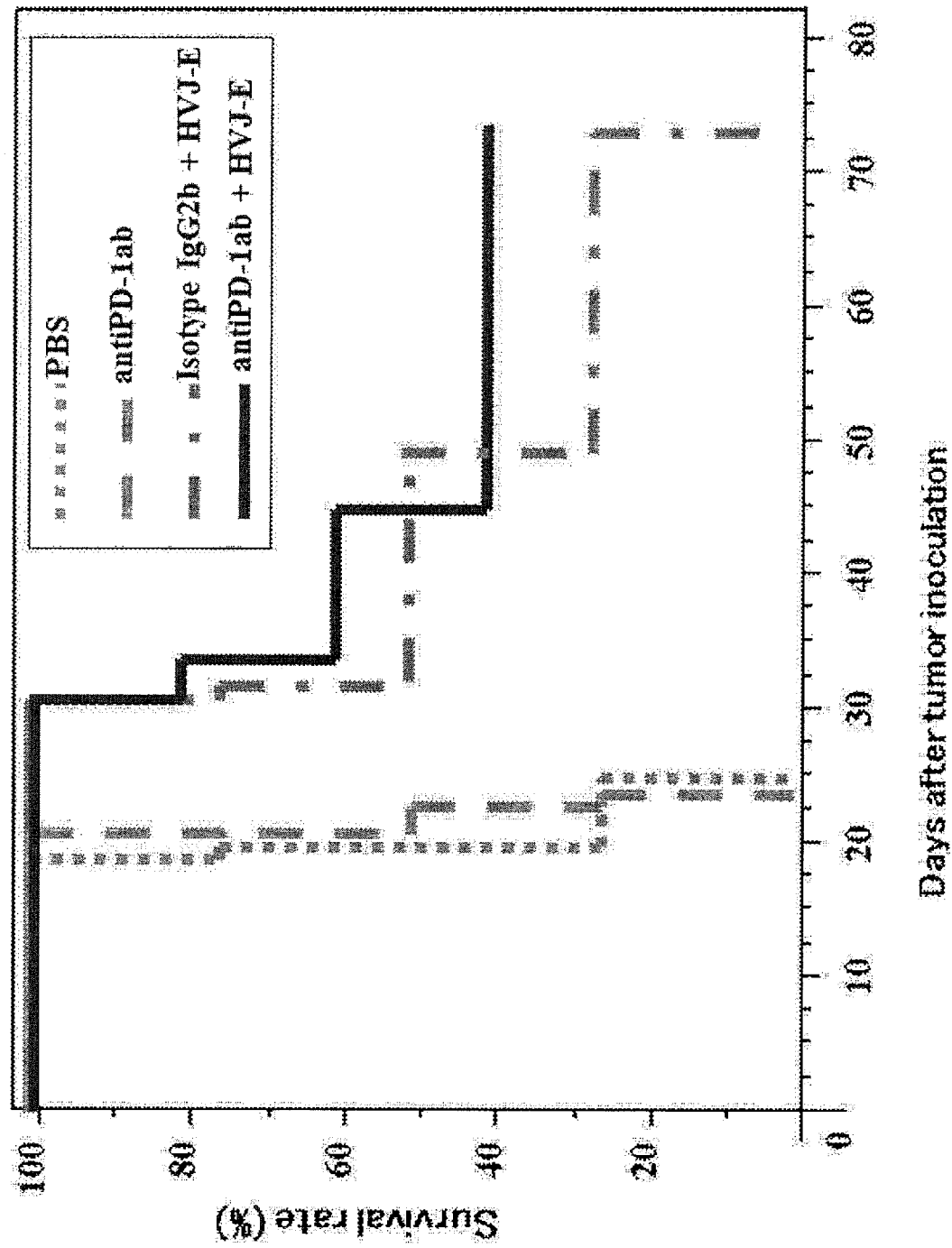
FIG. 5 shows the survival rate of mouse when PBS, an anti-PD-1 antibody, HVJ-E+isotype control antibody (IgG2b) or HVJ-E+anti-PD-1 antibody was administered to a malignant pleuralmesothelioma-transplanted mouse.

The results are shown in FIG. 5. The antiPD-1 ab administration group did not show an antitumor effect with the survival rate as an index relative to the negative control group, PBS administration group and the survival rate became 0% (all cases were dead) on day 25. While the isotype IgG2b+HVJ-E administration group showed an antitumor effect with the enhancement of the survival rate (prolongation of survival period) as an index relative to the negative control group, the survival rate of the PBS administration group became 0% (all cases were dead) on day 73 after the start of the test. On the other hand, the survival rate of the antiPD-1 ab+HVJ-E administration group was 40% on day 73 after the start of the test, and the group showed a higher survival rate than the antiPD-1 ab administration group and isotype IgG2b+HVJ-E administration group.

Example 5 Tumor Inoculation Test (5)

TRAMP-C1 mouse prostate cancer cells ($10^6$ cells) suspended in 50 µl of PBS were mixed with 50 µl of Matrigel (Corning Matrigel Basement Membrane Matrix High Concentration, Phenol Red Free, Catalog #:354262) to give a total 100 µl of a solution. The solution was intradermally injected into the dorsal of C57BL/6N mouse, and the mice were divided into 5 groups (n=4/group). With the day when the tumor diameter became not less than 5 mm as Day 0, HVJ-E (particles number $1.0\times10^{10}$ (1000 HAU)) dissolved in the total amount 50 µl of PBS was intradermally injected to the mice every two days and 6 times in total (Day 0, Day 2, Day 4, Day 6, Day 8, Day 10) and thereafter intradermally injected to the mice 6 times (Day 20, Day 22, Day 24, Day 26, Day 28, Day 30) in 3 groups out of the aforementioned 5 groups. In the remaining 2 groups, 50 µl of PBS alone was intradermally injected 12 times in total on the same day as the above-mentioned HVJ-E administration day (Day 0, Day 2, Day 4, Day 6, Day 8, Day 10, Day 20, Day 22, Day 24, Day 26, Day 28, Day 30). Furthermore, to the above-mentioned mouse administered with HVJ-E was given intratumoral injection of 100 µl of PBS alone (HVJ-E group), anti-PD-1 antibody (100 µg) dissolved in 100 µl of PBS (PD-1 ab+HVJ-E group) or an isotype control antibody (100 µg) dissolved in 100 µl of PBS (Ctrl IgG+HVJ-E group) two times on Day 0 and Day 20. Similarly, to the above-mentioned mouse administered with PBS alone was given intratumoral injection of 100 µl of PBS alone (PBS group), or an anti-PD-1 antibody (100 µg) dissolved in 100 µl of PBS (PD-1 ab group) two times on Day 0 and Day 20. The tumor size was observed up to day 30. The tumor volume was measured using a vernier caliper under blind trial and calculated using the following formula:

tumor volume (mm$^3$)=length×(width)$^2$/2

Figure 6:
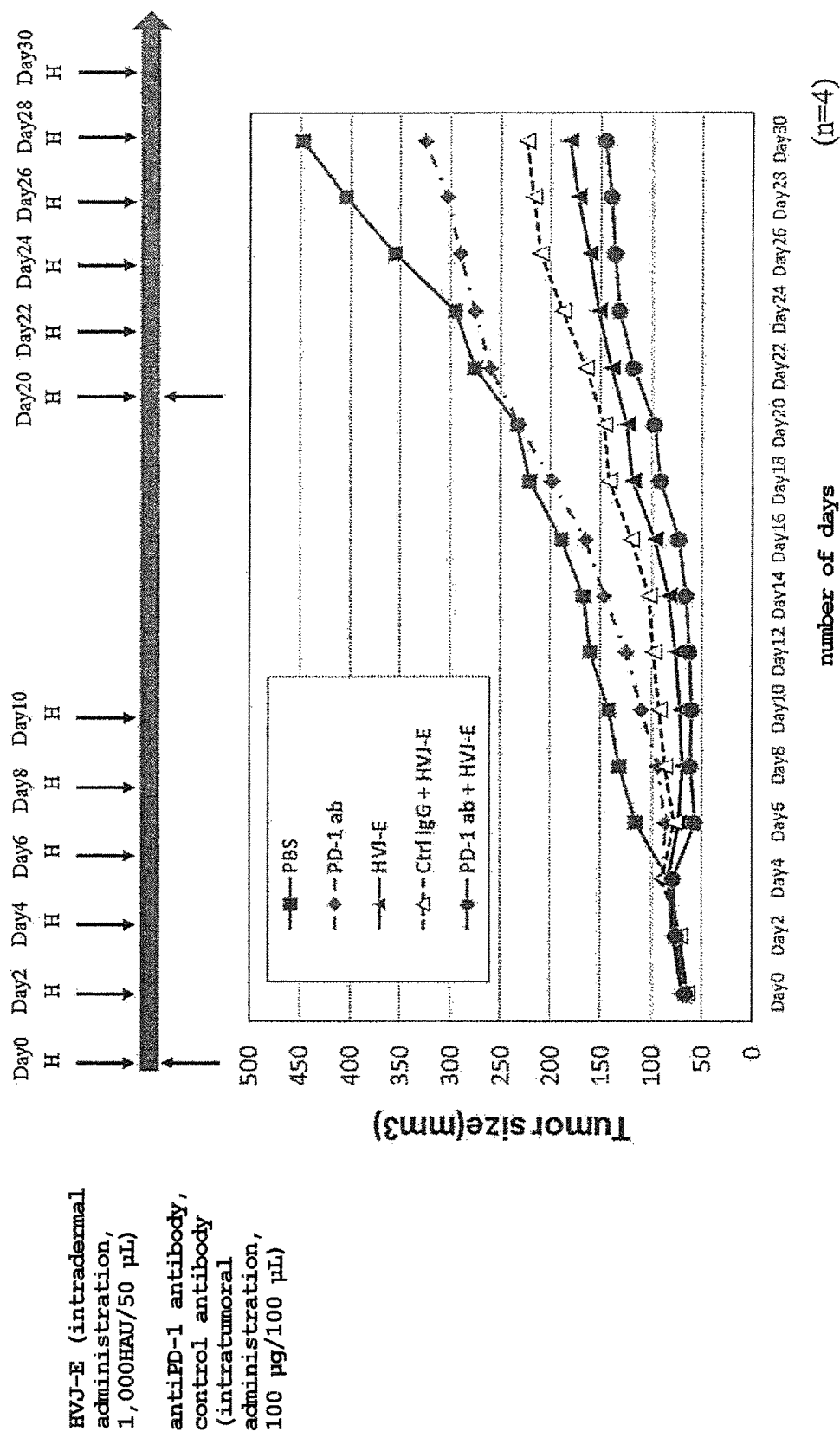
FIG. 6 shows a tumor volume when PBS, an anti-PD-1 antibody (intratumoral administration), HVJ-E (intradermal administration), HVJ-E (intradermal administration)+isotype control antibody (intratumoral administration) or HVJ-E (intradermal administration)+anti-PD-1 antibody (intratumoral administration) was administered to a prostate cancer-transplanted mouse and the mouse was observed for 30 days after the start of the administration.

The results are shown in FIG. 6. The HVJ-E group showed an antitumor effect with the tumor size as an index relative to the negative control group, PBS group. On the other hand, the PD-1 ab group showed almost same tumor size as the negative control group, PBS group, at the time point of day 20 from the start of the administration. The PD-1 ab+HVJ-E group showed enhancement of the antitumor effect with the tumor size as an index relative to the HVJ-E group and PD-1 ab group. On the other hand, the Ctrl IgG+HVJ-E group showed lower antitumor effect than the HVJ-E group.

INDUSTRIAL APPLICABILITY

An anticancer agent containing HVJ-E (hemagglutinating virus of Japan envelope) and an inhibitor of an immune checkpoint protein as active ingredients exhibits a remarkable antitumor effect compared to single use of each of them and is useful as a novel therapeutic agent for cancer.

This application is based on patent application No. 2016-214198 filed in Japan (filing date: Nov. 1, 2016), the contents of which are incorporated in full herein.

The invention claimed is:

1. A method for slowing the progression of melanoma, mesothelioma, or prostate cancer, comprising administering multiple doses of an effective amount of HVJ-E and anti-PD-1 antibody RMP1-14 to a subject, thereby slowing the progression of melanoma, mesothelioma, or prostate cancer in the subject.

2. The method according to claim 1, wherein HVJ-E and anti-PD-1 antibody RMP1-14 are administered to the subject in the form of a pharmaceutical composition that comprises both HVJ-E and anti-PD-1 antibody RMP1-14.

3. The method according to claim 1, wherein HVJ-E and anti-PD-1 antibody RMP1-14 are administered to the subject in the form of a first pharmaceutical composition that comprises HVJ-E and a second pharmaceutical composition that comprises anti-PD-1 antibody RMP1-14 and that is not the same as the first pharmaceutical composition.

4. The method according to claim 1, wherein the subject is a human that has melanoma, and the administration of multiple doses of an effective amount of HVJ-E and anti-PD-1 antibody RMP1-14 slows the progression of melanoma in the subject.

5. The method according to claim 1, wherein the subject is a human that has mesothelioma, and the administration of multiple doses of an effective amount of HVJ-E and anti-PD-1 antibody RMP1-14 slows the progression of mesothelioma in the subject.

6. The method according to claim 1, wherein the subject is a human that has prostate cancer, and the administration of multiple doses of an effective amount of HVJ-E and anti-PD-1 antibody RMP1-14 slows the progression of prostate cancer in the subject.

* * * * *